United States Patent [19]
Monforte et al.

[11] Patent Number: 6,051,378
[45] Date of Patent: Apr. 18, 2000

[54] METHODS OF SCREENING NUCLEIC ACIDS USING MASS SPECTROMETRY

[75] Inventors: Joseph Albert Monforte, Berkeley; Thomas Andrew Shaler, San Francisco; Yuping Tan, Fremont; Christopher Hank Becker, Menlo Park, all of Calif.

[73] Assignee: GeneTrace Systems Inc., Alameda, Calif.

[21] Appl. No.: 08/811,505

[22] Filed: Mar. 4, 1997

Related U.S. Application Data

[60] Provisional application No. 60/012,752, Mar. 4, 1996.

[51] Int. Cl.$^7$ .............................. C12Q 1/68; C12P 19/34; C07H 21/02; C07H 21/04
[52] U.S. Cl. ........................ 435/6; 435/91.1; 435/91.2; 536/23.1; 536/24.1; 536/24.33
[58] Field of Search .............................. 435/6, 91.1, 91.2, 435/183, 287.2; 536/23.1, 24.3, 24.33; 935/76, 77

[56] References Cited

U.S. PATENT DOCUMENTS

| | | | |
|---|---|---|---|
| 4,775,619 | 10/1988 | Urdea | 435/6 |
| 4,935,357 | 6/1990 | Szybalski | 435/91 |
| 5,003,059 | 3/1991 | Brennan | 536/27 |
| 5,064,754 | 11/1991 | Mills | 435/6 |
| 5,075,217 | 12/1991 | Weber | 435/6 |
| 5,288,644 | 2/1994 | Beavis et al. | 436/94 |
| 5,364,759 | 11/1994 | Caskey et al. | 435/6 |
| 5,369,004 | 11/1994 | Polymeropoulos et al. | 435/6 |
| 5,378,602 | 1/1995 | Polymeropoulos et al. | 435/6 |
| 5,464,985 | 11/1995 | Cornish et al. | 250/396 R |
| 5,468,610 | 11/1995 | Polymeropoulos et al. | 435/6 |
| 5,503,980 | 4/1996 | Cantor | 435/6 |
| 5,508,169 | 4/1996 | Deugau et al. | 435/6 |
| 5,547,835 | 8/1996 | Koster | 435/6 |
| 5,580,733 | 12/1996 | Levis et al. | 435/6 |
| 5,582,979 | 12/1996 | Weber | 435/6 |
| 5,599,666 | 2/1997 | Schumam et al. | 435/6 |
| 5,605,798 | 2/1997 | Köster | 435/6 |
| 5,622,824 | 4/1997 | Köster | 435/6 |
| 5,625,184 | 4/1997 | Vestal et al. | 250/287 |
| 5,627,369 | 5/1997 | Vestal et al. | 250/287 |
| 5,691,141 | 11/1997 | Köster | 435/6 |
| 5,700,642 | 12/1997 | Monforte et al. | 435/6 |
| 5,762,876 | 6/1998 | Lincoln et al. | 422/67 |
| 5,885,775 | 3/1999 | Haff et al. | 435/6 |
| 5,888,819 | 3/1999 | Goelet et al. | 435/5 |

FOREIGN PATENT DOCUMENTS

| | | |
|---|---|---|
| WO 91/11533 | 8/1991 | WIPO . |
| WO 91 15600 | 10/1991 | WIPO . |
| WO 93/08305 | 10/1992 | WIPO . |
| WO 94/16090 | 1/1994 | WIPO . |
| WO 94/16101 | 7/1994 | WIPO . |
| WO 95 07361 | 3/1995 | WIPO . |
| WO 95/04160 | 9/1995 | WIPO . |
| WO 96/29431 | 9/1996 | WIPO . |
| WO 96 32504 | 10/1996 | WIPO . |
| WO 96/37630 | 11/1996 | WIPO . |
| WO 97/33000 | 3/1997 | WIPO . |
| WO 97/27327 | 7/1997 | WIPO . |

OTHER PUBLICATIONS

Bukhard Herpich and Gerd–Joachim Krauss, "HPLC of Nucleic Acid Components with Volatile Mobile Phases I. Fast Nucleotide Separations using Ammonium Catrbonate and Ammonium Bicarbonate Gradients." Journal of High Resolutin Chromatography, vol. 15, p. 41, Jan. 1992.

Arnott et al., "Construction and performance of a laser desorption/ionization TOF mass spectrometer system: applications to problems in peptide, protein, and DNA structural analysis," The 40th ASMS Conference on Mass Spectrometry and Allied Topics, May 31–Jun. 5, Washington, D.C., pp. 328–329, 1992.

Bevan et al., "The analysis of oligonucleotides and their phosphoramidate analogues by LSIMS mass spectrometry," The 39th ASMS Conference on Mass Spectrometry and Allied Topics, pp. 983–984, 1989.

Edmonds et al., "Electrospray ionization mass spectrometry and tandem mass spectrometry of small oligonucleotides," 37th ASMS Conference on Mass Spectrometry and Allied Topics, May 21–26, Miami Beach, FL, pp. 844–845, 1989.

Jacobson et al., "Applications of mass spectrometry to DNA sequencing,", *GATA*, 8(8):223–229, 1991.

Karas and Bahr, "Matrix–assisted laser desorption ionization mass spectrometry," *Mass Spectrometry Reviews*, 10:335–357, 1991.

Limbach et al., "Characterization of oligonucleotides and nucleic acids by mass spectrometry," *Current Opinion Biotechnology*, 6:96–102, 1995.

McNeal et al., "A new method for the analysis of fully protected oligonucleotides by $^{252}$Cf–plasma desorption mass spectrometry. 3. Positive ions," *J. Am. Chem. Soc.*, 104:981–984, 1982.

Mizusawa et al., "Improvement of the dideoxy chain termination method of DNA sequencing by use of deoxy–7–deazaguanosine triphosphate in place of dGTP," *Nucl. Acids Res.*, 14(3):1319–1325, 1986.

Mock et al., "Sample immobilization protocols for matrix assisted laser desorption mass spectrometry," The 40th ASMS Conference on Mass Spectrometry and Allied Topics, pp. 1921–1922, 1992.

Musser and Kelley, "Sensitivity enhancement for static and continuous flow FAB/MS analysis of nucleotides by quaternary amine surfactants," The 39th ASMS Conference on Mass Spectrometry and Allied Topics, pp. 374–375, 1989.

(List continued on next page.)

*Primary Examiner*—Kenneth R. Horlick
*Assistant Examiner*—Jeffrey Siew
*Attorney, Agent, or Firm*—Arnold White & Durkee

[57] ABSTRACT

This invention relates to methods for screening nucleic acids for mutations by analyzing nonrandomly fragmented nucleic acids using mass spectrometric techniques and to procedures for improving mass resolution and mass accuracy of these methods of detecting

31 Claims, 28 Drawing Sheets

OTHER PUBLICATIONS

Nordhoff et al., "Matrix–assisted laser desorption/ionization mass spectrometry of nucleic acids with wavelengths in the ultraviolet and infrared," *Rapid Comm. Mass Spectrometry*, 6:771–776, 1992.

Overberg et al., "Laser desorption mass spectrometry, Part II performance and applications of matrix–assisted laser desorption/ionization of large biomolecules," *Anal. Chem.*, 181–197, 1992.

Parr et al., "Matrix–assisted laser desorption/ionization mass spectrometry of synthetic oligodeoxyribonucleotides," *Rapid Comm. Mass Spectrometry*, 6:369–372, 1992.

Spengler et al., "Molecular weight determination of underivatized oligodeoxyribonucleotides by positive–ion matrix–assisted ultraviolet laser–desorption mass spectrometry," *Rapid Comm. Mass Spectrometry*, 4(4):99–102, 1990.

Stahl et al., "Solid phase DNA sequencing using the biotin–avidin system," *Nucl. Acids Res.*, 16(7):3025–3039, 1988.

Stults and Marsters, "Characterization of oligodeoxynucleotide conjugates by electrospray ionization mass spectrometry," Proceedings of the 39th ASMS Conference on Mass Spectrometry and Allied Topics, May 19–24, Nashville, TN, pp. 1161–1162, 1991.

Stults and Marsters, "Improved electrospray ionization of synthetic oligodeoxynucleotides," *Rapid Comm. Mass Spectrometry*, 5:359–363, 1991.

Tong and Smith, "Solid–phase method for the purification of DNA sequencing reactions," *Anal. Chem.*, 64:2672–2677, 1992.

Trainor, "DNA sequencing, automation, and the human genome," *Anal. Chem.*, 62:418–426, 1990.

PCT Search Report dated Jul. 23, 1997 International Application No. PCT/US 97/03499.

International Search Report dated Jan. 20, 1998(PCT/US 97/17101) (GETR:018P).

Sedlak, "GeneTrace Systems Bets its Future in Genomics on TOF Mass Spectroscopy," *Genetic Engineering News*, 16(21):, 1996. (website: http://www.genetrace.com).

Tang et al., "Detection of 500–Nucleotide DNA by Laser Desorption Mass Spectrometry," *Rapid Commun. in Mass Spectrometry*, 8(9):727–730, 1994.

Abrams, et al,. "Comprehensive Detection of Single Base Changes in Human Genomic DNA Using Denaturing Gradient Gel Electrophoresis and a GC Clamp," *Genomics*, 7:463–475, 1990.

Bai, Jian, et al., "Matrix–Assisted Laser Desorption/Ionization Mass Spectrometry of Restriction Enzyme–Digested Plasmid DNA Using an Active Nafion Substrate," *Rapid Commun. in Mass Spectrometry*, 8:687–691, 1994.

Bai, Jian, et al., "Procedures for Detection of DNA by Matrix–Assisted Laser Desorption/Ionization Mass Spectrometry Using a Modified Nafion Film Substrate," *Rapid Commun. in Mass Spectrometry*, 9:1172–1176, 1995.

Benner and Jaklevic, "DNA Base–Pair Substitutions Detected in Double–Stranded DNA With Matrix–Assisted Laser Desorption/Ionization Time–of–Flight Mass Spectrometry," *Eur. Mass Spectrum.*, 479–485, 1995.

Benner, Horn, Katz, Jaklevic, "Identification of Denatured Double–stranded DNA by Matrix–Assisted Laser Desorption/Ionization Time–of–Flight Mass Spectrometry," *Rapid Commun. in Mass Spectrom.*, 9:537–540, 1995.

Bergh, et al., "Complete Sequencing of the p53 Gene Provides Prognostic Information in Breast Cancer Patients, Particularly in Relation to Adjuvant Systemic Therapy and Radiotherapy," *Nature Medicine*, 1:1029–1034, 1995.

Chang, et al., "Detection of ΔF508 Mutation of the Cystic Fibrosis Gene by Matrix–Assisted Laser Desorption/Ionization Mass Spectrometry," *Rapid Commun. in Mass Spectometry*, 9:772–774, 1995.

Fang, et al., "Simultaneous Analysis of Mutant and Normal Alleles for Multiple Cystic Fibrosis Mutations by the Ligase Chain Reaction," *Human Mutation*, 6:144–151, 1995.

Fenn, et al., "Electrospray Ionization for Mass Spectrometry Large Biomolecules," *Science*, 246:64–71, 1989.

Hegner, Wagner, Semenza, "Ultralarge Atomically Flat Template–Stripped Au Surfaces for Scanning Probe Microscopy," *Surface Science*, 291:39–46, 1993.

Jurinke, Christian, et al., "Analysis of Ligase Chain Reaction Products Via Matrix–Assisted Laser Desorption/Ionization Time–of–Flight–Mass Spectrometry," *Analytical Biochemistry*, 237:174–181, 1996.

Kirpekar, Nordhoff, Kristiansen, Roepstorff, Lezius, Hahner, Karas, Hillenkamp, "Matrix Assisted Laser Desorption/Ionization Mass Spectrometry of Enzymatically Synthesized RNA Up to 150 kDa," *Nucleic Acids Research*, 22(19):3866–3870, 1994.

Kuimelis and McLaughlin, "Cleavage Properties of an Oligonucleotide Containing a Bridged Internucleotide 5'–phosphorothioate RNA Linkage," *Nucleic Acids Research*, 23:4753–4760, 1995.

Lee, et al., Comparison on Short Tandem Repeat (STR) Detection Using Silver, Fluorescence and Matrix Assisted Laser Desorption Ionization Time–of–Flight Mass Spectrophotometry (MALDITOF–MS), *Proceedings of the Sixth International Symposium on Human Identification*, published by Promega Corp., 1995.

Lee, et al., "DNA Sequencing with Dye–Labeled Terminators and T7 DNA Polymerase: Effect of Dyes and dNTPs on Incorporation of Dye–Terminators and Probability Analysis of Termination Fragments," *Nucleic Acids Research*, 20(10):2471–2483, 1992.

Liang, Gangning, et al., "The Use of 2–Hydroperoxytetrahydrofuran as a Reagent to Sequence Cytosine and to Probe Non–Watson–Crick DNA Structures," *Nucleic Acids Research*, 23(4):713–719, 1995.

Liu, Yan–Hui, et al., "Rapid Screening of Genetic Polymorphisms Using Buccal Cell DNA with Detection by Matrix––Assisted Laser Desorption/Ionization Mass Spectrometry," *Rapid Commun. in Mass Spectrometry*, 9:735–743, 1995.

Liu, Yan–Hui, et al., "Use of a Nitrocellulose Film Substrate in Matrix–Assisted Laser Desorption–Ionization Mass Spectrometry for DNA Mapping and Screening," *Anal. Chem.*, 67:3482–3490, 1995.

Mag, et al., "Synthesis and Selective Cleavage of an Oligodeoxynucleotide Containing a Bridged Internucleotide 5'–Phosphorothioate Linkage," *Nucleic Acids Research*, 19(7):1437–1441, 1991.

Nelson, Dogruel, Williams, "Detection of Human IgM at m/z~1 Mda," *Rapid Commun. in Mass Spectrom.*, 9:7, 1995.

Newman, Nwosu, Williams, Cosstick, Seela, Connolly, "Incorporation of a Complete Set of Deoxyadenosine and Thymidine Analogues Suitable for the Study of Protein Nucleic Acid Interactions into Oligodeoxynucleotides," *Biochemistry*, 29:9891–9901, 1990.

Orita, et al., "Detection of Polymorphisms of Human DNA by Gel Electrophoresis as Single–Strand Conformation Polymorphisms," *Proc. Natl. Acad. Sci. USA,* 86:2766–2770, 1989.

Pease, et al., "Light–Generated Oligonucleotide Arrays for Rapid DNA Sequence Analysis," *Proc. Natl. Acad. Sci. USA,* 91:5022–5026, 1994.

Richterich, et al., "Cytosine Specific DNA Sequencing with Hydrogen Peroxide," *Nucleic Acids Research,* 23(23):4922–4923, 1995.

Saleeba, et al., "Chemical Cleavage of Mismatch to Detect Mutations," *Methods Enzymology,* 217:286–295, 1993.

Sandaltzopoulos and Becker "Solid–Phase DNase I Footprinting," *Biochemica,* 4:25–27, 1995.

Shaler, et al., "Effect of Impurities on the Matrix–Assisted Laser Desorption Mass Spectra of Single–Stranded Oligodeoxynucleotides," *Anal. Chem.,* 68(3):576–579, 1996.

Shaw, Madison, Sood, Spielvogel, "Oligonucleoside Boranophosphate (Borane Phosphonate)," *In: Methods in Molecular Biology, vol. 20: Protocols for Oligonucleotides and Analogs,* S. Agrawal (Ed.), Humana Press Inc., Totowa, NJ, Chapter 11, 224–243, 1993.

Soukup, Cerny, Maher III, "Preparation of Oligonucleotide—Biotin Conjugates with Cleavable Linkers," *Bioconjugate Chem.,* 6:135–138, 1995.

Spengler, et al., "Laser Mass Analysis in Biology," *Ber. Bunsenqes Phys. Chem.,* 93(3):396–402, 1989.

Szybalski, "Universal Restriction Endonucleases: Designing Novel Cleavage Specificities by Combining Adapter Oligodeoxynucleotide and Enzyme Moieties," *Gene,* 40:169–173, 1985.

Tanaka, et al., "Protein and Polymer Analyses up to m/z 100 000 by Laser Ionization Time–of–flight Mass Spectrometry," *Rapid Commun. in Mass Spectrometry,* 2:151–153, 1988.

Tang, et al., "Laser Mass Spectrometry of Polydeoxyribothymidylic Acid Mixtures," *Rapid Commun. Mass Spectrom,* 7:63–66, 1993.

Tang, et al., "Matrix–Assisted Laser Desorption/Ionization of Restriction Enzyme–Digested DNA," *Rapid Commun. in Mass Spectrometry,* 8:183–186, 1994.

Uhlmann and Peyman "Antisense Oligonucleotides: A New Therapeutic Principle," *Chemical Reviews,* 90(4):543–584, 1990.

Wang, et al., "DNA Sequencing from Single Phage Plaques Using Solid–Phase Magnetic Capture," *BioTechniques,* 18(1):130–135, 1995.

Wu, et al., "Matrix–Assisted Laser Desorption Time–of–Flight Mass Spectrometry of Oligonucleotides Using 3–Hydroxypicolinic Acid as an Ultraviolet–sensitive Matrix," *Rapid Commun. in Mass Spectrometry,* 7:142–146, 1993.

Wu, Shaler, Becker, "Time–of–Flight Mass Spectrometry of Underivatized Single–Stranded DNA Oligomers by Matrix–Assisted Laser Desorption," *Anal. Chem.,* 66:1637–1645, 1994.

Youil, et al., "Screening for Mutations by Enzyme Mismatch Cleavage with T4 Endonuclease VII," *Proc. Natl. Acad. Sci. USA,* 92:87–91, 1995.

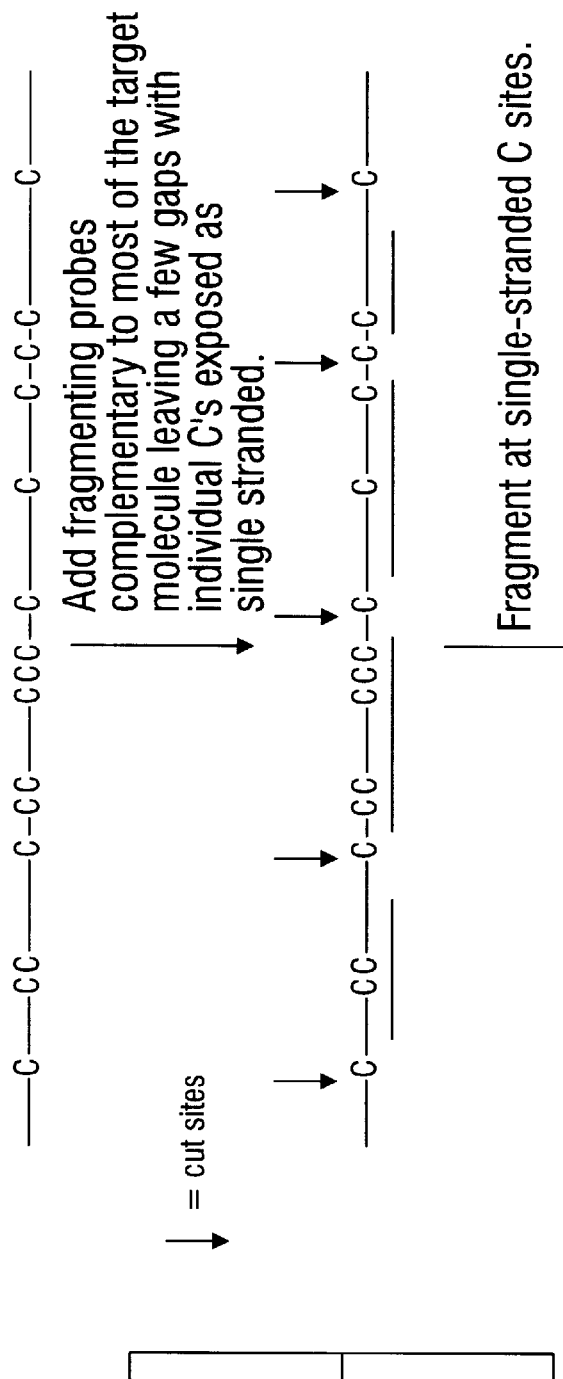
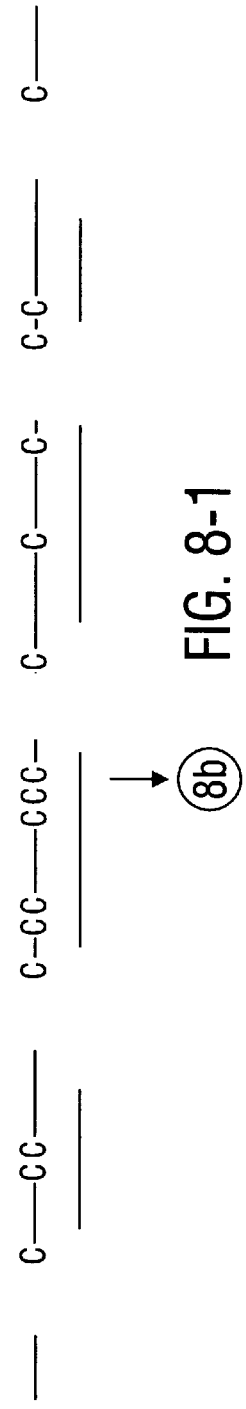
FIG. 8-1
FIG. 8-1 | FIG. 8-2
FIG. 8

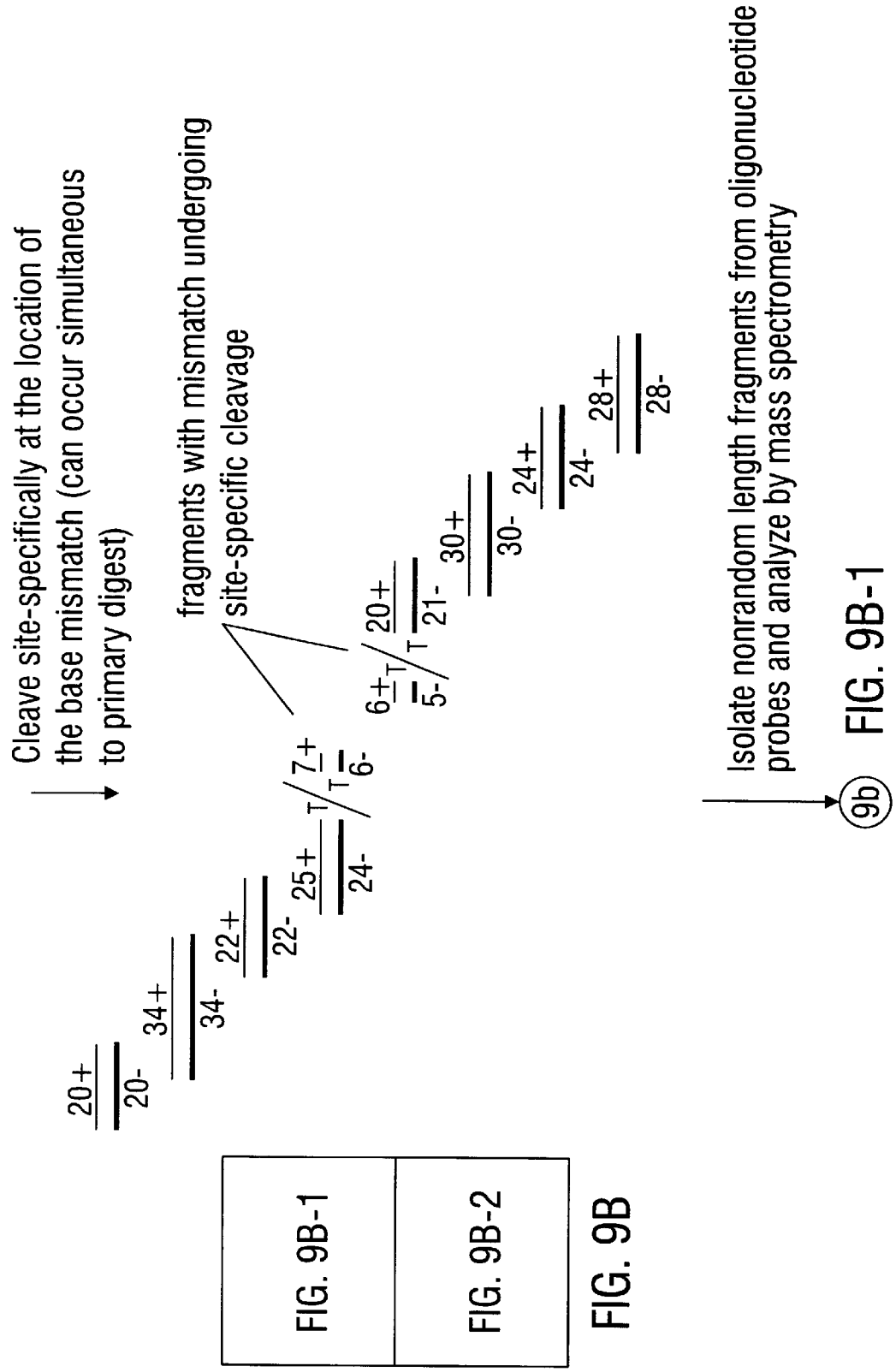

FIG. 10A-1
FIG. 10A-2
FIG. 10A
Heterozygous mix
(A) Wild type target nucleic acid
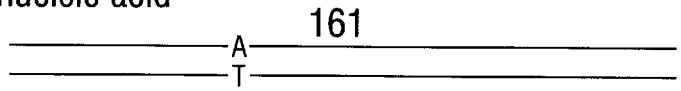
(B) Mutant target nucleic acid
(A to T transversion)
+
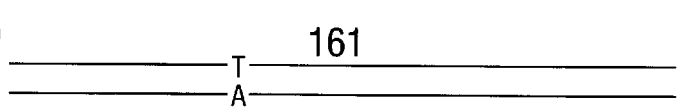
Fragment target nucleic acid using restriction endonucleases
(A) Wild type nonrandom length fragments (NLF)
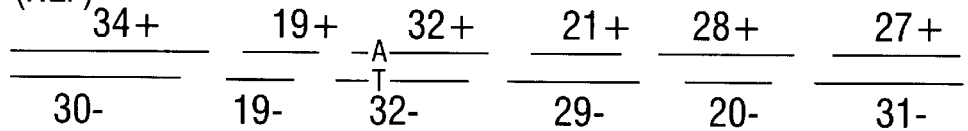
(B) Mutant NLF (A to T transversion)   +
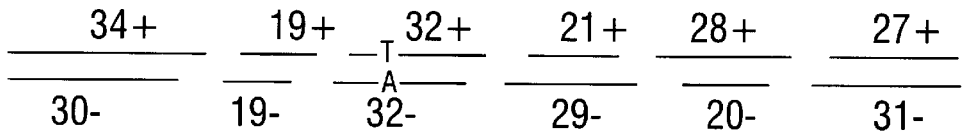
FIG. 10A-1

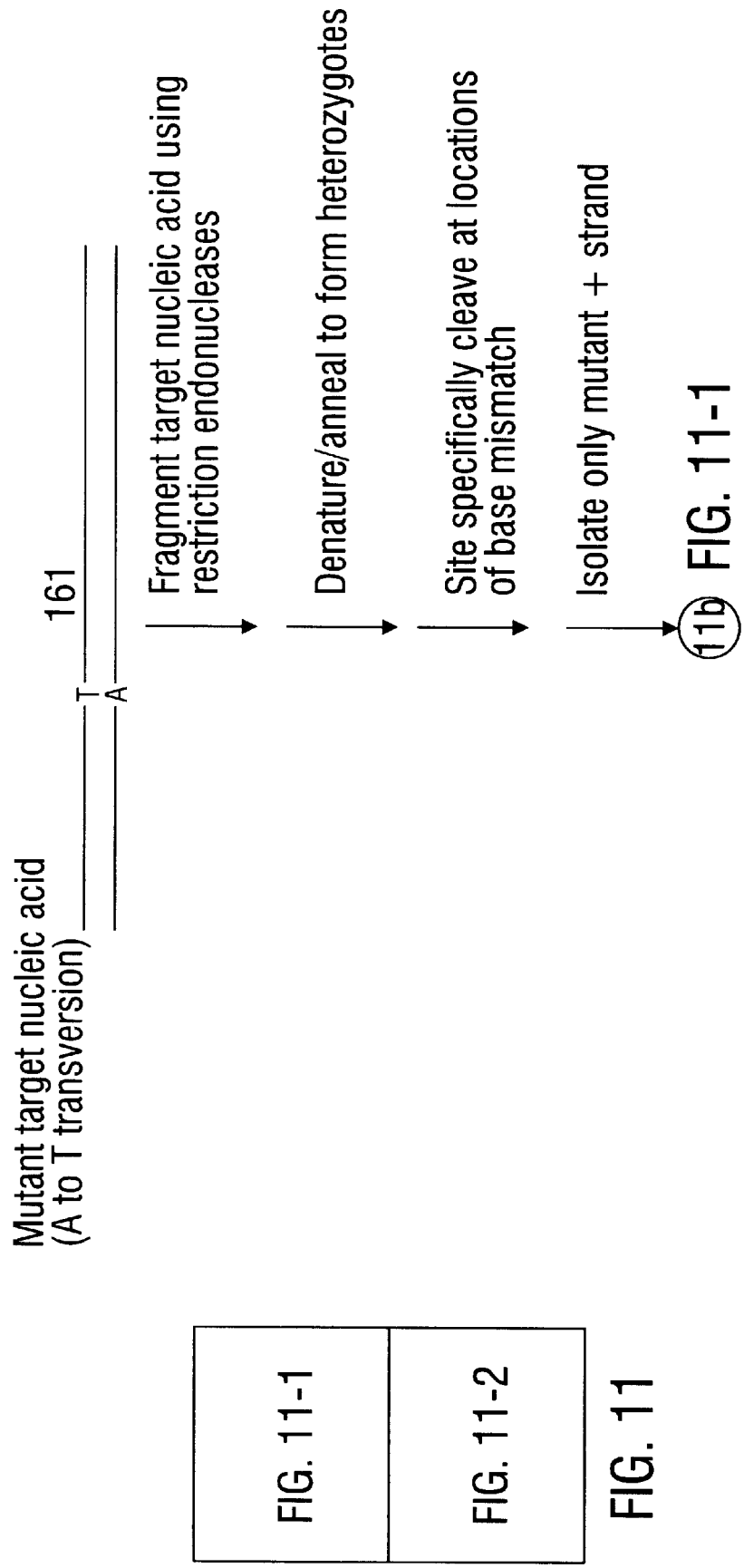

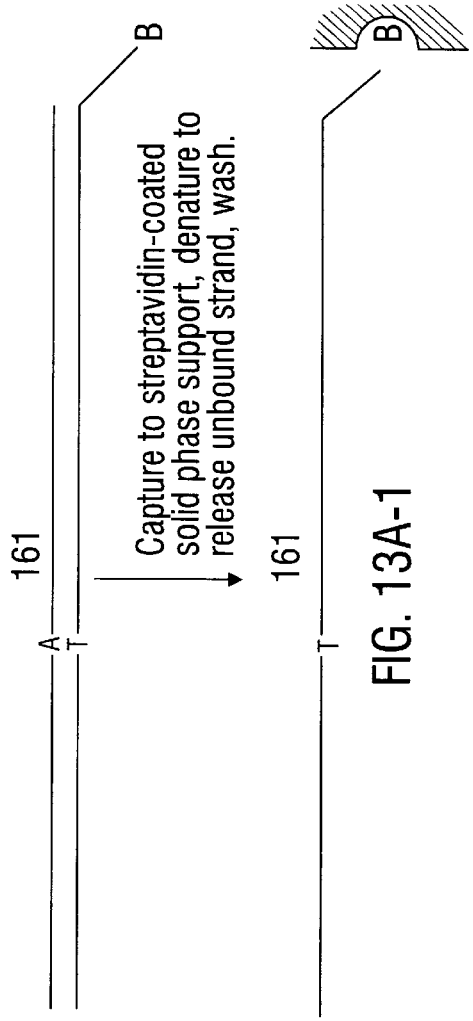
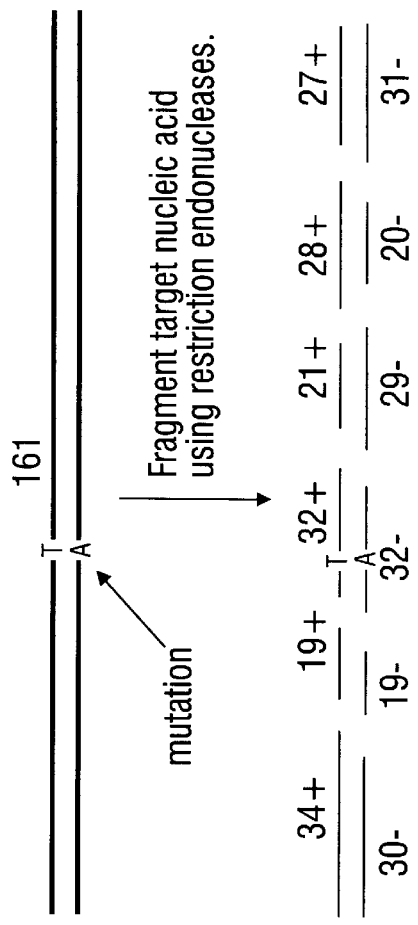

METHODS OF SCREENING NUCLEIC ACIDS USING MASS SPECTROMETRY

This application claims the benefit of U.S. Provisional Application No. 60/012,752, filed Mar. 4, 1996.

ACKNOWLEDGEMENTS

This invention was supported in part by a Financial Assistance Award from the United States Department of Commerce, Advanced Technology Program, Cooperative Agreement #70NANB5H1029. The U.S. Government may have rights in this invention.

TECHNICAL FIELD

This invention relates generally to methods for screening nucleic acids for mutations by analyzing fragmented nucleic acids using mass spectrometry.

INTRODUCTION

Approximately 4,000 human disorders are attributed to genetic causes. Hundreds of genes responsible for various disorders have been mapped, and sequence information is being accumulated rapidly. A principal goal of the Human Genome Project is to find all genes associated with each disorder. The definitive diagnostic test for any specific genetic disease (or predisposition to disease) will be the identification of mutations in affected cells that result in alterations of gene function. Furthermore, response to specific medications may depend on the presence of mutations. Developing DNA (or RNA) screening as a practical tool for medical diagnostics requires a method that is inexpensive, accurate, expeditious, and robust.

Genetic mutations can manifest themselves in several forms, such as point mutations where a single base is changed to one of the three other bases, deletions where one or more bases are removed from a nucleic acid sequence and the bases flanking the deleted sequence are directly linked to each other, and insertions where new bases are inserted at a particular point in a nucleic acid sequence adding additional length to the overall sequence. Large insertions and deletions, often the result of chromosomal recombination and rearrangement events, can lead to partial or complete loss of a gene. Of these forms of mutation, in general the most difficult type of mutation to screen for and detect is the point mutation because it represents the smallest degree of molecular change. The term mutation encompasses all the above-listed types of differences from wild type nucleic acid sequence. Wild type is a standard or reference nucleotide sequence to which variations are compared. As defined, any variation from wild type is considered a mutation including naturally occurring sequence polymorphisms.

Although a number of genetic defects can be linked to a specific single point mutation within a gene, e.g. sickle cell anemia, many are caused by a wide spectrum of different mutations throughout the gene. A typical gene that might be screened using the methods described here could be anywhere from 1,000 to 100,000 bases in length, though smaller and larger genes do exist. Of that amount of DNA, only a fraction of the base pairs actually encode the protein. These discontinuous protein coding regions are called exons and the remainder of the gene is referred to as introns. Of these two types of regions, exons often contain the most important sequences to be screened. Several complex procedures have been developed for scanning genes in order to detect mutations, which are applicable to both exons and introns.

Gel Electrophoresis: Several of the procedures described below use some form of gel electrophoresis. Therefore it is worthwhile to briefly consider this separation technology before proceeding to the specific methods. In terms of current use, most of the methods to scan or screen genes employ slab or capillary gel electrophoresis for the separation and detection step in the assays. Gel electrophoresis of nucleic acids primarily provides relative size information based on mobility through the gel matrix. If calibration standards are employed, gel electrophoresis can be used to measure absolute and relative molecular weights of large biomolecules with some moderate degree of accuracy; even then typically the accuracy is only 5% to 10%. Also the molecular weight resolution is limited. In cases where two DNA fragments with identical number of base pairs can be separated, using high concentration polyacrylamide gels, it is still not possible to identify which band on a gel corresponds to which DNA fragment without performing secondary labeling experiments. Gel electrophoresis techniques can only determine size and cannot provide any information about changes in base composition or sequence without performing more complex sequencing reactions. Gel-based techniques, for the most part, are dependent on labeling methods to visualize and discriminate between different nucleic acid fragments.

DNA Sequencing: The principal approach currently used to screen for genetic mutations is DNA sequencing. Sequencing reactions can be performed to screen the full genetic target base by base. This process, which can pinpoint the exact location and nature of mutation, requires labeling DNA, use of polyacrylamide gels, and a multiplicity of reactions to assess all bases over the length of a gene, all of which are slow and labor intensive procedures. [J. Bergh et al. "Complete Sequencing of the p 53 Gene Provides Prognostic Information in Breast Cancer Patients, Particularly in Relation to Adjuvant Systemic Therapy and Radiotherapy," Nature Medicine 1, 1029 (1995)]

For DNA sequencing, nucleic acids comprising different exons or small clusters of exons are individually amplified, often using polymerase chain reaction (PCR). The amplifications are normally performed separately although some multiplexing of reactions is possible. The amplified nucleic acids typically range from one hundred to several thousand bases in length. Following amplification, the PCR products can serve as templates for standard dideoxy-based Sanger sequencing reactions. The four different sequencing reactions are run (or for fluorescence detection, one reaction with four different dye terminators) and then analyzed by polyacrylamide gel electrophoresis. Each sequencing run yields about 300 to 600 bases of sequence which typically must be read with at least a two to three-fold redundancy in order to assure accuracy. Using slab gel, the analysis process typically takes several hours.

SSCP: The single strand conformational polymorphism assay takes advantage of structural variation within DNA that results from mutation. The method involves folding the single-stranded form of a given nucleic acid sequence into a thermodynamically directed secondary and tertiary structure. In most cases, mutated sequences form different structures than the wild type sequence, thus permitting separation of mutated and wild type sequences by gel electrophoresis. Like sequencing, this assay is complicated by the need to label molecules and run polyacrylamide gels. In a typical case, mutations can be located within a general range of 50 to 200 base pairs, but the exact nature of the mutation cannot be identified. [M. Orita et al., "Detection of Polymorphisms of Human DNA by Gel Electrophoresis as Single-Stranded Conformation Polymorphisms," Proc. Natl. Acad. Sci. USA 86, 2766 (1989)]

DGGE: Like SSCP, denaturing gradient gel electrophoresis assays also differentiate based on structural variation, but require the use of gradient gels, which are difficult to prepare. The different thermodynamic stability of structures formed by the mutant sequence, as opposed to wild type, lead to differences in the temperature and/or pH at which the molecule will denature. DGGE mutation identification and localization properties are similar to those for SSCP though sensitivity is higher for DGGE because not all mutations cause the structural changes that the SSCP method depends upon for detection. [E. S. Abrams, S. E. Murdaugh & L. S. Lerman, "Comprehensive Detection of Single Base Changes in Human Genomic DNA Using Denaturing Gradient Gel Electrophoresis and a GC Clamp," Genomics 7, 463 (1990)]

EMC: Enzyme mismatch cleavage utilizes one or more enzymes that are capable of recognizing interruptions in base pairing within a double-stranded nucleic acid molecule, e.g. base-base mismatches, bulges, or internal loops. A given length of DNA or RNA is prepared in heterozygous form, with one strand composed of wild type nucleic acid and the other strand containing a potential mutation. At the specific site where the mutation forms a mismatch with the wild type sequence, a structural perturbation occurs. An enzyme such as T4 endonuclease VII, RuvC, RNase A, or MutY, can recognize such a structural perturbation and can site-specifically cut the double-stranded nucleic acid, creating smaller molecules whose sizes indicate the presence and location of the mutation. As with the previously discussed methods, this approach as currently used, also requires labeling and gel electrophoresis. With this method, the site of mutation can be localized to within a few base pairs but the exact nature of the mutation cannot be determined. [R. Youil, B. W. Kemper & R. G. H. Cotton, "Screening for Mutations by Enzyme Mismatch Cleavage with T4 Endonuclease VII," Proc. Natl. Acad. Sci. USA 92, 87 (1995)]

CCM: A variation of EMC is to replace the enzymatic cleavage step with chemical cleavage. Chemical cleavage mismatch analysis involves the use of reagents such as osmium tetroxide to react with mismatched thymine residues or hydroxylamine to react with mismatched cytosine residues. Cleavage of the modified mismatched residues occurs when the modified bases are subsequently treated with piperidine or another oxidizing agent. The effectiveness of the method is similar to EMC. [J. A. Saleeba & R. G. H. Cotton, "Chemical Cleavage of Mismatch to Detect Mutations," Methods in Enzymology 217, 286 (1993)]

Hybridization Arrays: Several approaches to screening for mutations involve the probing of a target nucleic acid by an array of oligonucleotides that can differentiate between normal wild type nucleic acids and mutant nucleic acids. These arrays involve the performance of hundreds or thousands of hybridization reactions in parallel with different site-directed oligonucleotides and requires sophisticated and costly probe arrays. Hybridization arrays can identify the location and type of mutation in many, but not all cases. For example, semihomologous sequential insertions or targets with repeating sequences and/or repeating sequential motifs cannot be analyzed by hybridization. [A. C. Pease et al., "Light-Generated Oligonucleotide Arrays for Rapid DNA Sequence Analysis," Proc. Natl. Acad. Sci. USA 91, 5022 (1994)]

Simple screens: For mutations localized within a given gene, such as the cystic fibrosis ΔF508 deletion, it is also possible to perform a single PCR or ligase chain reaction (LCR) assay or simple hybridization assays tailored to these specific sites. PCR and LCR results are presently determined by the use of labeled molecules, where radioactive emissions, fluorescence, chemiluminescence or color changes are detected directly. These simple screens amount to a yes/no answer and do not directly identify the nature of the mutation, only whether or not a reaction took place. [P. Fang et al., "Simultaneous Analysis of Mutant and Normal Alleles for Multiple Cystic Fibrosis Mutations by the Ligase Chain Reaction," Human Mutation 6, 144 (1995)]

All of the methods in use today capable of screening broadly for genetic mutations suffer from technical complication and are labor and time intensive. There is a need for new methods that can provide cost effective and expeditious means for screening genetic material in an effort to reduce medical expenses. The inventions described here address these issues by developing novel, tailor-made processes that focus on the use of mass spectrometry as a genetic analysis tool. Mass spectrometry requires minute samples, provides extremely detailed information about the molecules being analyzed including high mass accuracy, and is easily automated.

The late 1980's saw the rise of two new mass spectrometric techniques for successfully measuring the masses of intact very large biomolecules, namely, matrix-assisted laser desorption/ionization (MALDI) time-of-flight mass spectrometry (TOF MS) [K. Tanaka et al., "Protein and Polymer Analyses up to m/z 100,000 by Laser Ionization Time-of-flight Mass Spectrometry," Rapid Commun. Mass Spectrom. 2, 151–153 (1988); B. Spengler et al., "Laser Mass Analysis in Biology," Ber. Bunsenges. Phys. Chem. 93, 396–402 (1989)] and electrospray ionization (ESI) combined with a variety of mass analyzers [J. B. Fenn et al., Science 246, 64–71 (1989)]. Both of these two methods are suitable for genetic screening tests. The MALDI mass spectrometric technique can also be used with methods other than time-of-flight, for example, magnetic sector, Fourier-Transform, ion cyclotron resonance, quadrupole, and quadrupole trap. One of the advances in MALDI analysis of polynucleotides was the discovery of 3-hydroxypicolinic acid as an ideal matrix for mixed-base oligonucleotides. Wu, et al., Rapid Comm'ns in Mass Spectrometry, 7:142–146 (1993).

MALDI-TOF MS involves laser pulses focused on a small sample plate comprising analyte molecules (nucleic acids) embedded in either a solid or liquid matrix comprising a small, highly absorbing compound. The laser pulses transfer energy to the matrix causing a microscopic ablation and concomitant ionization of the analyte molecules, producing a gaseous plume of intact, charged nucleic acids in single-stranded form. If double-stranded nucleic acids are analyzed, the MALDI-TOF MS typically results in mostly denatured single-strand detection. The ions generated by the laser pulses are accelerated to a fixed kinetic energy by a strong electric field and then pass through an electric field-free region in vacuum in which the ions travel with a velocity corresponding to their respective mass-to-charge ratios (m/z). The smaller m/z ions will travel through the vacuum region faster than the larger m/z ions thereby causing a separation. At the end of the electric field-free region, the ions collide with a detector that generates a signal as each set of ions of a particular mass-to-charge ratio strikes the detector. Usually for a given assay, 10 to 100 mass spectra resulting from individual laser pulses are summed together to make a single composite mass spectrum with an improved signal-to-noise ratio.

The mass of an ion (such as a charged nucleic acid) is measured by using its velocity to determine the mass-tocharge ratio by time-of-flight analysis. In other words, the mass of the molecule directly correlates with the time it takes to travel from the sample plate to the detector. The entire process takes only microseconds. In an automated apparatus, tens to hundreds of samples can be analyzed per minute. In addition to speed, MALDI-TOF MS has one of the largest mass ranges for mass spectrometric devices. The current mass range for MALDI-TOF MS is from 1 to 1,000,000 Daltons (Da) (measured recently for a protein). [R. W. Nelson et al., "Detection of Human IgM at m/z ~1 MDa," Rapid Commun. Mass Spectrom. 9, 625 (1995)]

The performance of a mass spectrometer is measured by its sensitivity, mass resolution and mass accuracy. Sensitivity is measured by the amount of material needed; it is generally desirable and possible with mass spectrometry to work with sample amounts in the femtomole and low picomole range. Mass resolution, m/$\Delta$m, is the measure of an instrument's ability to produce separate signals from ions of similar mass. Mass resolution is defined as the mass, m, of a ion signal divided by the full width of the signal, $\Delta$m, usually measured between points of half-maximum intensity. Mass accuracy is the measure of error in designating a mass to an ion signal. The mass accuracy is defined as the ratio of the mass assignment error divided by the mass of the ion and can be represented as a percentage.

To be able to detect any point mutation directly by MALDI-TOF mass spectrometry, one would need to resolve and accurately measure the masses of nucleic acids in which a single base change has occurred (in comparison to the wild type nucleic acid). A single base change can be a mass difference of as little as 9 Da. This value represents the difference between the two bases with the closest mass values, A and T (A=2'-deoxyadenosine-5'-phosphate=313.19 Da; T=2'-deoxythymidine-5'-phosphate=304.20 Da; G=2'-deoxyguanosine-5'-phosphate=329.21 Da; and C=2'-deoxycytidine-5'-phosphate=289.19 Da). If during the mutation process, a single A changes to T or a single T to A, the mutant nucleic acid containing the base transversion will either decrease or increase by 9 in total mass as compared to the wild type nucleic acid. For mass spectrometry to directly detect these transversions, it must therefore be able to detect a minimum mass change, $\Delta$m, of approximately 9 Da.

For example, in order to fully resolve (which may not be necessary) a point-mutated (A to T or T to A) heterozygote 50-base single-stranded DNA fragment having a mass, m, of ~15,000 Da from its corresponding wild type nucleic acid, the required mass resolution is m/$\Delta$m=15,000/9≈1,700. However, the mass accuracy needs to be significantly better than 9 Da to increase quality assurance and to prevent ambiguities where the measured mass value is near the half-way point between the two theoretical masses. For an analyte of 15,000 Da, in practice the mass accuracy needs to be $\Delta$m ~±3 Da=6 Da. In this case, the absolute mass accuracy required is (6/15,000)*100=0.04%. Often a distinguishing level of mass accuracy relative to another known peak in the spectrum is sufficient to resolve ambiguities. For example, if there is a known mass peak 1000 Da from the mass peak in question, the relative position of the unknown to the known peak may be known with greater accuracy than that provided by an absolute, previous calibration of the mass spectrometer.

In order for mass spectrometry to be a useful tool for screening for mutations in nucleic acids, several basic requirements need to be met. First, any nucleic acids to be analyzed must be purified to the extent that minimizes salt ions and other molecular contaminants that reduce the intensity and quality of the mass spectrometric signal to a point where either the signal is undetectable or unreliable, or the mass accuracy and/or resolution is below the value necessary to detect single base change mutations. Second, the size of the nucleic acids to be analyzed must be within the range of the mass spectrometry-where there is the necessary mass resolution and accuracy. Mass accuracy and resolution do significantly degrade as the mass of the analyte increases; currently this is especially significant above approximately 30,000 Da for oligonucleotides (~100 bases) Third, because all molecules within a sample are visualized during mass spectrometric analysis (i.e. it is not possible to selectively label and visualize certain molecules and not others as one can with gel electrophoresis methods) it is necessary to partition nucleic acid samples prior to analysis in order to remove unwanted nucleic acid products from the spectrum. Fourth, the mass spectrometric methods for generalized nucleic acid screening must be efficient and cost effective in order to screen a large number of nucleic acid bases in as few steps as possible.

The methods for detecting nucleic acid mutations known in the art do not satisfy these four requirements. For example, prior art methods for mass spectrometric analysis of DNA fragments have focussed on double-stranded DNA fragments which result in complicated mass spectra, making it difficult to resolve mass differences between two complementary strands. See, e.g., Tang et al., Rapid Comm'n. in Mass Spectrometry, 8:183–186 (1994).

Thus, there is a need for cost and time effective methods of detecting genetic mutations using mass spectrometry, preferably MALDI or ES, without having to sequence the genetic material and with mass accuracy of a few parts in 10,000 or better.

SUMMARY OF THE INVENTION

The present invention provides methods of and kits for detecting mutations in a target nucleic acid comprising nonrandomly fragmenting said target nucleic acid to form a set of nonrandom length fragments (NLFs), determining masses of members of said set of NLFs using mass spectrometry, wherein said determining does not involve sequencing of said target nucleic acid.

In a preferred embodiment, the method of detecting mutations comprises obtaining a set of nonrandom length fragments in single-stranded form. The masses of the members of the set of NLFs can be compared with the known or predicted masses of a set of NLFs derived from a wild type target nucleic acid that is the wild type version of the target nucleic acid that is being screened for mutations. The members of the set of single-stranded NLFs can optionally have one or more nucleotides replaced with mass-modified nucleotides, including mass-modified nucleotide analogs. Another optional aspect of the invention is the inclusion of internal calibrants or internal self-calibrants in the set of nonrandom length fragments to be analyzed by mass spectrometry to provide improved mass accuracy.

The present invention includes a number of nonrandom fragmentation techniques for nonrandomly fragmenting a target nucleic acid.

In one embodiment, the nonrandom fragmentation technique comprises hybridizing a single-stranded target nucleic acid to one or more sets of fragmenting probes to form hybrid target nucleic acid/fragmenting probe complexes comprising at least one double-stranded region and at least one single-stranded region, nonrandomly fragmenting said target nucleic acid by cleaving said hybrid target nucleic acid/fragmenting probe complexes at every single-stranded region with at least one single-strand-specific cleaving reagent to form a set of NLFs. The set of fragmenting probes can leave single-stranded regions between double-stranded regions formed by hybridization of said set of fragmenting probes to said target nucleic acid. A single-stranded region comprises a portion of a polynucleotide sequence as small as a single phosphodiester bridge, i.e. the phosphodiester bond across from a nick, to 450 nucleotides in length.

The fragmenting probes are oligonucleotides that are complementary to a nucleotide sequence of the target nucleic acid. A set of fragmenting probes can be created such that the nucleotide sequences of the members of the set of fragmenting probes represents the entire complement to the nucleotide sequence of the target nucleic acid. For example, a set of fragmenting probes can provide complete complementary sequence to the target nucleic acid. Alternatively, a set of fragmenting probes, when hybridized to the target nucleic acid, can leave single-stranded regions. Also, one or more sets of fragmenting probes can be used such that the members of one set of fragmenting probes contain nucleotide sequences that overlap With nucleotide sequences of members of a second set of fragmenting probes. In yet another aspect, there are provided two sets of fragmenting probes, where members of the second set of fragmenting probes comprise at least one single-stranded nucleotide sequence complementary to regions of said target nucleic acid that are not complementary to any nucleotide sequences in any members of said first set of fragmenting probes.

Once the set(s) of fragmenting probes are hybridized to the target nucleic acid, the single-stranded regions are cleaved using single-strand-specific cleaving reagents, including enzymatic reagents as well as chemical reagents. Single-strand specific chemical cleaving reagents include hydroxylamine, hydrogen peroxide, osmium tetroxide, and potassium permanganate.

Yet another nonrandom fragmentation technique comprises providing a single-stranded target nucleic acid, hybridizing the single-stranded target nucleic acid to one or more restriction site probes to form hybridized target nucleic acids comprising double-stranded regions where said restriction site probes have hybridized to said single-stranded target nucleic acid and at least one single-stranded region, nonrandomly fragmenting the hybridized target nucleic acids using one or more restriction endonucleases that cleave at restriction sites within the double-stranded regions. Another variation on this technique involves use of universal restriction probes comprising two regions, the first region being single-stranded and complementary to a specific site within the target nucleic acid, and the second region being double-stranded and containing the restriction recognition site for a particular class IIS restriction endonuclease. Class IIS restriction endonucleases cleave double-stranded DNA at a specific distance from their recognition site sequence.

Another technique for nonrandom fragmentation comprises fragmenting the target nucleic acid with one or more restriction endonucleases to form a set of NLFs. This and the other forms of nonrandom fragmentation can be combined with direct and indirect capture to a solid support to isolate single-stranded NLFs for mass spectrometric analysis.

Another nonrandom fragmentation technique comprises providing conditions permitting folding of said single-stranded target nucleic acid to form a three-dimensional structure having intramolecular secondary and tertiary interactions, and nonrandomly fragmenting said folded target nucleic acid with at least one structure-specific endonuclease to form a set of single-stranded NLFs. A set of nonrandom length fragments can comprise a nested set of NLFs, wherein each member of the set has a 5' end of the target nucleic acid. The structure-specific endonucleases useful for nonrandom fragmentation comprise any nucleases that cleave at structural transitions within nucleic acids, including: Holliday junctions, single-strand to double-strand transitions, or at the ends of hairpin structures.

Another nonrandom fragmentation method comprises mutation-specific cleavage by hybridizing a target nucleic acid to a set of one or more wild type probes and specifically cleaving at any regions of nucleotide mismatch or base mismatch that form between the target nucleic acid and a wild type probe. The mutation-specific cleavage can be accomplished using a mutation-specific cleaving reagent comprising structure-specific endonuclease or chemical reagents.

The nonrandom fragmentation methods described herein can be combined to form different sets or subsets of nonrandom length fragments. For example, the base mismatch nonrandom fragmentation method using wild type probes can be used in concert with a set of nonrandom length fragments that have already been creating using any one of the other nonrandom fragmentation methods. These nonrandom fragmentation methods can also be combined with isolation methods designed to isolate specific sets of single-stranded nonrandom length fragments, for example, only those NLFs derived from the+strand of the target nucleic acid. The isolation methods include direct capture of the set of NLFs to a solid support or indirect capture of a set of NLFs to a solid support via a capture probe capable of binding to a solid support via covalent or noncovalent binding. The fragmenting, wild type, restriction site, and universal restriction probes described herein can be also be used as capture probes for isolating a particular set of NLFs.

The isolation methods also comprise the use of a solution of volatile salts to wash away undesired contaminants from the set of NLFs intended for mass determination in the mass spectrometer. The volatile salts are useful for removing background noise and can be easily removed by evaporation of the volatile salts prior to mass spectrometric analysis. Volatile salt solutions can be used in a variety of different methods to prepare organic molecules such as nucleic acids and polypeptides for mass spectrometric analysis. Thus, a method is described herein of decreasing background noise, wherein the method comprises obtaining a sample to be analyzed by a mass spectrometer, washing the sample with a solution of volatile salts, and evaporating the solution of volatile salts from the sample.

The fragmentation and isolation methods separately or together can also be combined with the use of internal self-calibrants to improve the mass accuracy of the mass spectrometric analysis.

The above methods, separately or in combination, can also be combined with the use of mass-modified nucleotides and mass-modified nucleotide analogs incorporated in the target nucleic acid or a set of NLFs to improve mass resolution between mass peaks.

Kits for detecting mutations in one or more target nucleic acids in a sample are also provided. In preferred embodiments, such kits comprise one or more single-stranded target nucleic acids, one or more sets of oligonucleotide probes, wherein each of said probes is complementary to a portion of said single-stranded target nucleic acids, and various cleaving reagents, including single-strand specific cleaving reagents, restriction endonucleases (both Class II and Class IIS), and mutation-specific cleaving reagents. The oligonucleotide probes include fragmenting probes, restriction site probes, and wild type probes. Such kits can also contain a matrix, preferably 3-hydroxypicolinic acid. The kits may also contain volatile salt buffers, and buffers providing conditions suitable for the enzymatic or chemical reactions described above for nonrandomly fragmenting target nucleic acids and isolating nonrandom length fragments in preparation for mass spectrometric analysis. Additionally, the kits may contain solid supports for purposes of isolating nonrandom length fragments.

BRIEF DESCRIPTION OF THE DRAWINGS

FIGS. 1A and 1B are positive ion mass spectra obtained from 200 fmoles of DNA in 3-HPA (3-hydroxypicolinic acid). Each spectrum is a sum of 100 laser pulses at 266 nm. FIG. 1A: a single-stranded 72-mer which also shows a 71-mer. The FWHM resolution is 240, clearly resolving matrix adducts (labelled M). FIG. 1B: 88-mer parent peak has a resolution of 330.

FIG. 4A depicts a mass spectra of a heterozygous mix of wild type and mutant where A has mutated to T. Spectral peaks are separated by 9 mass units. FIG. 4B depicts a mass spectra of a heterozygous mix of wild type and mutant where A has mutated to T. T has been replaced by heptynyldeoxyuridine during amplification of the mutant region. Spectral peaks are now separated by 65 mass units.

DESCRIPTION OF SPECIFIC EMBODIMENTS

Figure 1A:
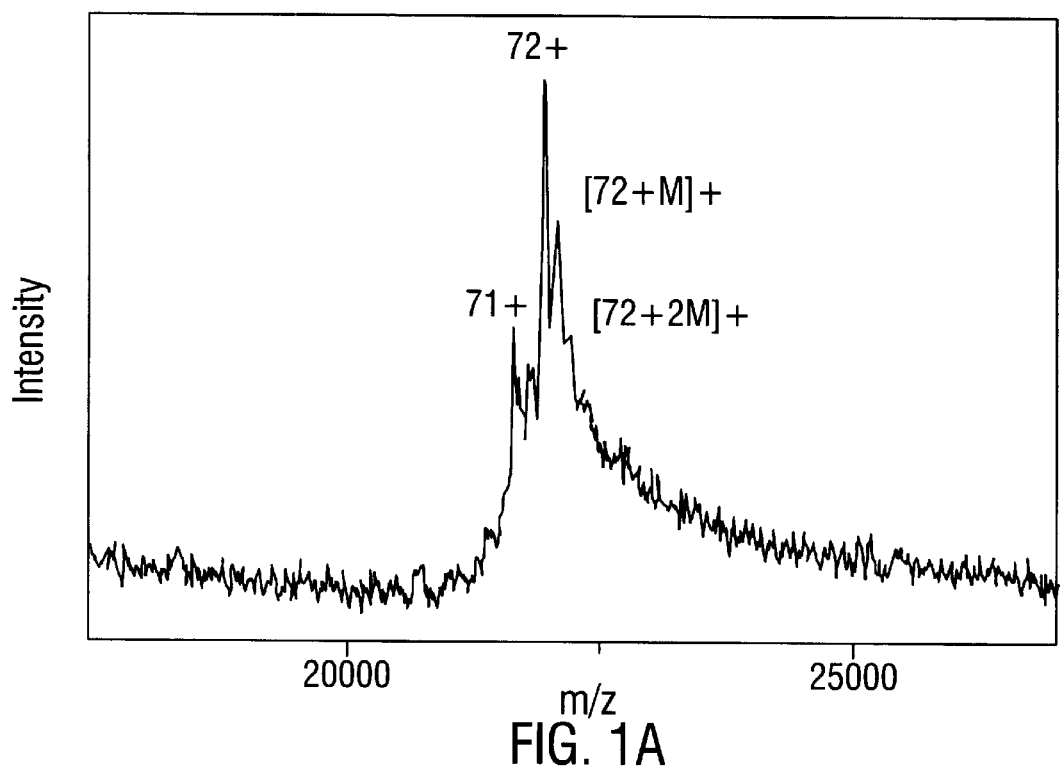
FIGS. 1A and 1B display examples of resolved nucleic acid fragments (DNA) in the 20,000 to 30,000 Da range using MALDI-TOF mass spectrometry. Both

The present invention, directed to methods of screening target nucleic acids to detect mutations using mass spectrometric techniques to analyze post-amplification nucleic acids, provides the advantages of technical ease, speed, and high sensitivity (minute samples are required). The methods described herein yield a minimal set of products with improved mass resolution and accuracy and detailed information about the nature and location of the mutation in the target nucleic acid.

The present invention involves obtaining from a target nucleic acid, using a variety of nonrandom fragmentation techniques, a set of nonrandom length fragments (NLFs) and determining the mass of the members of the set of NLFs.

The target nucleic acid can be single-stranded or double-stranded DNA, RNA or hybrids thereof, from any source, preferably from a human source, although any source which one is interested in screening for mutations can be used in the methods described herein. When the target nucleic acid is RNA, the RNA strand is the+strand. If desired, the target nucleic acid can be an RNA/DNA hybrid, wherein either strand can be designated the+strand and the other, the−strand. The target nucleic acid is generally a nucleic acid which must be screened to determine whether it contains a mutation. The corresponding target nucleic acid derived from a wild type source is referred to as a wild type target nucleic acid. The target nucleic acids can be obtained from a source sample containing nucleic acids and can be produced from the nucleic acid by PCR amplification or other amplification technique. The target nucleic acids are typically too large to analyze directly because current mass spectrometric methods do not have the mass accuracy and resolution necessary to identify a single base change in molecules larger than 100 base pairs. Accordingly, the target nucleic acids must be fragmented.

Nonrandom length fragments are nucleic acids derived by nonrandom fragmentation of a target nucleic acid, and can comprise regions or nucleotide sequences that are single-stranded or double-stranded. Due to the simpler mass spectrum that results from mass analysis of single-stranded nonrandom length fragments, it is preferred to determine the masses of sets of single-stranded nonrandom length fragments. The nonrandom length fragments can also contain mass-modified nucleotides, which can enhance ease of analysis, especially when a point mutation has resulted in a very small mass change (on the order of 9 Da) in a nonrandom length fragment as compared to the corresponding wild type nonrandom length fragment. The methods described herein use mass spectrometry to determine the masses of the set or sets of nonrandom length fragments to detect mutations in a target nucleic acid.

The nonrandom fragmentation techniques of the invention are any methods of fragmenting nucleic acids that provide a defined set of nonrandom length fragments, where that set of nonrandom length fragments may be reproducibly obtained by using the same nonrandom fragmentation method on the same target nucleic acid or its wild type version. The methods used for nonrandom fragmentation are designed to optimize the ease of analyzing the resulting mass spectral data by obtaining a range of fragment sizes that avoids significant overlap of mass peaks. The nonrandom fragmentation techniques of the invention include digestion with restriction endonucleases, structure-specific endonucleases, and specific chemical cleavage. The enzymatic nonrandom fragmentation techniques include partial digestion with restriction endonucleases or structure-specific endonucleases. Partial cleavage occurs when not every possible cleavage site is cleaved by the cleaving reagents used, whether enzymatic or chemical.

Fragmenting probes used in the invention are nucleic acids comprising a single-stranded nucleotide sequence or region that is complementary to a nucleotide sequence of a target nucleic acid. When fragmenting probes are also used as capture probes (i.e. to bind the fragmenting probe and any complementary nucleic acids hybridized thereto to a solid support), the fragmenting probes comprise a first binding moiety that is capable of binding to a second-binding moiety attached to a solid support. Upon hybridization of a set of fragmenting probes and a target nucleic acid, the hybrid can be nonrandomly fragmented using one or more cleaving reagents that specifically cleave single-stranded regions.

Restriction site probes are oligonucleotides that when hybridized to single-stranded target nucleic acid at specific complementary sequences form complete double-stranded restriction endonuclease recognition sites cleavable using the restriction endonuclease capable of cleaving at or near the recognition sites formed.

Universal restriction probes comprise two regions, the first region being single-stranded and complementary to a specific sequence within the target nucleic acid, and the second region being double-stranded and containing the restriction recognition site for a particular class IIS restriction endonuclease.

Capture probes used in the methods described herein comprise fragmenting probes, restriction site probes, universal restriction probes, and any nucleic acids that are bound to a solid support to isolate sets or subsets of nucleic acids or NLFs. Capture probes can comprise a cleavable linkage or cleavable moiety that can be selectively cleaved to release nucleic acids from a solid support prior to mass spectrometric analysis.

Wild type probes are nucleic acids derived from a wild type nucleic acid sequence comprising at least one nucleotide sequence complementary to a nucleotide sequence of a target nucleic acid or a member of a set of NLFs. Wild type probes can be restriction site probes, fragmenting probes, or capture probes comprising a wild type nucleotide sequence that when hybridized to a complementary mutation-containing region of a target nucleic acid results in a base mismatch bulge or loop structure. Wild type refers to a standard or reference nucleotide sequence to which variations are compared. As defined, any variation from wild type is considered a mutation, including naturally occurring sequence polymorphisms.

The term complementary refers to the formation of sufficient hydrogen bonding between two nucleic acids to stabilize a double-stranded nucleotide sequence formed by hybridization of the two nucleic acids.

A single-stranded region comprises a portion of a nucleotide sequence that is capable of being selectively cleaved by single-strand-specific cleaving reagents or structure-specific endonucleases, wherein the portion of a nucleotide sequence can range in size from a single phosphodiester bridge, i.e. the phosphodiester bond across from a nick, to a nucleotide sequence ranging from one to 450 nucleotides in length which are not hybridized to a complementary nucleotide sequence or region.

The types of mass spectrometry used in the invention include ESI or MALDI, wherein the MALDI method may optionally include time-of-flight. The significant multiple charging of molecules in ESI and the fact that complex mixture analysis is generally required mean that the ESI mass spectra will consist of a great many spectral peaks, possibly overlapping and causing confusion. Because the MALDI MS approach produces mass spectra with many fewer major peaks, this method is preferred.

The methods described herein do not require sequencing of the target nucleic acid (using the sequencing methods that require four different base-specific chain termination reactions to determine the complete nucleotide sequence of a nucleic acid) in order to determine the nature and presence of a mutation within the target nucleic acid.

For an initial mutation screen, a useful range of fragment sizes that will allow detection of a point mutation is around 10 to 100 bases. This size range is where mass spectrometry presently has the necessary level of mass resolution and accuracy. Thus, the fragmentation methods used in this invention are designed to produce from the target nucleic acid, a set of nonrandom length fragments ranging up to 100 bases in size. For purposes of this invention, fragmentation methods that produce a set of random length fragments are not desirable due to the limited reproducibility of such fragments, the limited information available from mass spectrometry analysis of such fragments, and the likelihood of spectral overlap from randomly generated fragments. For example, nonrandom fragmentation permits determination of the mass, base composition, and location of the set of NLFs relative to the target nucleic acid, whereas random fragmentation methods do not.

Existing mass spectrometric instrumentation in the case of MALDI-TOF MS optimally has a mass accuracy of about 1 part in 10,000 (0.01%), four times what is necessary for detecting a single base change in a 50-base long single-stranded DNA fragment. Utilization of mass-modified nucleotides (to be described later) and nearby masses as internal calibrants, provides optimal resolution and mass accuracy of larger nucleic acids, and can extend the usable mutation detection range up to 100 bases, if not higher. Continued advances in mass spectrometric instrumentation will also push this range higher.

Figure 1B:
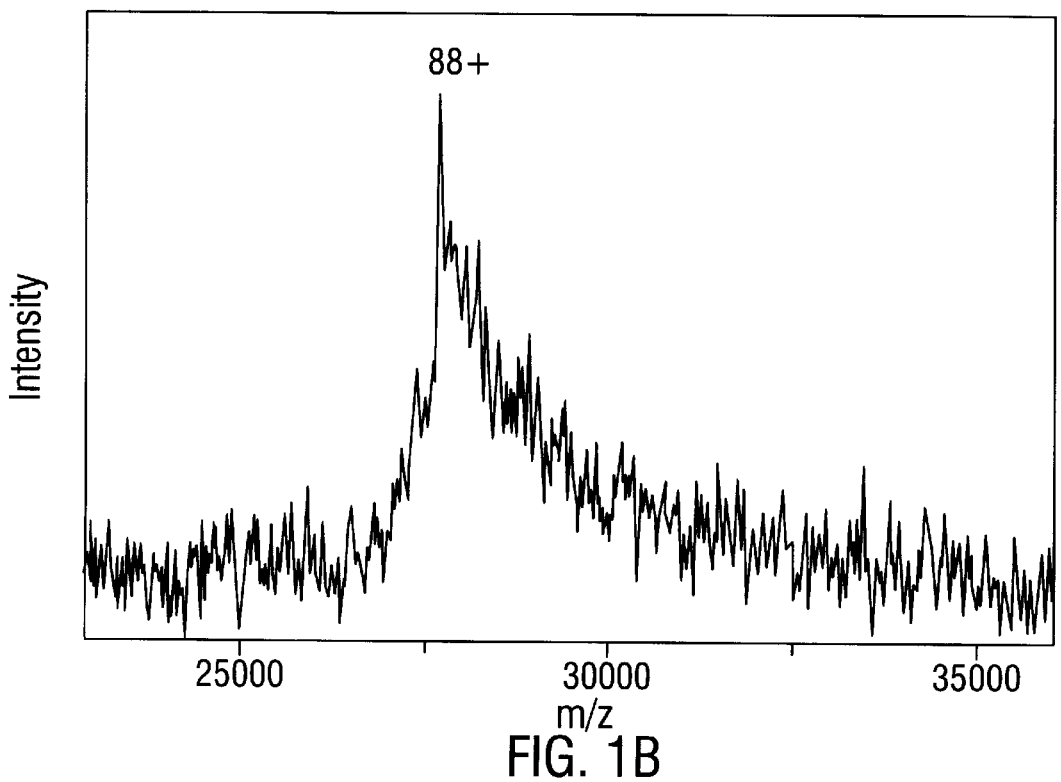
Figures 3, 13A:
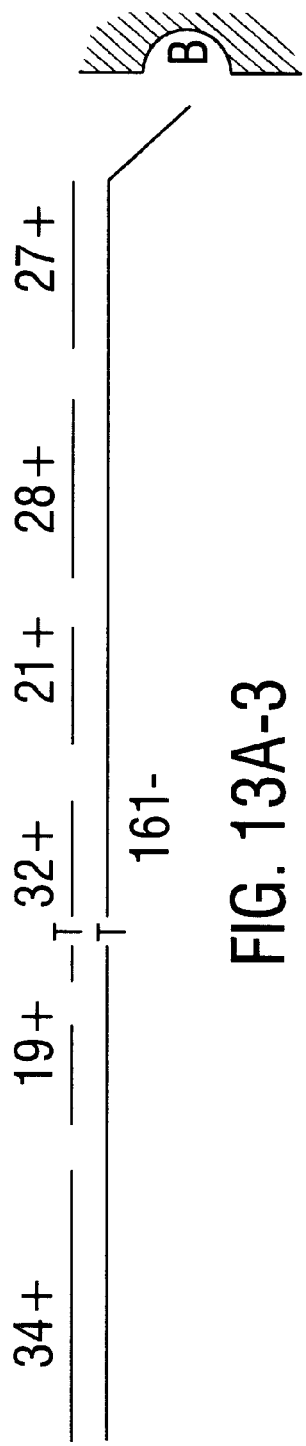
FIGS. 13A and B illustrate the use of a full length capture probe to isolate and purify a set of single-stranded nonrandom length fragments. Shown in FIG. 13B as an option is a second step involving cleavage at mutation-specific mismatch. This mismatch cleavage is particularly useful for cases where mutant DNA is hybridized to wild type.
Figures 1, 13B:
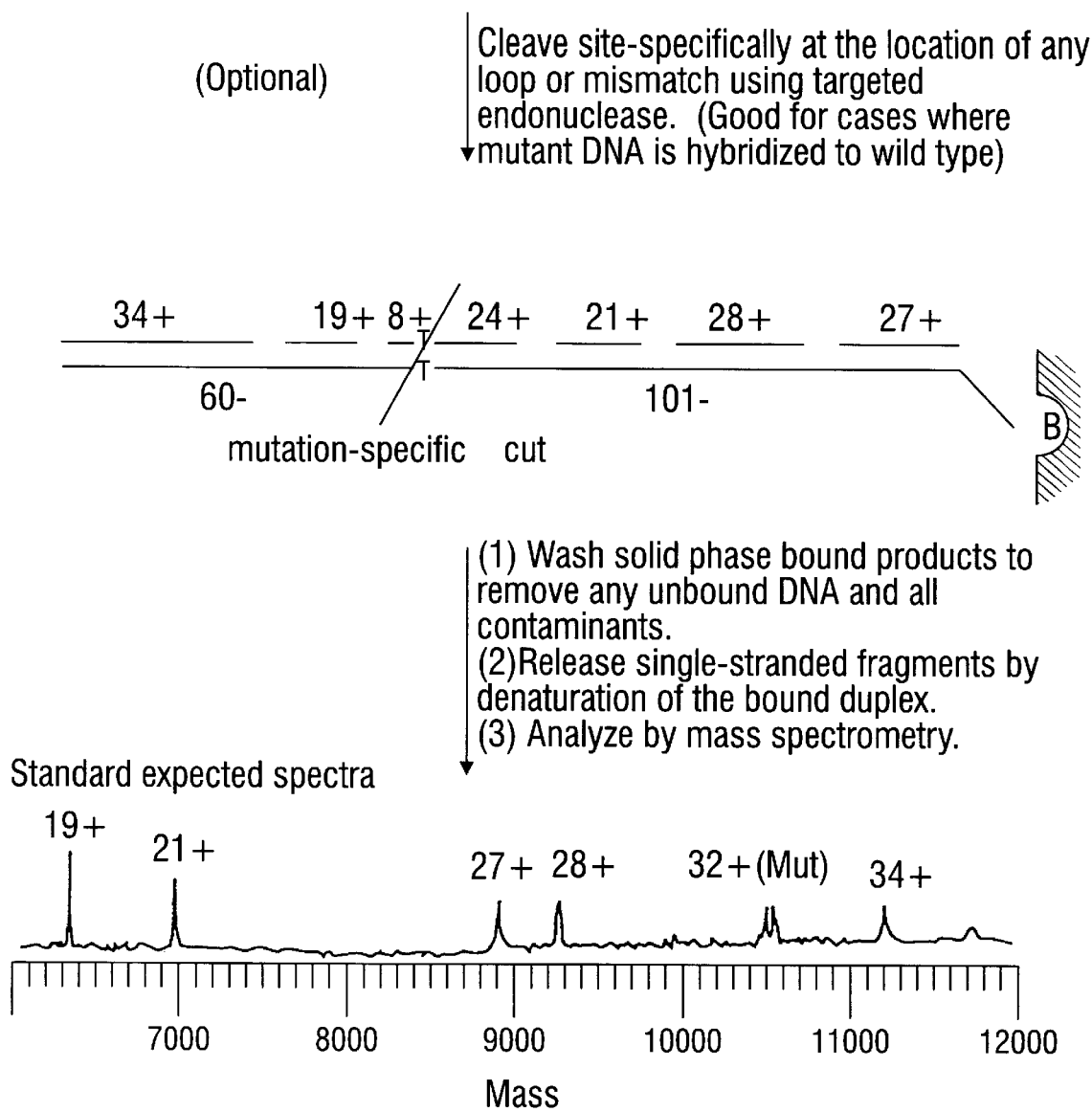

Examples of the resolving capabilities of MALDI-TOF MS are displayed in FIGS. 1A and 1B. FIG. 1 shows the positive ion TOF mass spectra obtained from 200 fmoles of DNA in the matrix 3-HPA. FIG. 1A (top figure) shows two single-stranded PCR products of lengths 71 and 72 (mass difference=305 Da=Adenosine) as well as the 72 mer and 72 mer + a single matrix adduct (M) (mass difference=139 Da) to be well resolved (FWHM resolution=240). FIG. 1B (bottom figure) shows an 88 base length single-stranded product having a resolution of 330. Both spectra display high enough accuracy and resolution to detect a point mutation if one were present.

These unique properties of mass spectrometry, MALDI-TOF MS in particular, to separate nucleic acid fragments and identify their mass exactly and the methods taught herein provide novel methods for the screening of target nucleic acids and identification of changes in base composition that might result from genetic mutation.

IMPROVING MASS ACCURACY BY INTERNAL CALIBRATION AND INTERNAL SELF-CALIBRATION

Mass spectrometers are typically calibrated using analytes of known mass. A mass spectrometer can then analyze an analyte of unknown mass with an associated mass accuracy and precision. However, the calibration, and associated mass accuracy and precision, for a given mass spectrometry system (including MALDI-TOF MS) can be significantly improved if analytes of known mass are contained within the sample containing the analyte(s) of unknown mass(es). The inclusion of these known mass analytes within the sample is referred to as use of internal calibrants. External calibrants, i.e. analytes of known mass that are not mixed in with the set of nonrandom length fragments of unknown mass and simultaneously analyzed in a mass spectrometer, are analyzed separately. External calibrants can also be used to improve mass accuracy, but because they are not analyzed simultaneously with the set of fragments of unknown mass, they will not increase mass accuracy as much as internal calibrants do. Another disadvantage of using external calibrants is that it requires an extra sample to be analyzed by the mass spectrometer. For MALDI-TOF MS, generally only two calibrant molecules are needed for complete calibration, although sometimes three or more calibrants are used. All of the embodiments of the invention described herein can be performed with the use of internal calibrants to provide improved mass accuracy.

Using the methods described herein, one can obtain a mass spectrum with numerous mass peaks corresponding to the set of nonrandom length fragments of the gene or target nucleic acid under study. If no mutation is present in the target nucleic acid, all of the mass peaks corresponding to the nonrandom length fragments will be at mass-to-charge ratios associated with the set of NLFs from the wild type target nucleic acid. However, if the target nucleic acid contains a mutation, usually no more than one or two of the mass peaks will be shifted in mass, leaving the majority of mass peaks at unaltered locations. In a preferred embodiment of the invention, a self-calibration algorithm uses these unmutated or nonpolymorphic NLFs for internal calibration to optimize the mass accuracy for analysis of the NLFs containing a mutation, thus requiring no added calibrant(s), simplifying the calibration, and avoiding potential spectral overlaps. In a given sample, however, it will not be known a priori which mass peaks, if any, are altered or shifted from their expected masses for the wild type NLFs.

The self-calibration algorithm begins by dividing up the observed mass peaks into subsets, each subset consisting of all but one or two of the observed mass peaks. Each data subset has a different one or two mass peaks deleted from consideration. For each subset, the algorithm divides the subset further into a first group of two or three masses which are then used to generate a new set of calibration constants, and a second group which will serve as an internal consistency check on those new constants. The internal consistency check begins by calculating the mass difference between the m/z values calculated for the second group of mass peaks and the values corresponding to reasonable choices for the associated wild-type NLFs. The internal consistency check can thus take the form of a chi-square minimization where the key parameter is this mass difference. The algorithm finds which data subset has the lowest sum of the squares of these mass differences resulting in a choice of optimized calibration constants associated with group one of this data subset.

After new self-optimized calibration constants are obtained, the mass-to-charge ratios are determined for the mass peaks omitted from the data subset; these are the nonrandom length fragments suspected to contain a mutation. The differences from the observed mass peaks for the wild type NLFs are then used to determine whether a mutation has occurred, and if so, what the nature of this mutation is (e.g. the exact type of deletion, insertion, or point mutation). This self-calibration procedure should yield a mass accuracy of approximately 1 part in 10,000.

FRAGMENTATION OF TARGET NUCLEIC ACIDS

Fragmentation of a target nucleic acid is important for several reasons. First, fragmentation allows direct analysis of large segments of a gene or other target nucleic acid using a single PCR amplification, eliminating the need to multiplex or run separately many smaller-segment PCR reactions.

Second, sequencing of thousands of bases of a gene or other target nucleic acid, by mass spectrometry or otherwise, is a complex and expensive process. With current capabilities in MALDI and ESI, it is impractical to sequence nucleic acids greater than 50–100 bases in length. Consequently, in order to rapidly screen large genetic regions or target nucleic acids using mass spectrometric nucleic acid sequencing, an impractical and cumbersome number of independent sequencing reactions are necessary to cover the entire genetic region of interest. Therefore, for screening large genetic regions or target nucleic acids for a wide range of potential mutations using mass spectrometry, fragmentation of amplified target nucleic acids ranging from 100 to 1000 base pairs (bp) facilitates faster screening of larger target nucleic acids or genetic regions of interest.

Sequencing can identify the exact location and nature of a genetic mutation in a target nucleic acid, but requires the use of many primers in many separate reactions. Mutations, especially for heterozygous samples analyzed using fluorescence-based systems, are often difficult to identify with confidence. Using the fragmentation methods described herein, a heterozygous sample would yield two distinct mass spectral peaks, correlating to the different masses of the mutant and wild type nucleic acids. Accordingly, the methods described herein can be used to detect a mutation in a target nucleic acid unambiguously.

Third, mass spectrometric analysis of smaller nucleic acid fragments, ranging in size from 2 to 300 bases, more preferably from 10 to 100 bases in length, is desirable because the smaller nucleic acid fragments result in:

(a) more specific localization of any mutations than for larger sized nucleic acid fragments, (b) superior mass accuracy and resolution of nucleic acid fragments in this mass range, and (c) a multiplicity of mass peaks that can be used as internal self-calibration standards, further improving the mass accuracy.

For analysis with MALDI-TOF MS, the goal of fragmentation is to produce a set of nonrandom length fragments ranging in length from 2–300 bases, preferably from 10–100 bases in length. The range of lengths serves to better separate and resolve the fragment peaks in the resulting mass spectrum.

Fragmentation of target nucleic acids larger than 100 bases in length can be accomplished using a number of means, including cleavage with one or more DNA restriction endonucleases targeting specific sequences within double-stranded DNA, chemical cleavage at structure-specific and/or base-specific locations, polymerase incorporation of modified nucleotides that create cleavage sites when incorporated, and targeted structure-specific and/or sequence-specific nuclease treatment.

An exemplary case is where a larger target nucleic acid, e.g. 500 bases in length, is nonrandomly fragmented to produce 10 to 30 nonrandom length fragments that can all be individually resolved by MALDI-TOF mass spectrometry. Two different nonrandom length fragments having the same number of bases can still be resolved from each other by mass spectrometry when they differ in base composition and consequently in mass. Gel electrophoresis methods typically cannot resolve equivalent length fragments.

For example, for a 5 kilobase pair (kb) target nucleic acid to be fully analyzed, using nonrandom length fragments with an average size of 30 bases, approximately 170 nonrandom length fragments would need to be screened. Typically, the target nucleic acid would be amplified by a number of DNA amplifications, ~10–20, in order to reduce the number of fragments to be analyzed in any given sample. Each amplified target nucleic acid product would be digested using restriction endonucleases, often with four-base recognition sites to produce the optimal size fragments. It is preferable that the fragments vary in size to simplify the mass spectral data, e.g. 32 bp+28 bp+27 bp+37 bp+ . . . , although, as stated above, nonrandom length fragments of the same size could potentially be analyzed if their base compositions vary enough to minimize spectral overlap.

Figure 2:
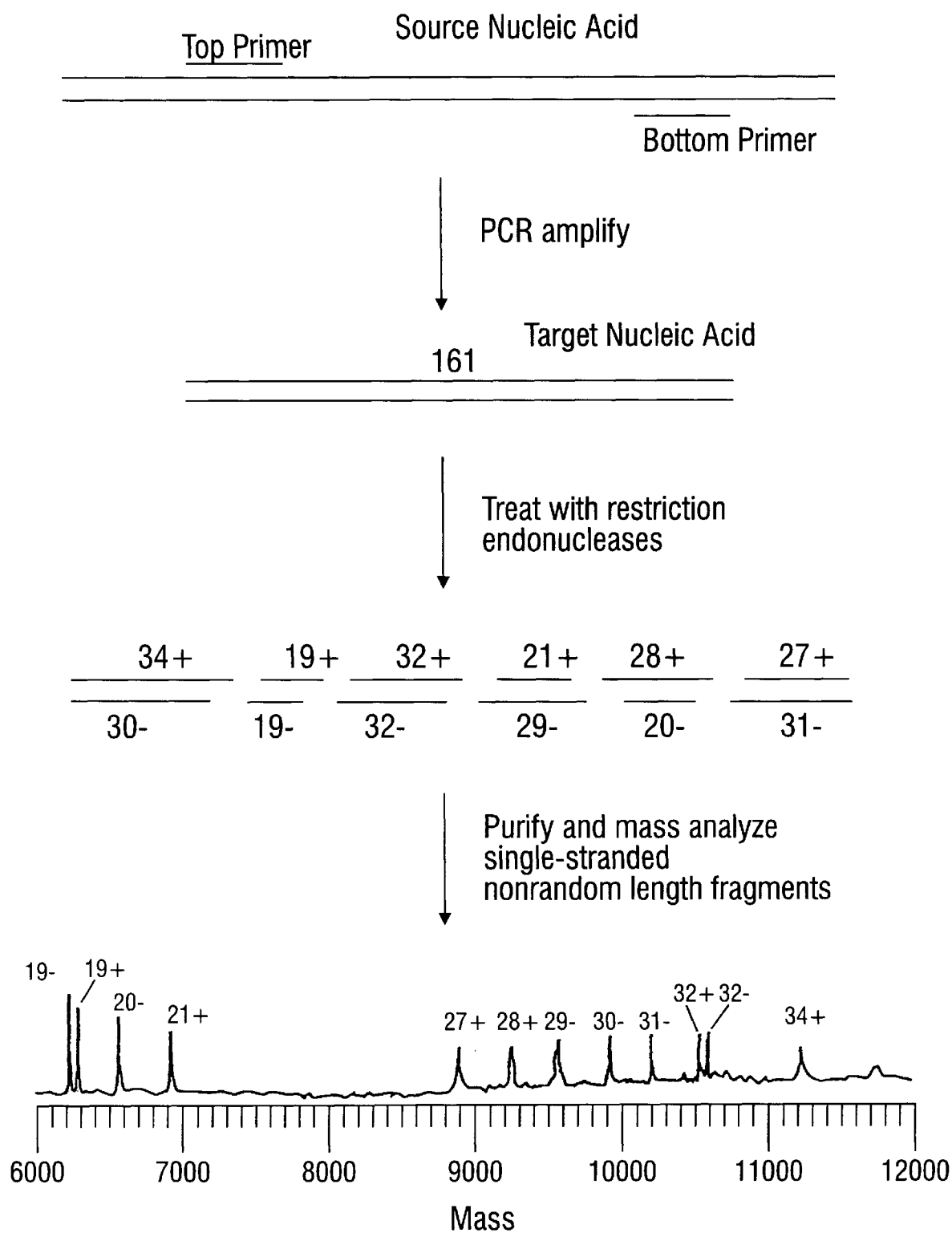
FIG. 2 is a diagram illustrating the basic steps for mass spectrometric analysis of a nonrandomly-fragmented, double-stranded target nucleic acid.

A schematic of the process along with a hypothetical mass spectrum is shown in FIG. 2. FIG. 2 illustrates a 161 base target nucleic acid that has been PCR amplified and fragmented using restriction endonucleases. The resulting 6 nonrandom length fragments are produced. When the laser desorption process occurs, during MALDI-TOF mass spectrometric analysis, the 6 double-stranded fragments are mostly denatured and the resulting 12 single-stranded nonrandom length fragments are ionized and detected. Shown at the bottom of FIG. 2 is a simulated mass spectral data plot with all the mass peaks resolved.

As can be seen in FIG. 2 it is very common that restriction endonuclease treatment will produce a number of complementary fragments with the same number of bases, e.g. two at 19 and two at 32. The presence of these equal-length fragments places higher constraints on the required resolution for distinguishing all of the different peaks. It is also not uncommon for the two equal-length, complementary fragments to have identical or nearly identical mass values, leaving the possibility that two complementary fragments will not be resolvable.

Figure 3:
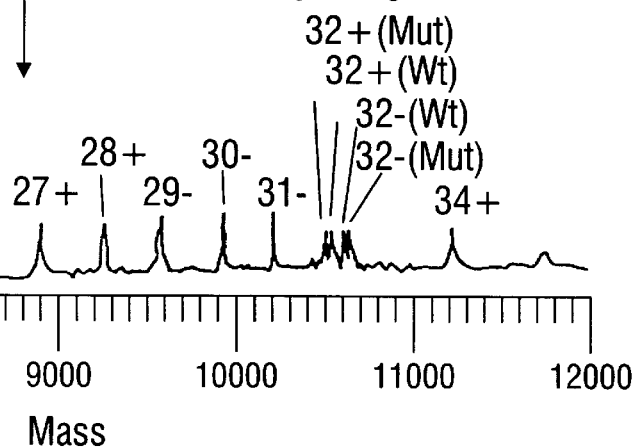
FIG. 3 is a diagram illustrating the expected mass spectrum for a nonrandomly-fragmented double-stranded target nucleic acid that is a heterozygous mix of wild type and mutant nucleic acid where the mutation is an A to T transversion.

Often samples will be heterozygous, containing a 50% mixture of both the normal wild type nucleic acid and the mutated target nucleic acid. In the case where the target nucleic acid carries a mutation in a heterozygous mix, one would observe a splitting of peaks within the nonrandom length fragments containing the mutation. An example of this splitting is shown in FIG. 3 where an A-T to T-A transversion or base flip has occurred in one copy of the gene. The expected peaks would be half normal height since their concentrations are halved relative to homozygous concentrations. In this case, the difference between mutant and wild type peaks would be ~9 Da which can be resolved in the 32 base long fragment. The presence of wild type peaks provides internal self-calibrants allowing highly accurate mass differences (as opposed to absolute mass) to be used to determine the base composition change.

The methods described herein permit MALDI-TOF MS analysis of nonrandom length fragments which has a mass accuracy of approximately 1 part in 10,000. The use of internal self-calibrants makes it possible to extend this level of accuracy up to and potentially beyond 30,000 Da or 100 bases. This mass accuracy enables exact sizing of nucleic acid fragments and the determination of the presence and nature of any mutation, including point mutations, insertions and deletions, even in a heterozygous environment. Further described herein are methods for improving the resolution of individual fragments by means including elimination of equal-length complementary pairs through the use single-strand-targeted fragmentation and/or isolation procedures, and the incorporation of mass-modified nucleotides to enhance the mass difference between similar sized fragments and/or mutant and wild type fragments. In addition, these methods provide for the removal of salts and other deleterious materials as well as a means for the removal of unwanted nucleic acid fragments prior to mass spectroscopic analysis.

MASS RESOLUTION, MASS ACCURACY, AND THE USE OF MASS-MODIFIED NUCLEOTIDES

Any of the embodiments of the invention described herein optionally include nonrandom length fragments having one or more nucleotides replaced with mass-modified nucleotides, wherein said mass-modified nucleotides comprise nucleotides or nucleotide analogs having modifications that change their mass relative to the nucleotides that they replace. The mass-modified nucleotides incorporated into the nonrandom length fragments of the invention must be amenable to the enzymatic and nonenzymatic processes used for the production of nonrandom length fragments. For example, the mass-modified nucleotides must be able to be incorporated by DNA or RNA polymerase during amplification of the target nucleic acid. Moreover, the mass-modified nucleotides must not inhibit the processes used to produce nonrandom length fragments, including, inter alia, specific cleavage by restriction endonucleases or structure-specific endonucleases and digestion by single-strand specific endonucleases, whenever such steps are used. Mass-modifications can also be incorporated in the nonrandom length fragments of the invention after the enzymatic steps have been concluded. For example, a number of small chemicals can react to modify specific bases, such as kethoxal or formaldehyde.

Any or all of the nucleotides in the nonrandom length fragments can be mass-modified, if necessary, to increase the spread between their masses. It has been shown that modifications at the C5 position in pyrimidines or the N7 position in purines do not prevent their incorporation into growing nucleic acid chains by DNA or RNA polymerase. [L. Lee et al. "DNA Sequencing with Dye-Labeled Terminators and T7 DNA Polymerase: Effect of Dyes and dNTPs on Incorporation of Dye-Terminators and Probability Analysis of Termination Fragments" Nuc. Acids. Res. 20, 2471 (1992)] For example, an octynyl moiety can be used in place of methyl on thymidine to alter the mass by 94 Da.

Mass-modifying groups can be, for example, halogen, alkyl, ester or polyester, ether or polyether, or of the general type XR, wherein X is a linking group and R is a mass-modifying group. The mass-modifying group can be used to introduce defined mass increments into the nonrandom length fragments. One of skill in the art will recognize that there are numerous possibilities for mass-modifications useful in modifying nucleic acid fragments or oligonucleotides, including those described in Oligonucleotides and Analogues: A Practical Approach, Eckstein ed. (Oxford 1991) and in PCT/US94/00193, which are both incorporated herein by reference.

Figure 4A:
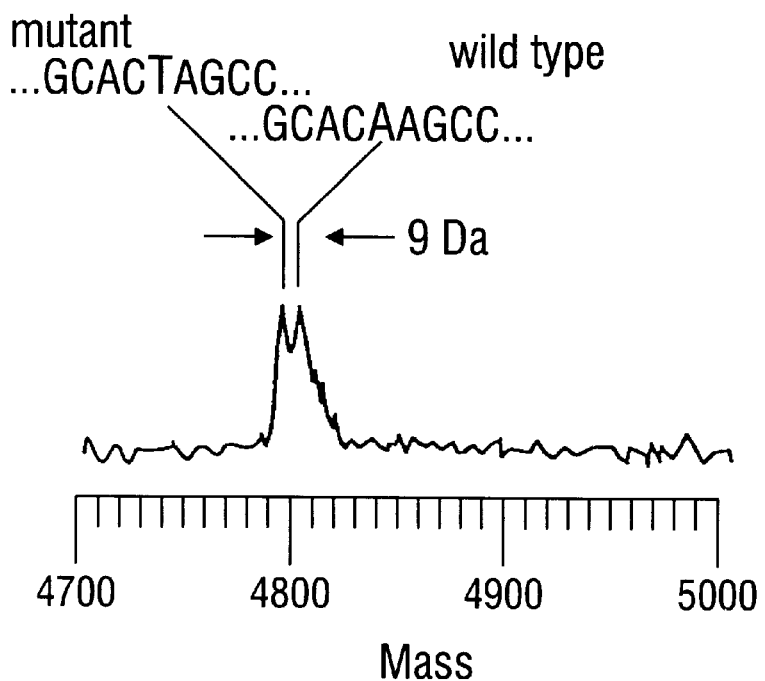
FIGS. 4A and 4B illustrate the effect on mass resolution of a mass-substituted base where a T has been replaced by heptynyldeoxyuridine during amplification of the mutant region.
Figure 4B:
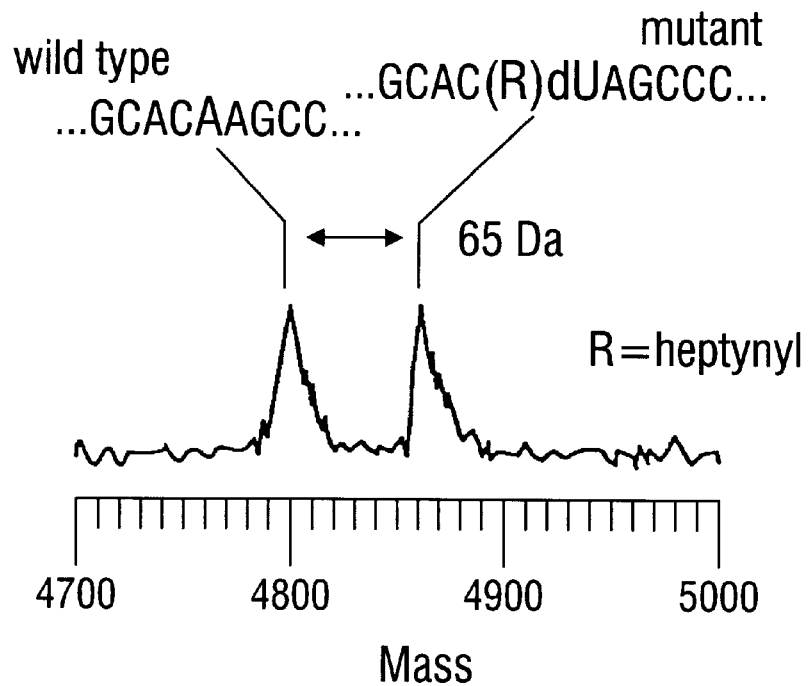

At larger mass ranges (30,000–90,000 Da), the mass resolution and mass accuracy of current MALDI-TOF mass spectrometers will not be sufficient to identify a single base change. For this reason, it may be preferable to increase the useful mass range artificially by substituting standard nucleotides within either a target nucleic acid or a nonrandom length fragment with mass-modified nucleotides having significantly larger mass differentials. Use of mass-modified nucleotides applies as well to the mass range below 30,000 Da. Mass modification can generally increase the quality of the mass spectra by enlarging the mass differences between NLFs of similar size and composition. For example, mass-modified nucleotides can increase the minimum mass difference between two nonrandom length fragments that are identical in base composition except for a single base which is an A in one NLF and is a T in the other. Normally, these two NLFs will differ in mass by only 9 Da. By incorporating a single mass-modified nucleotide into one of the bases, the mass difference can be >20 Da. The spectra in FIG. 4 depict the influence mass-modified nucleotides can have on fragment resolution. One example of the many possible mass modifications useful in this invention is the use of 5-(2-heptynyl)-deoxyuridine in place of thymidine. The replacement of a methyl group by heptynyl changes the mass of this particular nucleotide by 65 Da. An A to T transversion in a nucleic acid fragment in which all thymidine bases have been replaced with 5-(2-heptynyl)-deoxyuridine would produce a peak shift of 56 Da as opposed to 9 Da for the same nucleic acid fragments without the mass-modified nucleotides. The use of mass-modified nucleotides is especially important in the analysis of NLFs derived from RNA. Normally, the masses of C and U vary by only 1 Da, making it practically impossible to detect C to U or U to C point mutations within a given fragment.

BENEFITS OF ANALYZING SINGLE-STRANDED NUCLEIC ACIDS

The goal of this invention is the accurate determination of the masses of a set of resolved nonrandom length fragments and correlation of this data to the characterization of any mutation, if present. The embodiments of this invention include mass spectrometric determination of masses of the members of a set of single-stranded nonrandom length fragments as well as mass determination of the members of a set of mass-modified, double-stranded nonrandom length fragments. The preferred embodiment is to detect mutations in a target nucleic acid comprising obtaining a set of nonrandom length fragments in single-stranded form, wherein the single-stranded nonrandom length fragments are derived from one of either the positive or the negative strand of the target nucleic acid or where the set is a subset of fragments derived from both the positive and the negative strands of the target nucleic acid. The examples of single-stranded methods described herein focus on fragments derived from the positive strand.

FIGS. 2 and 3 illustrate that each double-stranded nonrandom length fragment, comprising two complementary strands, produces two peaks in the mass spectrum corresponding to the denatured single strands. The additional peaks from double-stranded nonrandom length fragments as compared to single-stranded nonrandom length fragments add to congestion of mass peaks in the mass spectra, as well as introducing the possibility that it may be extremely difficult, if not impossible, to resolve the complementary fragments if they have nearly or exactly identical base compositions. Furthermore, some portion of the double-stranded nonrandom length fragments do not fully denature, and mass peaks corresponding to the double-stranded products increase the spectral congestion.

Because spectra using both strands contain a two-fold redundancy in data, since any mutation in one strand will be present within its complement, it is reasonable to remove one strand prior to mass spectrometric analysis and still produce all of the data necessary for complete mutation analysis. For these reasons, it is the preferred embodiment to analyze a set of single strands where only one of the two complementary sets nucleic acid fragments representing the full target sequence is used.

Figure 5:
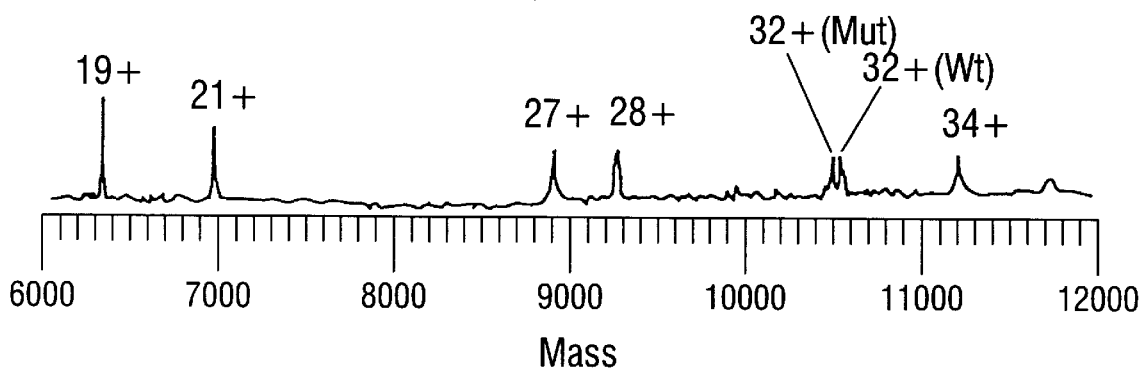
FIG. 5 is a diagram illustrating the affect of analyzing only positive strand fragments from a heterozygous sample in reducing the number of total fragments and simplifying the mass spectrum.

FIG. 5 shows the expected spectrum if only the nonrandomly fragmented positive strand of a target nucleic acid from FIG. 3 is analyzed by mass spectrometry. Analysis of one of the two complementary strands of the double-stranded nonrandom length fragments halves the number of expected peaks within the mass spectra, allowing more total fragments to be resolved and the possibility that longer total sized target nucleic acids can be analyzed at one time. Removal of one of the two strands from each nonrandom length fragment eliminates the greatest source of complication for each spectra. A number of methods for isolating and preparing both single-stranded and double-stranded nonrandom length fragments for mass spectrometry are described herein.

METHODS OF NONRANDOM FRAGMENTATION OF TARGET NUCLEIC ACIDS

The methods of the invention all involve obtaining from a target nucleic acid a set of resolvable, nonrandom-length fragments and determining the mass of the members of that set using mass spectrometry without sequencing the target nucleic acid. All of the methods described herein involving mass spectrometry include inter alia two types of mass spectrometry, electrospray ionization (ESI) and matrix-assisted laser desorption/ionization time-of-flight (MALDI-TOF). In addition to the restriction endonuclease approach to nonrandomly fragmenting a target nucleic acid, there are a number of other approaches which are described below.

NONRANDOM FRAGMENTATION USING RESTRICTION SITE PROBES

Figure 6:
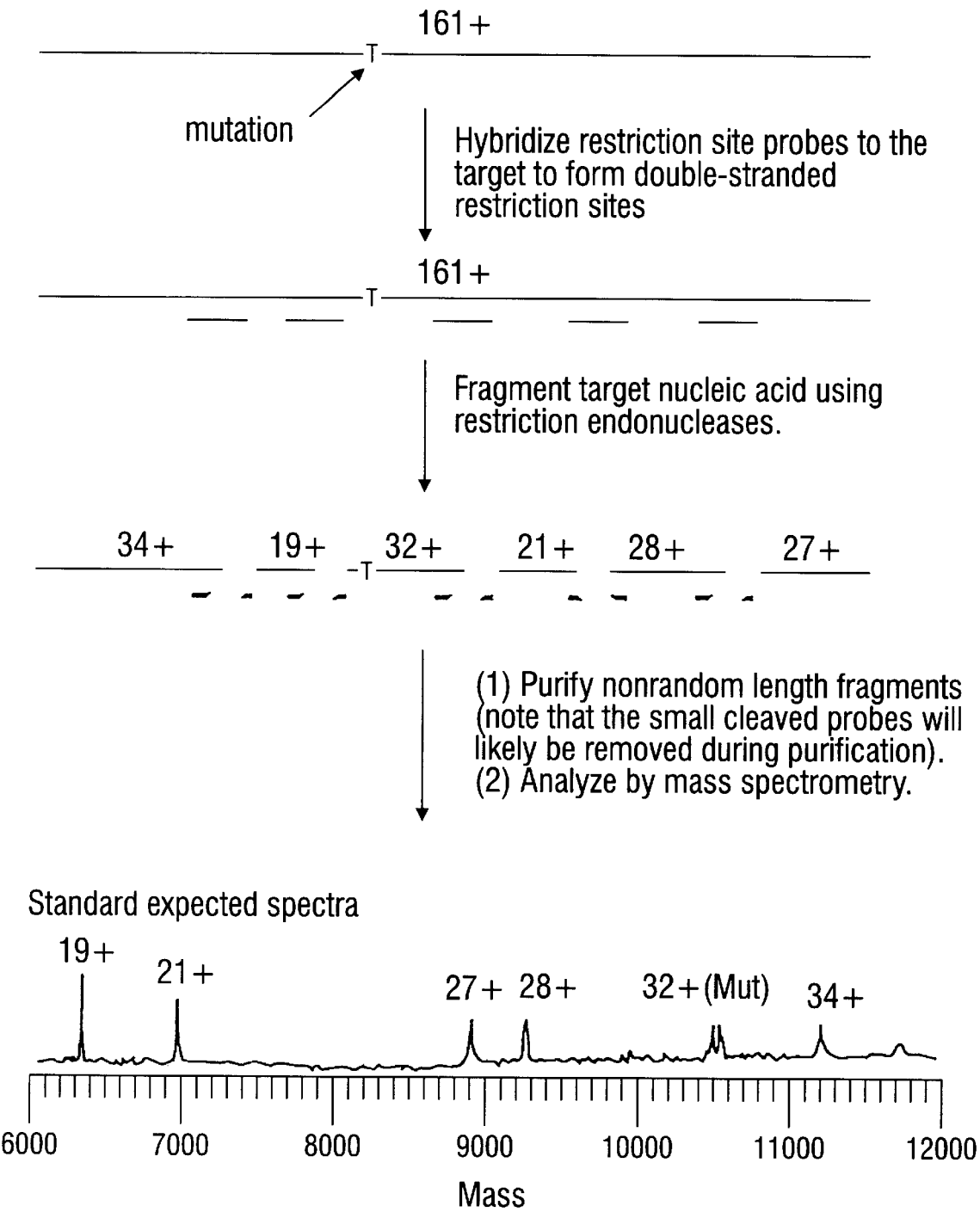
FIG. 6 is a diagram illustrating the use of restriction site probes to produce nonrandom fragments from single-stranded target nucleic acid. Note that in the step of purifying nonrandom length fragments, the small cleaved probes will likely be removed during purification.

Target nucleic acid can be nonrandomly fragmented using hybridization to nucleic acid, restriction site probes followed by cleavage with one or more restriction endonucleases the recognition sequences of which are contained in the restriction site probes used. "Restriction site probes" are oligonucleotides that when hybridized to single-stranded target nucleic acid at specific sequences form a complete double-stranded recognition site cleavable using restriction endonucleases. The use of restriction site probes is illustrated in FIG. 6.

The sequence of a wild type target nucleic acid can be analyzed to determine which restriction sites would result in an ideal spread of members of a set of NLFs. The restriction site probes are then made using well-known synthetic techniques. The restriction site probes can range from 6–100 nucleotides in length, preferably from 10–30 nucleotides in length. One advantage of using very short restriction site probes is that after cleavage with the selected restriction endonucleases, the mass of the members of the set of NLFs having cleaved restriction site probes attached can be directly determined in the mass spectrometer without requiring an isolating step to remove the cleaved restriction site probes. On the other hand, if the cleaved restriction site probes are intended to be used also as capture probes, then the restriction site probes must either have a first binding moiety that is capable of binding to a second binding moiety attached to a solid support or the restriction site probes must have at least one additional nucleotide sequence that is complementary to another probe that is bound to a solid support. A "capture probe" is an oligonucleotide that comprises a portion capable of hybridizing to a nucleic acid, such as a target nucleic acid or a nonrandom length fragment, and a binding moiety that binds the capture probe to a solid phase, either through covalent binding or affinity binding, or a mixture thereof. A capture probe can itself bind to a solid support via binding moieties (direct capture) or can bind to a solid support via another capture probe that binds to a solid support (indirect capture). Also, when the restriction site probe is also used as a capture probe, the preferred range is from 30–50 nucleotides in length, to stabilize the hybridization of the capture probe. By using larger restriction site probes complementary to singular locations on the target nucleic acid it is possible to prevent a restriction enzyme from cutting at all possible locations in a target nucleic acid where restriction sites for a particular restriction endonuclease appear, e.g. cutting at only 5 or 10 restriction sites within a single-stranded target. This is another tool that can be used to produce the optimal nonrandom length fragment set or subset.

An alternative form of restriction site probe is the universal restriction probe as described by Szybalski. [W. Szybalski "Universal Restriction Endonucleases: Designing Novel Cleavage Specificities by Combining Adapter Oligodeoxynucleotide and Enzyme Moieties," Gene 40, 169 (1985) (incorporated by reference herein)] These universal restriction probes comprise two regions, the first region being single-stranded and complementary to a specific sequence within the target nucleic acid, and the second region being double-stranded and containing the restriction recognition site for a particular class IIS restriction endonuclease. Class IIS restriction endonucleases cleave double-stranded DNA at a specific distance from their recognition sequence. By using this property, and the universal restriction site probe design, it is possible to nonrandomly fragment a single-stranded DNA target at virtually any sequence, providing the means to better control the selection of fragment sizes. It is also possible to mix standard restriction site probes and universal restriction probes in a single reaction.

In this approach, a positive single-stranded target nucleic acid is hybridized to one or more restriction site probes that are complementary to one or more restriction endonuclease recognition sequences within the target nucleic acid. Upon hybridization of the restriction site probes to the target nucleic acid, hybridized target nucleic acids are formed, comprising double-stranded regions where the restriction site probes have hybridized to the target nucleic acid and at least one single-stranded region where the target nucleic acid remains unhybridized to a restriction site probe. The double-stranded regions of the hybridized target nucleic acids are recognition sites for cleavage by one, two or more restriction endonucleases. After the formation of hybridized target nucleic acids, the hybridized target nucleic acids are digested with one, two or more restriction endonucleases, the recognition sequences of which are contained within the double-stranded regions.

The resulting nonrandom length fragments have at least one cleaved restriction site oligonucleotide probe annealed. In some cases, these cleaved probes will be of a size too small to remain hybridized to the target fragments. These nonrandom length fragments can either be purified with the cleaved restriction site oligonucleotide probes attached, or the NLFs can be purified from the cleaved oligonucleotide restriction site probes. Both types of purification can be accomplished using a variety of techniques known in the art, including filtration, precipitation, or dialysis. The preferred approach is to capture the NLFs to a solid support. The set of nonrandom length fragments can be directly captured to a solid support themselves using a number of means including a binding moiety such as biotin incorporated at numerous base positions throughout the NLFs. Or the NLFs can be indirectly captured to a solid support via hybridization to one or more capture probes that is itself bound to a solid support. The capture probe can comprise the full-length strand of the target nucleic acid that is complementary to the strand from which the nonrandom length fragments were derived. Alternatively, the capture probes can be a set of capture probes each containing at least one sequence complementary to said nonrandom length fragments.

By combining an asymmetric amplification method to produce single-stranded target nucleic acids with the use of restriction site probes, as described herein, one can produce predominantly the desired set of single-stranded NLFs. The restriction site probes used to produce the recognition sites may copurify with the NLFs but can be designed so that they do not interfere with the majority of the mass spectra. For example, the restriction site probes can be designed so that after cleavage their final sizes are less than 20 bases in length and the nonrandom length fragments can have sizes in the range of 20 to 100 bases.

The methods described above can also be modified with the use of uncleavable restriction probes. These uncleavable probes, synthesized with a restriction endonuclease resistant backbone such as phosphorothioate, boranophosphate, or methyl phosphonate, can be used to keep the target nucleic acid NLFs tethered together following restriction digest and can provide a different approach to purification of the NLFs.

FRAGMENTATION USING FRAGMENTING PROBES AND SINGLE-STRAND-SPECIFIC CLEAVAGE

While the use of restriction endonucleases in various combinations and in multiple digests can be an effective approach to fragmentation of the target nucleic acid, when a target presents long sequence lengths (>100 bases) that do not contain any restriction sites, alternative nonrandom fragmentation techniques are preferred. Long >100 base fragments will be difficult to probe with sufficient mass accuracy to determine if a base change mutation has occurred. One way to control the size of fragments is through the use of fragmenting probes and single-strand-specific endonucleases.

Fragmenting probes are defined as nonrandom length, single-stranded oligonucleotides complementary to selected regions of a single-stranded target nucleic acid, and are used through hybridization to defame and differentiate within the target nucleic acid regions that are double-stranded versus regions that remains single-stranded. Following differentiation by hybridization the single-stranded regions are subjected to cleavage. As is the case for all of the methods described here that utilize oligonucleotides, the fragmenting probes may be comprised on DNA, RNA or modified forms of nucleic acid such as phosphorothioates, methyl phosphonates or peptide nucleic acids. Three examples of single-strand-specific nucleases that can be used in these methods are Mung bean nuclease, Nuclease S1, and RNase A. These enzymes cut single-stranded DNA or RNA exclusively and act as both exo- and endonucleases.

An example of how these probes and enzymes are used follows. A set of fragmenting probes of defined size and sequence are designed to hybridize to complementary regions of the target nucleic acid. It is preferable that the target nucleic acid be primarily if not entirely single-stranded. Use of a T7 or SP6 RNA polymerase transcription system for final amplification is a simple approach to producing the required single-stranded target nucleic acid. Asymmetric PCR can also be utilized to produce primarily single-stranded target.

Figure 7A:
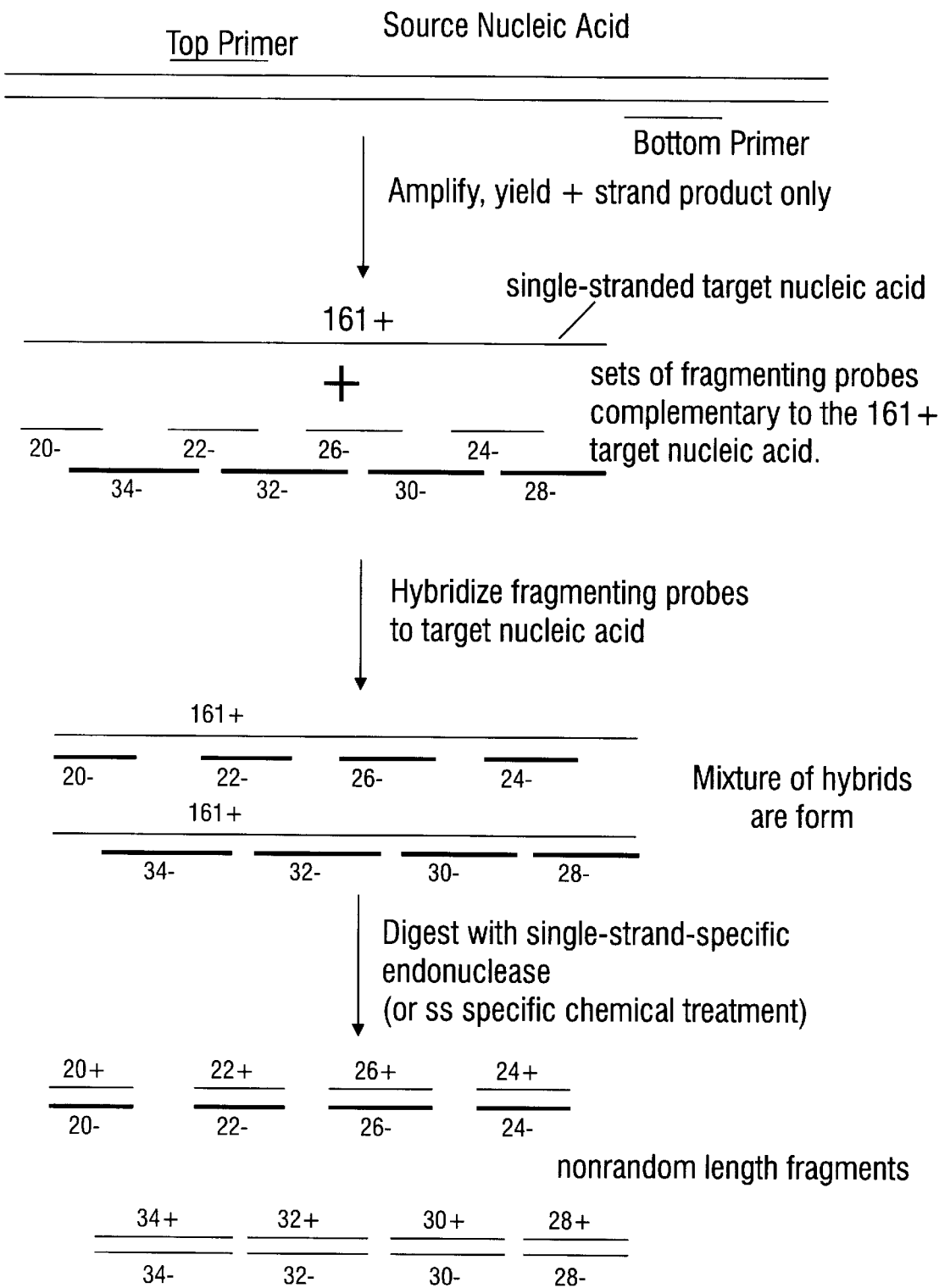
FIGS. 7A and B illustrate the use of fragmenting probes in conjunction with single-strand-specific endonuclease to produce nonrandom fragments from single-stranded target nucleic acid.
Figure 7B:
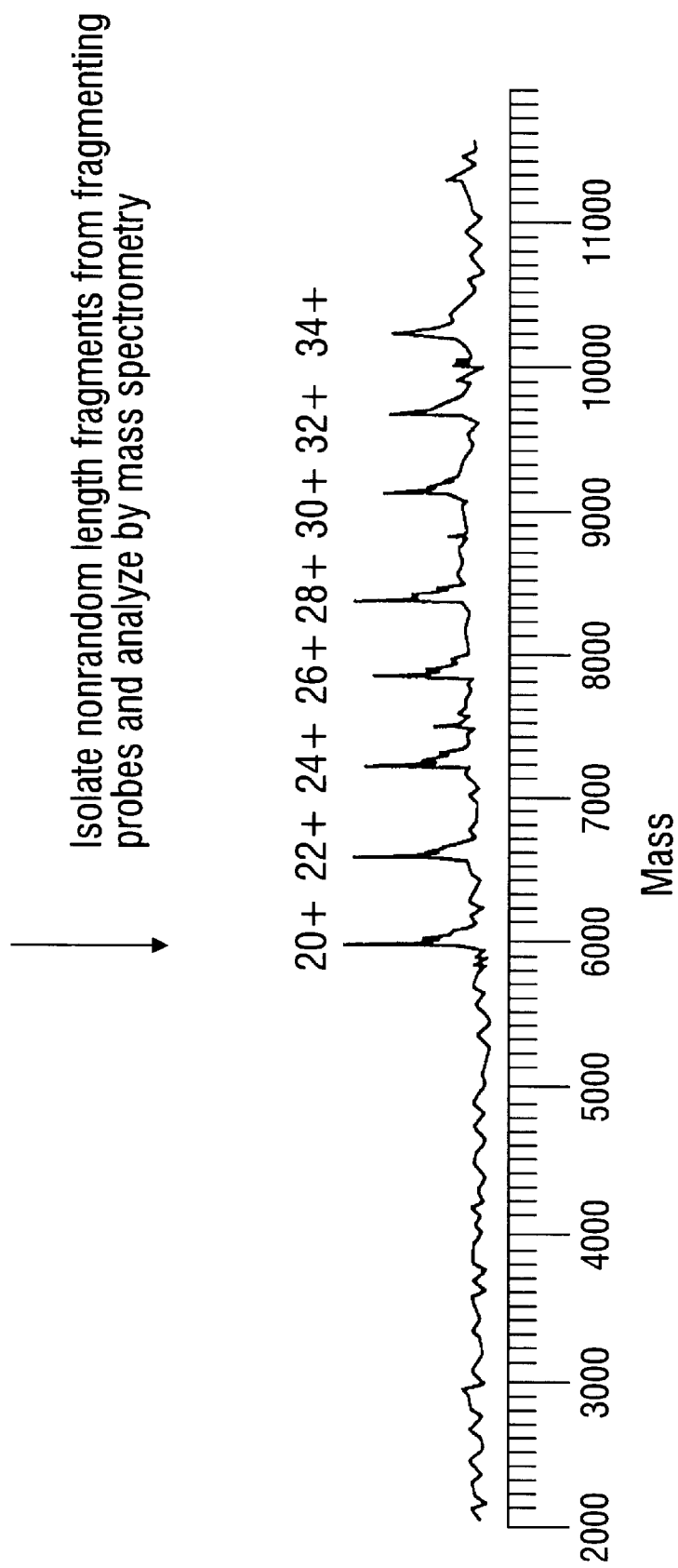

FIG. 7 shows how different portions of the single-stranded target nucleic acid are hybridized to the oligonucleotide probes. Following hybridization, any regions of the target nucleic acid that remain single-stranded are cleaved using a single-strand-specific endo/exonuclease, such as S1 Nuclease, Mung bean nuclease, or RNase A. The size of the single-stranded region can be as small as a single phosphodiester bridge, i.e. the phosphodiester bond across from a nick. S1 nuclease is capable of cleaving across from nicks. The end products are double-stranded hybrids comprised of two equal length strands: one strand is a member of the set of nonrandom length fragments derived from the target nucleic acid and the other strand is a member of the set of fragmenting probes, wherein said NLFs are hybridized to said fragmenting probes. Either these double-stranded hybrids or isolated single-stranded nonrandom length fragments derived from said target nucleic acid can be used for MALDI-TOF mass spectrometric analysis. Preferably, the analysis of the single-stranded nonrandom length fragments derived from said target nucleic acid provides a simpler mass spectrum. It should be noted that when the complementary strands are a mixed DNA/RNA hybrid there will be a significant mass difference between the two strands in all cases, making each strand more easily resolvable in the mass spectrum.

Unlike the restriction endonuclease nonrandom fragmentation approach, with this method it is possible to use a DNA/RNA hybrid providing a convenient route toward digesting the fragmenting probes after nonrandomly fragmenting the target nucleic acid. Isolation of the set of NLFs from the set of fragmenting probes is another means to simplify the mass spectra. Because of the different chemical nature of the two strands of the hybrid, it is possible to utilize DNA- or RNA-specific enzymes to digest the fragmenting probes. As an example, DNase can be used to digest fragmenting probes comprised of DNA while leaving nonrandom length RNA fragments intact or RNase can be used to digest RNA probes while leaving nonrandom length DNA fragments intact. It is also possible to utilize different chemistries to specifically digest one strand or the other. These chemistries include the use of acid to digest DNA or base to digest RNA as well as a multiplicity of other chemistries that can be use to cut modified versions of DNA or RNA. This differential cutting can be exploited to purify and analyze only one of the two strands as described in a later section.

Thus, another embodiment of this invention is a method of detecting a mutation in a DNA fragment from a DNA/RNA hybrid nucleic acid comprising obtaining a DNA/RNA hybrid wherein the DNA/RNA hybrid comprises a single-strand of a DNA fragment hybridized to a single-strand of a RNA fragment, digesting the single-strand of RNA using a RNA-specific reagent, including RNase or a base, determining the mass of the single-stranded DNA fragment using mass spectrometry, and comparing said mass to a mass of a wild type single-stranded DNA fragment. Another embodiment is a method of detecting a mutation in a RNA fragment from a DNA/RNA hybrid nucleic acid comprising obtaining a DNA/RNA hybrid wherein the DNA/RNA hybrid comprises a single-strand of a DNA fragment hybridized to a single-strand of a RNA fragment, digesting the single-strand of DNA using a DNA-specific reagent, including DNase or an acid, determining the mass of the single-stranded RNA fragment using mass spectrometry, and comparing said mass to a mass of a wild type single-stranded RNA fragment. These embodiments can also be applied to a set of DNA/RNA hybrids, and using the DNA-specific or RNA-specific digestion to leave a set of nonrandom length fragments consisting of DNA fragments or a set of nonrandom length fragments consisting of RNA fragments.

Complete digestion using restriction endonucleases produces a series of fragments that can be aligned end to end but do not overlap. With the use of fragmenting probes and single-strand-specific cleaving reagents described herein, one can design a set of sequence and size specific fragmenting probes that can be used to produce a set of nonrandom length fragments such that one or more members of the set comprise a nonoverlapping nucleotide sequence and a nucleotide sequence that overlaps with a nucleotide sequence of another member of the set. The example shown in FIG. 7 uses a set of sequence and size specific fragmenting probes that overlap (e.g. split into two sets of hybridization reactions) to produce an overlapping set of nonrandom length fragments. The set of nonrandom length fragments that overlap could be nested. By using a set of overlapping nonrandom length fragments to screen for a mutation, one can more narrowly localize the region containing a mutation. If two overlapping nonrandom length fragments both contain the mutation, as is the case in FIG. 7, it is then known that the mutation exists within the small region of overlap. Conversely, if only one of the overlapping fragments contains a mutation, it is known that the mutation cannot be in an overlapping region. This approach plus the ability to design certain fragmenting probes to be very small in size, e.g. 10 to 20 bases (typical fragmenting probes will be anywhere between 10 and 100 bases in length), allows one to probe genetic regions that are known hot spots for mutation with greater detail.

Figures 2, 8:
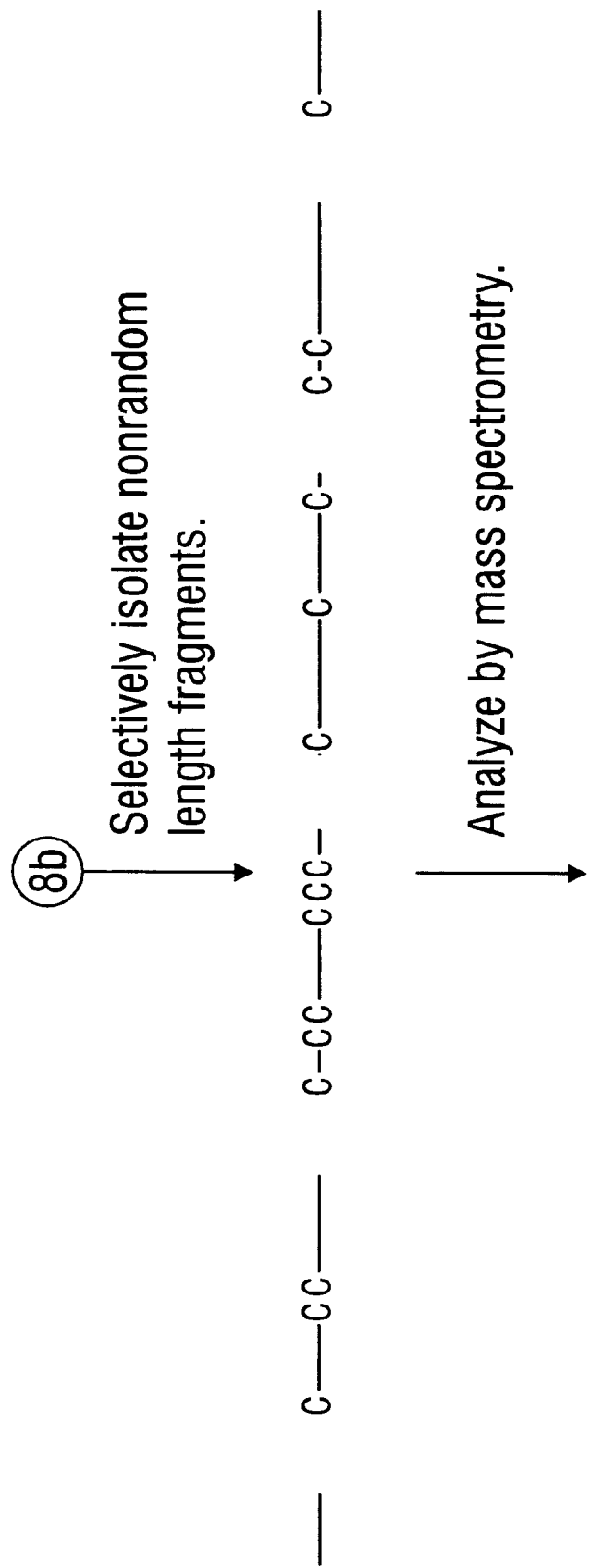
FIG. 8 is a diagram illustrating the use of fragmenting probes in conjunction with single-strand-specific, base-specific chemical cleavage to produce nonrandom fragments from single-stranded target nucleic acid.

One variant of this method is to use single-strand-specific chemical reagents as a means for cleaving a target nucleic acid target into a set of nonrandom length fragments. Several base-specific cleavage chemistries have been identified that cleave the nucleic acid backbone at base-specific sites that are single-stranded and, under optimal conditions, demonstrate zero or extremely reduced cleavage levels at base-specific sites that are double-stranded. As an option the target nucleic acid can be synthesized using one or more modified nucleotides in order to make the backbone more vulnerable to chemical cleavage. By using fragmenting probes to hybridize to a target nucleic acid at all sites except the specific locations where cleavage is desired, it is possible to limit cleavage to these single-stranded sites and create a sequence-specific set of nonrandom length fragments. The method, schematized in FIG. 8, can utilize one of a number of different chemistries that are known to be single-strand specific including hydrogen peroxide cleavage and/or 2-hydroperoxytetrahydrofuran cleavage at C. [P. Richterich et al. "Cytosine specific DNA sequencing with hydrogen peroxide" Nuc. Acids Res. 23, 4922 (1995); G. Liang, P. Gannet & B. Gold "The Use of 2-Hydroperoxytetrahydrofuran as a Reagent to Sequence Cytosine and to Probe Non-Watson-Crick DNA Structures" Nuc. Acids Res. 23, 713 (1995)]. Target nucleic acids that contain cleavage-modified nucleotides can be made by incorporation of modified nucleotide triphosphates during an amplification or polymerization step.

Figure 9A:
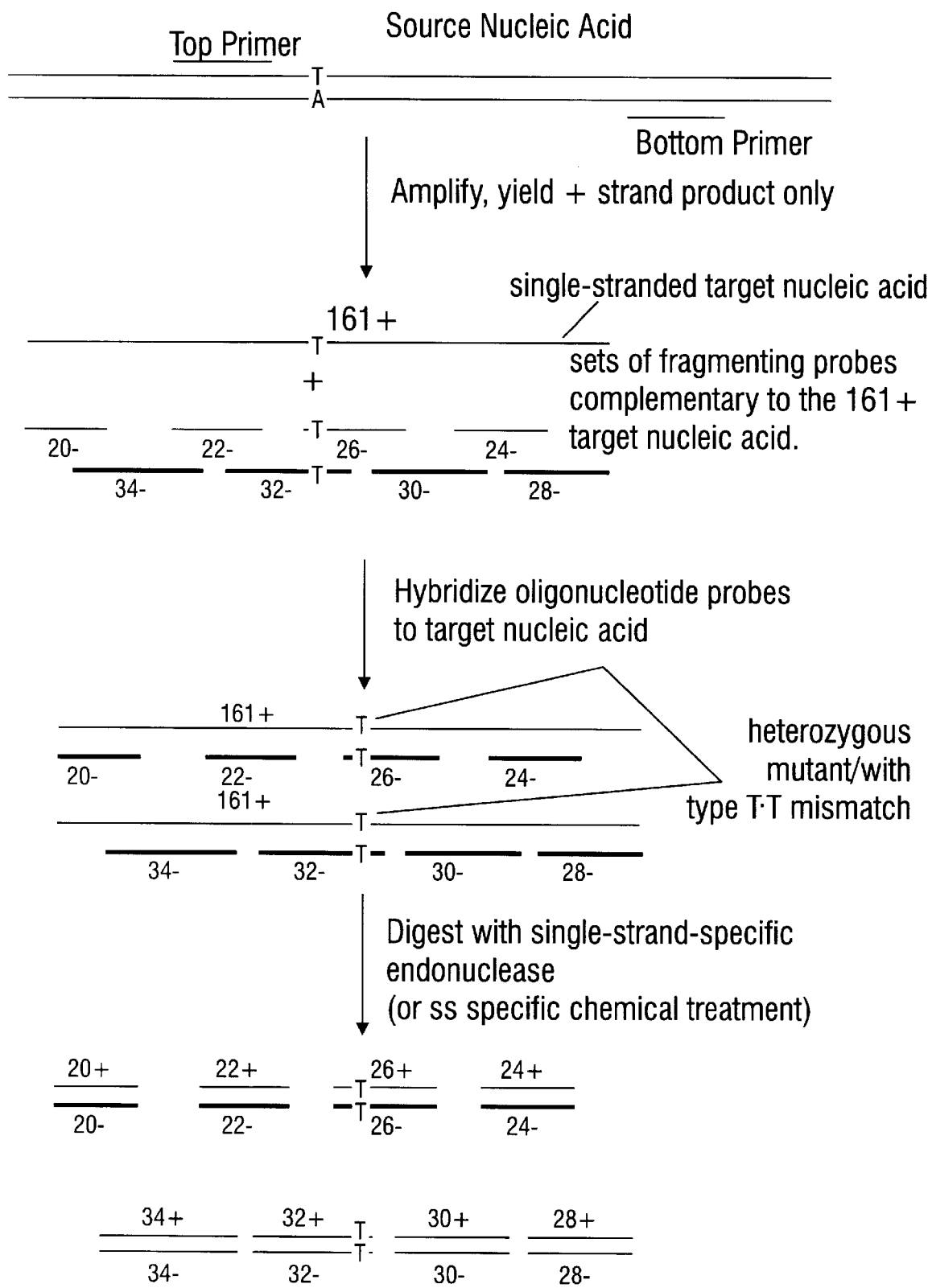
FIGS. 9A and B illustrate the use of fragmenting probes to produce nonrandom fragments from heterozygous, single-stranded target nucleic acid in combination with the use a mismatch-specific cleaving reagent to further fragment the target nucleic acid at the site of a mutation.
Figures 2, 9B:
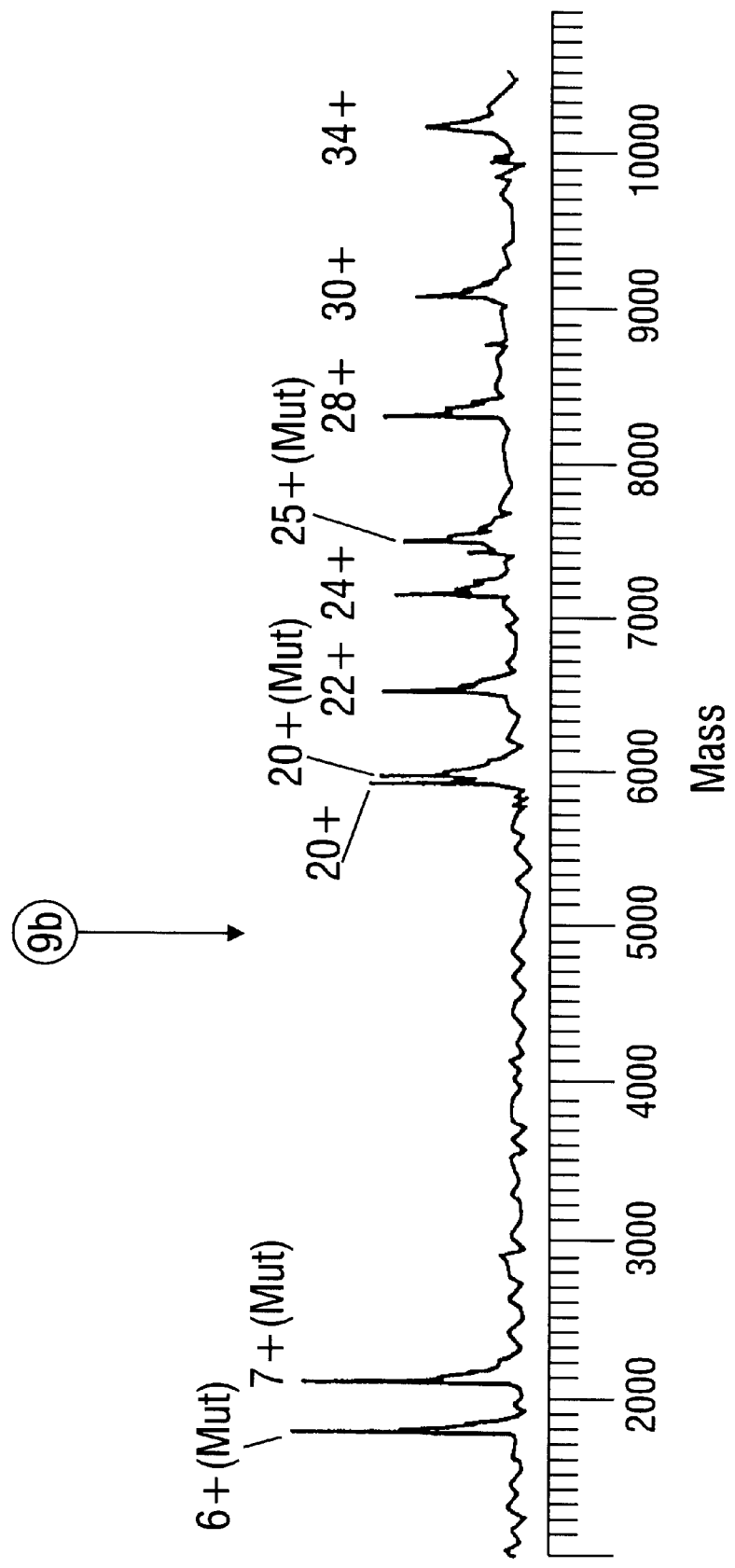

A second variant of this method is to create heterozygous hybrids between the wild type fragmenting probes and the target nucleic acid. By using fragmenting probes comprised of wild type sequence, any hybrids that form with mutant sequence containing a point mutation will create a base mismatch or bulge. If the mutation is a small insertion or deletion, a looped out sequence will occur. With this heterozygous hybrid, it is possible to use one of the structure-specific enzymes or chemistries described in the following section to create a mutation-specific cleavage at the site of a mutation. An example of the pattern of nonrandom length fragments produced is shown in FIG. 9. This approach permits determination of the type and location of the mutation that has occurred. Also as will be described, performance of a mutation-specific cleavage relaxes the mass accuracy and resolution constraints, thus increasing the useful size range for the nonrandom length fragments to be analyzed with MALDI-TOF mass spectrometry to a range of several hundred bases.

MUTATION-SPECIFIC CLEAVAGE USING STRUCTURE-SPECIFIC ENDONUCLEASES

Another nonrandom fragmentation technique involves the use of mutation-specific cleavage at base mismatch regions, if present, using structure-specific endonucleases or single-strand-specific cleavage. Creation of mismatch regions requires hybridization between a mutation containing, single-stranded target nucleic acid and a set of one or more single-stranded complementary wild type probes derived from wild type sequence. Wild type probes can be restriction site probes, fragmenting probes, or capture probes comprising wild type nucleotide sequence that when hybridized to a complementary mutation-containing region of a target nucleic acid results in a base mismatch bulge or loop structure. A base mismatch will be created at the location of the mutation. In one embodiment, the mutation containing positive strand is hybridized to a complementary wild-type probe that comprises the entire negative strand. In the preferred embodiment, the complex of mutation containing positive strand hybridized to one or more complementary, wild type nucleic acid probes is fragmented using either restriction endonucleases, or fragmenting probes coupled with a single-strand-specific cleavage reagent. Any base mismatch regions between the set of wild type probes and the set of NLFs can be specifically cleaved using one or more mismatch-specific cleaving reagents. Examples of these reagents include: structure-specific endonucleases such as T4 endonuclease VII, RuvC, MutY, or the endonucleolytic activity from the 5'–3' exonuclease subunit of thermostable DNA polymerases, single-strand-specific enzymes such as Mung bean nuclease, S1 nuclease or RNase A, and single-strand-specific chemistries such as hydroxylamine, osmium tetroxide, potassium permanganate, or peroxide modification of unpaired bases followed by a backbone cleaving oxidation step.

This mismatch-specific cleavage is used to cleave the mutation-containing nonrandom length fragment at the site of the mutation, thus producing two smaller fragments from the larger mutation-containing fragment. This approach is an efficient and simple way to identify the exact location of a mutation as well as its type. The mismatch-specific cleavage used in combination with one of the nonrandom fragmentation methods described herein can be used to fragment a large (>200 bases), single-stranded target nucleic acid into a set of smaller, mass resolvable nonrandom length fragments.

Like EMC and CCM, the mismatch-specific cleavage approach utilizes a mismatch targeting reagent to cut at the point of mutation. The approach described herein improves upon the gel electrophoresis-based methods by focusing on relatively small fragments that take maximum advantage of the mass spectrometer's ability to detect the exact size of a fragment leading to the identification of the exact location and nature of a mutation. The EMC and CCM methods must be followed by DNA sequencing in order to fully characterize a mutation. Using the methods described herein, a mutation in a target nucleic acid can be detected and its location and nature determined without any sequencing.

Figures 2, 10A:
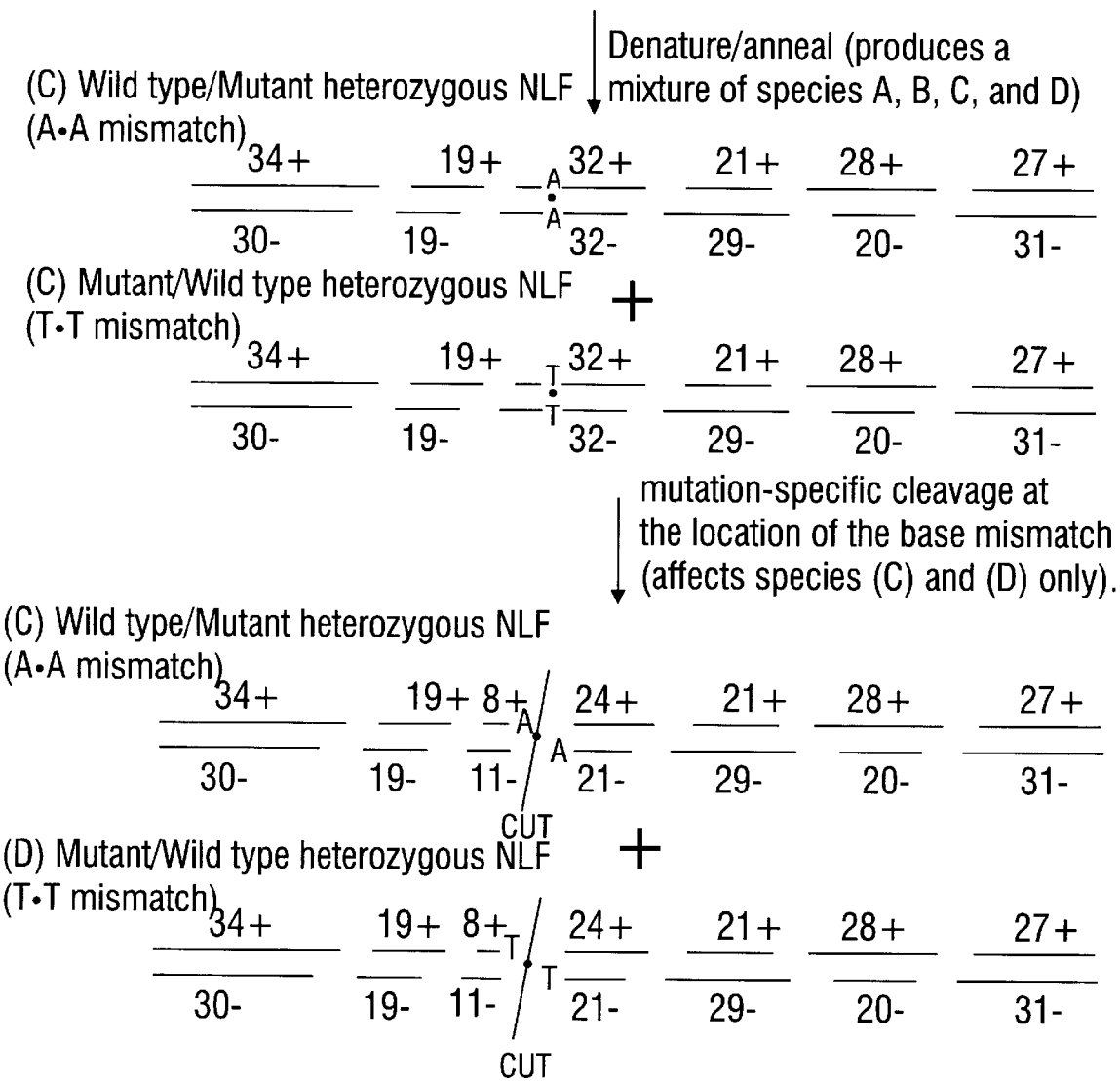

An example of how a structure-specific enzyme like T4 endonuclease VII can be used for mismatch-specific cleavage is shown in FIG. 10. The first step involves two amplification reactions. First, a target nucleic acid suspected of containing a mutation is amplified. Second, the corresponding wild type target nucleic acid is amplified to create wild type probes. These two amplification reactions can be performed together in one tube if the target nucleic acid is a heterozygous mixture of mutant and wild type. For certain diagnostic procedures, it may be more efficient to produce the wild type probes separately prior to the screening process. The next steps involve fragmentation of the target nucleic acid, e.g. a multiple digest of the target nucleic acid using more than one restriction endonuclease, and a step in which the fragments are mixed, denatured, and then annealed. The fragmentation and denaturing/annealing steps can occur in either order. The purpose of the denaturing/annealing step is to produce a mixture of hybrid target nucleic acids. In a 50:50 mixture of mutant target and wild type nucleic acids, four different products result: 25% homozygous mutant double-stranded nonrandom length fragments, 25% homozygous wild type double-stranded nonrandom length fragments, and 25% each of the two forms of heterozygous mutant/wild type hybrid nonrandom length fragments. See FIG. 10 (illustrating the use of wild type NLFs as wild type probes to generate a base mismatch with mutant NLFs). The heterozygous nonrandom length fragments contain at least one base mismatch at the site of mutation, i.e. the point(s) of sequence variation between mutant and wild type. The next step involves treatment of the nonrandom length fragments with a mismatch-specific reagent that cleaves at the site of the base mismatch in the heterozygous mutant/wild type nonrandom length fragments. These new cleavages (the number of cleavage events will depend on the particular enzyme used) typically reduce the nonrandom length fragment containing the mutation into two smaller nonrandom length fragments. The 50% of the mixture that contains the homozygous double-stranded nucleic acid fragments with no mismatches will not be cleaved during the mutation-specific cleavage.

Figure 10B:
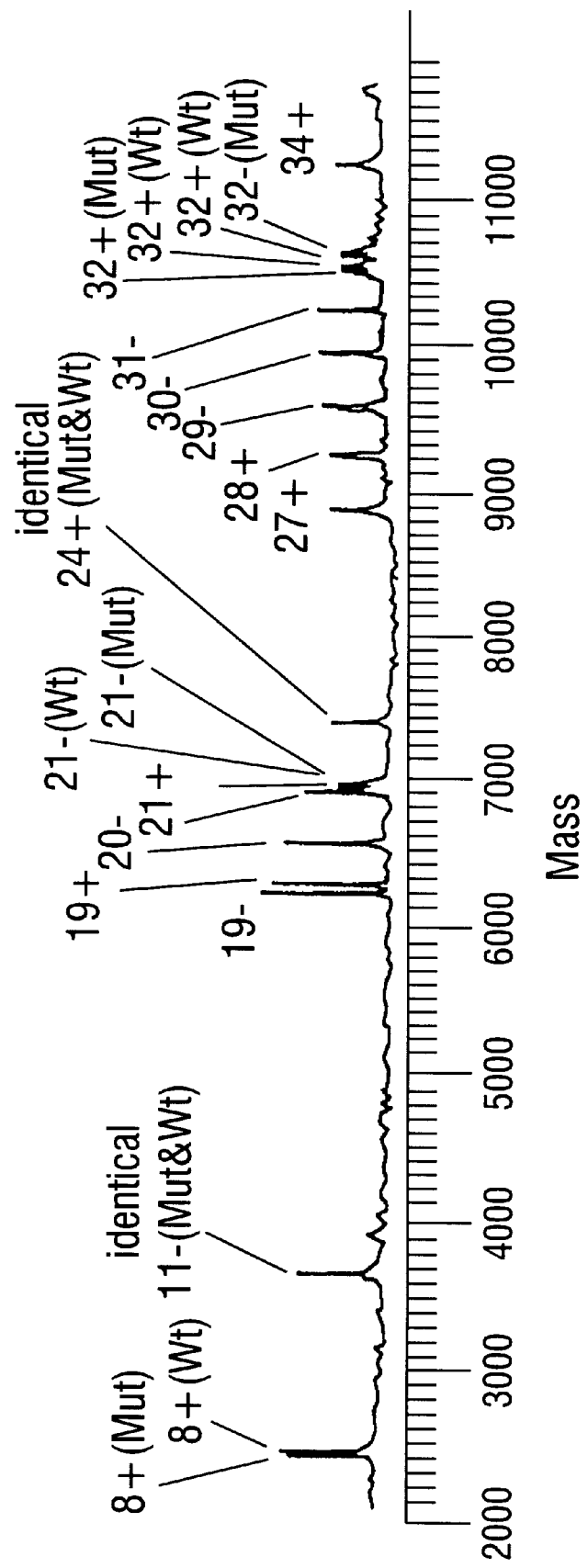
FIG. 10 is a diagram illustrating a method of detecting a mutation using mass spectrometric analysis of nonrandomly fragmented mutant and wild-type double-stranded nucleic acids that have been denatured and reannealed and then cleaved at any mismatch regions.

Example schematic mass spectral plots are shown in FIG. 10B. An expected spectrum would show a reduction in the peak size of the nonrandom length fragment containing the base mismatch that is cleaved by the structure-specific endonuclease (e.g. peaks 32+(Mut), 32+(Wt), 32-(Wt), and 32-(Mut)) and the introduction of several smaller peaks at lower masses than the mutant peaks representing the set of heterozygous mutant/wild type NLFs that contain base mismatches (see peaks 8+(Mut), 8+(Wt), 11-, 21- (Wt), 21- (Mut), and 24+). These peaks corresponding to the heterozygous NLFs containing base mismatches are reduced in intensity but continue to be present since only 50% of the molecules exist in the heterozygous form that can undergo the mutation-specific cleavage.

It is possible to bias the population of the different heterozygous/homozygous forms by performing the amplifications of the target nucleic acid asymmetrically. Thus, one can maximize the types of nonrandom length fragments yielding mutational data with the majority of the duplex formed during the annealing process being heterozygous positive (+) strand mutant and negative (−) strand wild type.

While it is possible to observe similar patterns using gel electrophoresis techniques, the mass accuracy obtained by mass spectrometry provides the advantage of accurate determination of the nature of the mutation and the ability to determine the size and order of the two nonrandom length fragments created by the mutation-specific cleavage. In the example in FIG. 10B, the resulting mismatch-specific cleavage fragments are represented by sizes 8, 11, 21, and 24 nucleotides in length. Using electrophoretic techniques, it would be impossible to differentiate the two mutant forms at 8 and 21 (fragments 24+ and 12− do not possess the mutant base and are identical in heterozygous forms C and D), nor would it be possible to directly determine which fragment is upstream (toward the 5' end) and which fragment is downstream (toward the 3' end), e.g. in the positive strand it is 8+ that is upstream from 24+. By providing exact mass values, mass spectrometry allows these strands to be ordered based on mass value database comparison with the fragments expected from the known sequence of the wild type target nucleic acid. By completely identifying the location and nature of the mutation this mass spectrometric method eliminates any need for sequencing the target nucleic acid.

Figures 2, 11:
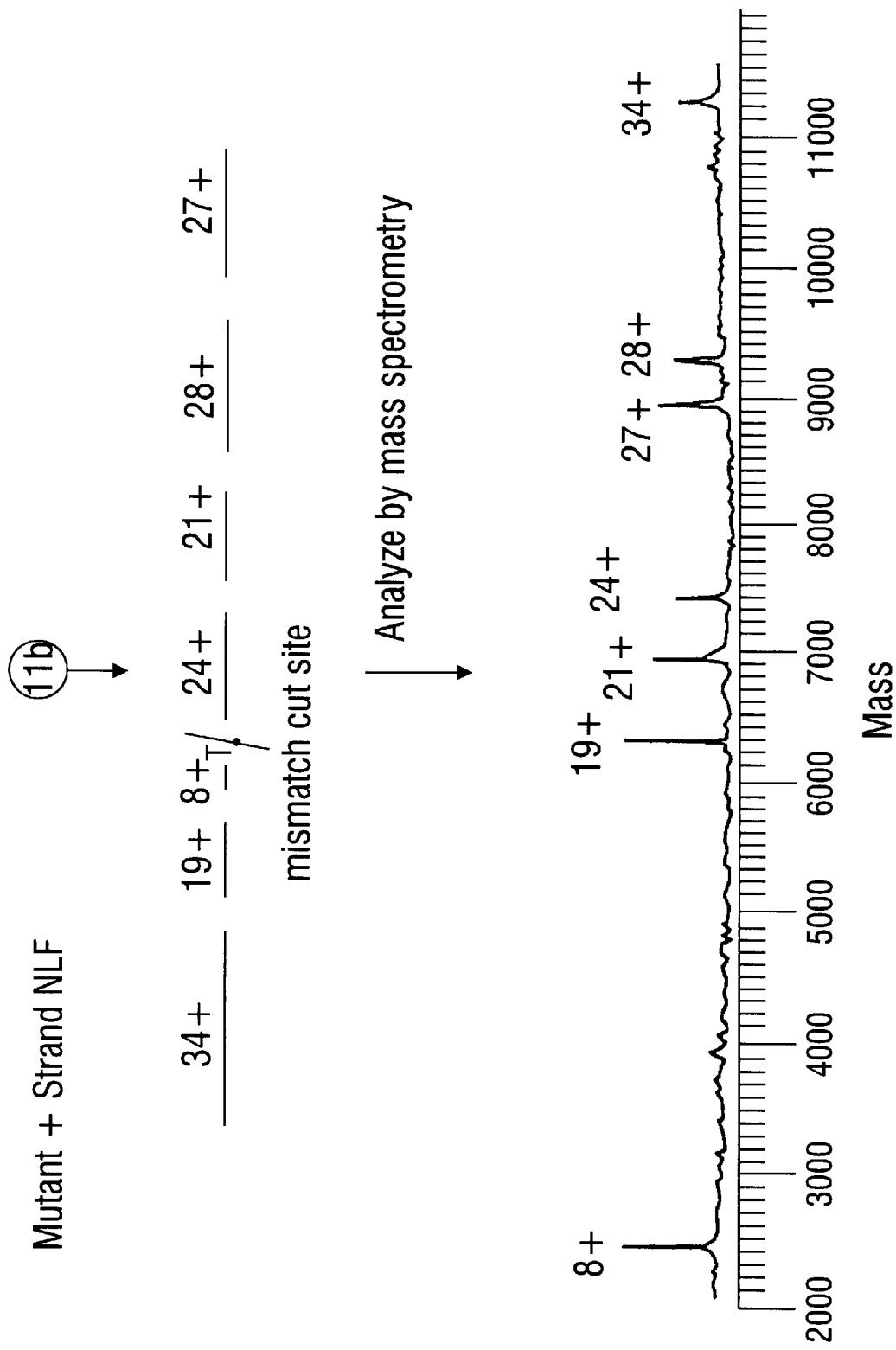
FIG. 11 is a diagram illustrating the effect of analyzing only positive strand fragments from a heterozygous sample in reducing the number of total fragments and simplifying the mass spectrum. In this case the positive strand has been nonrandomly fragmented using both restriction endonuclease treatment and mismatch-specific cleavage.

FIG. 10B shows how the mismatch-specific cleavage event adds complexity to the mass spectra. In the example shown, there are several locations where 2, 3, and even 4 different NLFs have the potential to overlap in the mass spectrum, making the full spectrum difficult to resolve. As discussed previously, and shown in FIG. 5, the mass spectra can be greatly simplified by performing the mass spectrometric analysis on only the + or the − strands of the nonrandom length fragments. For example, FIG. 11 shows the set of nonrandom length fragments that are derived by analyzing only the + positive strand of the mutant target nucleic acid. By eliminating the homozygous nonrandom length fragments that are not mutation-specifically cleaved and removing the negative strand from the mass spectrometric analysis, the total number of nonrandom length fragments to be analyzed can be reduced from 20 to 7, with no two mass peaks having the same number of nucleotides. Of course, in other situations, two peaks may be from nonrandom length fragments of the same length depending on the type of mutation present, but such situations will be infrequent.

This mismatch-specific cleavage, like the incorporation of mass-modified nucleotides, extends the usable mass range of the initial target nucleic acid for mass spectrometric analysis since the primary mass accuracy needs are in determining the reduced mass of the nonrandom length fragments created by the mutation-specific cleavage and not in determining the mass of the other nonrandom length fragments that are unaffected by the mutation-specific cleavage.

It is not always necessary to fragment the target nucleic acid in tandem with mismatch-specific cleavage if the size of the nonrandom length fragments created by the mismatch-specific cleavage is small enough to fall into the usable mass range with the necessary mass resolution and accuracy. Target nucleic acids as large as 200 base pairs will yield at least one nonrandom length fragment created by the mutation-specific cleavage wherein the nonrandom length fragments can be a size less than 100 base pairs, e.g. a 200 bp target nucleic acid with a mutation at position 135 will produce nonrandom length fragments of 65 and 135 after cleavage at the site of base mismatch.

FRAGMENTATION USING STRUCTURE-SPECIFIC ENDONUCLEASES TO CLEAVE A FOLDED TARGET NUCLEIC ACID

Figure 12:
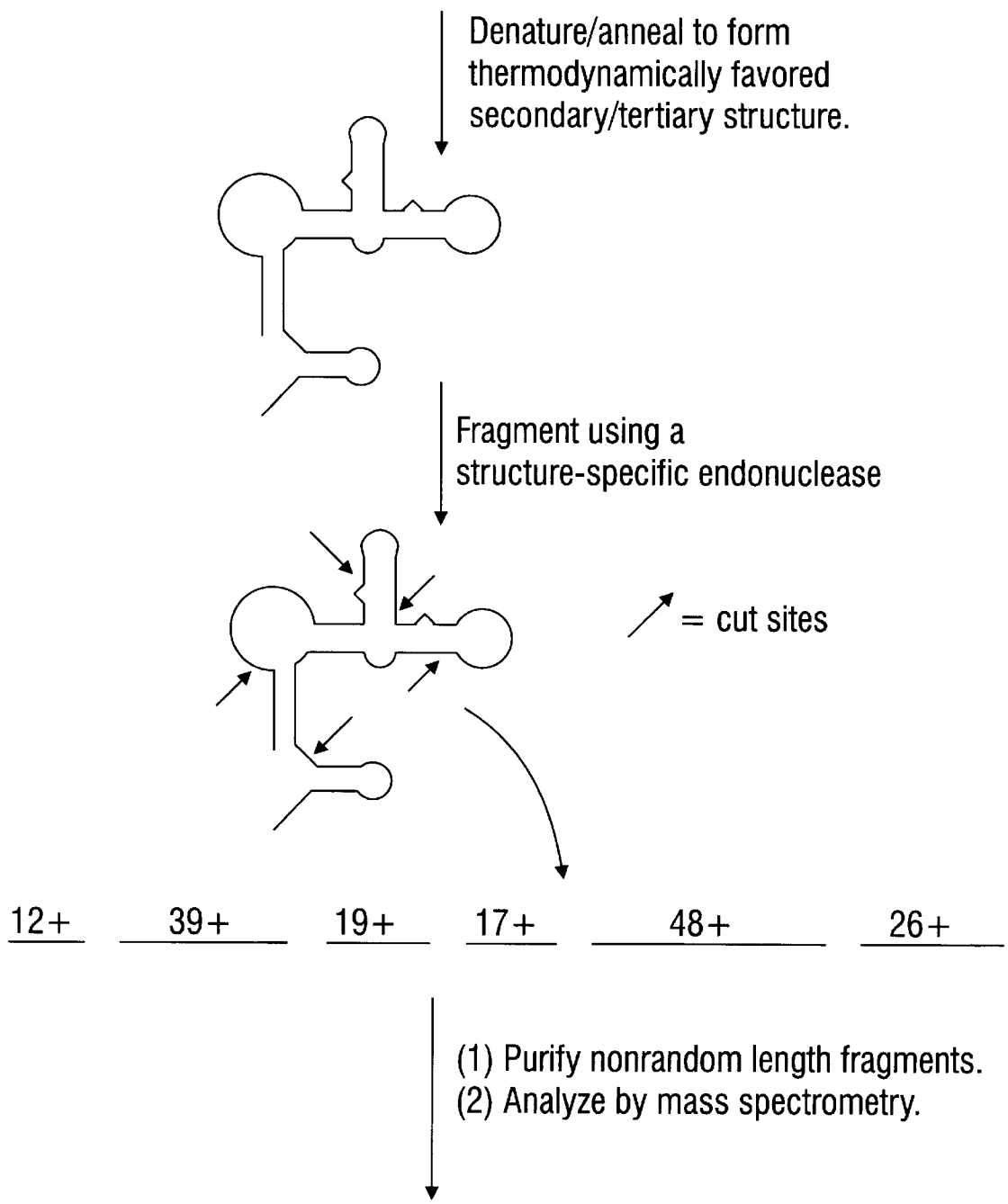
FIG. 12 is a diagram illustrating the use of structures-specific endonucleases to nonrandomly fragment a folded, single-stranded target nucleic acid.

Another nonrandom fragmentation method of the invention involves providing a target nucleic acid that is either a positive or a negative single-strand; providing conditions permitting folding of the single-stranded target nucleic acid to form a three-dimensional structure having intramolecular secondary and tertiary interactions, and nonrandomly fragmenting the folded target nucleic acid with at least one structure-specific endonuclease to form a set of single-stranded nonrandom length fragments. A diagram of this procedure is provided in FIG. 12. An example of conditions that permit folding of the single-stranded target nucleic acid are heating to denaturation followed by slow cooling to permit annealing to form a thermodynamically favored secondary and tertiary structure. The structure-specific endonucleases include: T4 endonuclease VII, RuvC, MutY, and the endonucleolytic activity from the 5'–3' exonuclease subunit of thermostable DNA polymerases.

An alternative to the use of structure-specific endonucleases is the use of some of the same single-strand-specific chemical cleavage procedures describe earlier in the text. Because of the higher frequency with which these reagents might cleave relative to the structure-specific endonucleases, it is necessary that the secondary and tertiary structures formed by the single-stranded target be more compact, limiting the access of the chemical reagents to the various reactive nucleotides. Approaches to forming these more compact structures include performance of the reactions at lower temperature, under higher salt conditions, or the use of RNA versus DNA since RNA is known to form more complete secondary and tertiary structures. Using this method, the cleavage reaction can be run to completion to produce a standard set of nonrandom length fragments or run only partially with the potential of producing a nested set of products that can be analyzed by mass spectrometry or by electrophoresis methods.

PURIFICATION METHODS

When analyzing nucleic acids, including nonrandom length fragments, by mass spectrometry, there are several requirements that need to be met.

First, as has been described earlier, is the need to produce fragments within the resolvable range and high mass accuracy range of the mass spectrometer.

Second, is to eliminate from the sample, nucleic acid fragments that do not contribute to the analysis and may unnecessarily convolute the mass spectra. With analysis methods such as gel electrophoresis, a mixture of specifically labeled nucleic acid fragments (radioactive or by fluorescent tagged) can be visualized in the presence of other unlabeled nucleic acid fragments that comigrate but are invisible and therefore do not convolute analysis of the gel data. The mass spectrometric methods described herein do not use any form of labeling that could render certain fragments invisible, e.g. the negative strand in a double-stranded product, and it is therefore necessary to remove such fragments prior to analysis.

Third, is the need to produce samples of relatively high purity prior to introduction to the mass spectrometer. The presence of impurities, especially salts, greatly affects the resolution, accuracy and intensity of the mass spectrometric signal. Contaminating primers, residual sample genomic DNA, and proteins, all can affect the quality of the mass spectra.

In addition to the three requirements listed above it is also desirable for the methods to be amenable to automation, fast and inexpensive, providing an effective approach for detecting genetic mutations.

Existing purification methods are all designed to work with labeled molecules that were typically analyzed by gel electrophoresis. As well as utilizing labels, electrophoresis is, to a certain degree, tolerant of impurities including salts and proteins. For mass spectrometric analysis, prior art purification methods such as precipitation combined with vigorous alcohol washes, filtering and dialysis, and ion exchange chromatography are unsatisfactory because they cannot eliminate unwanted nucleic acid fragments and normally do not remove all salts from a sample. Solid phase approaches such as glass bead capture under high salt conditions, biotin/streptavidin binding, direct solid-phase covalent linkage, and capture via hybridization to solid phase bound oligonucleotide probes can be used to eliminate unwanted nucleic acid fragments but typically require high levels of salt during many of the wash steps, rendering the products less pure and compromised for mass spectrometric analysis.

The purifications methods of the present invention are better suited to mass spectrometric analysis of nucleic acids than the prior art methods. First, the methods herein physically isolate selected sets of nucleic acids from a multiplicity of impurities including undesirable nucleic acid fragments, proteins, salts, that would result in a poor quality mass spectrum. Second, the methods optionally use a solution comprising volatile salts such as ammonium bicarbonate, dimethyl ammonium bicarbonate or trimethyl ammonium bicarbonate in any of the steps, including hybridization, endonuclease digestion or washing. These two differences are significant advantages over the prior art because: (1) physical separation of the desired set of nucleic acid fragments for mass spectrometric analysis is better than the labelling methods of the prior art that do not physically separate the target nucleic acids from a variety of other impurities that interfere with an accurate mass spectrum; and (2) the use of volatile salts in any of the steps precludes the need for any wash step known in the prior art to merely remove salts or inorganic ions.

Double Strand Fragment Capture Approaches

There are a number of basic ways to purify DNA restriction products from salts and other small molecules including precipitation, filtering, dialysis, and ion exchange chromatography. While all of these methods are effective, they are not all equally useful for removing amplification primers, residual DNA, i.e. genomic DNA, or any proteins used. In addition, none of the basic approaches meets all of the requirements of automation, speed and cost. The approach that comes closest is the use of small ion exchange spin columns, which are somewhat expensive and not simple to integrate into an automated setup. These small ion exchange spin columns can, however, produce high quality nucleic acids for mass spectrometric analysis. A better alternative is the use of (magnetic) glass beads to capture/precipitate nucleic acids of a specific size range and allow them to be rigorously washed. However, this method, like all of the other prior art methods described above, does not allow for the removal of unincorporated DNA primer since they are of the same size as the nonrandom length fragments to be analyzed and cannot be simply differentiated.

Another general approach to purification of double-stranded fragments is to directly capture the target nucleic acid and/or a set of nonrandom length fragments by one of three means: (A) hybridization to capture probes comprising a first binding moiety that specifically binds to a second binding moiety attached to a solid phase; (B) binding the target nucleic acid or the members of the set of NLFs each comprising a nucleotide sequence and a first binding moiety to a second binding moiety attached to a solid phase; or (C) direct covalent attachment of the target nucleic acid or the members of the set of NLFs to the solid support. Each of these methods has advantages and disadvantages.

(A) Hybridization to solid support bound capture probes is straightforward, specific, and can be made thermodynamically and kinetically favored by optimizing the size and concentration of the capture probes. Optimization is necessary since the set of NLFs would generally prefer to hybridize to their complements rather than to the capture probes. (This approach also works well for single-strand isolation as described in the following section.) A variation is to bind the probes to the solid phase after hybridization to target. Both biotin/streptavidin and covalent approaches for linking the probes to the solid phase are feasible. The principal concern with this approach is that maintenance of the hybridization, especially during wash steps, requires relatively high level of salts and makes it more difficult to produce a salt-free product for mass spectrometric analysis. Solutions to this problem include the use of relatively long capture probes to increase melting temperatures or the use of volatile salts that can be removed prior to mass spectrometric analysis. The use of volatile salts is described in more detail elsewhere.

(B) Biotin coupling to streptavidin (or avidin) requires that any target nucleic acid or nonrandom length fragment to be captured contain a biotin. It is straightforward to capture the target nucleic acid because biotinylated primers can be used in the PCR amplification. In order to capture all of the fragments after a restriction digest, it is necessary to incorporate biotin into all of the fragments. Three possible routes for biotin labeling are, (1) the inclusion of a biotinylated nucleoside triphosphate during fragment synthesis, (2) the use of a DNA polymerase to fill in at 5' restriction overhangs using a biotinylated nucleoside triphosphate, and (3) the use of ligase to ligate a biotinylated oligonucleotide at the restricted ends of the nonrandom length fragments, where the oligonucleotides are either complementary to the restriction sequence overhangs or are capable of blunt end ligation.

Each of the three approaches have their problems but are feasible. Biotins incorporated in method (1) may inhibit the restriction endonucleases to be used and prevent the use of structure-specific nucleases in a second mutation-specific step since the biotin may be recognized as DNA modifications to be excised. Method (2) is more feasible but requires a preliminary cleanup step to exchange the normal triphosphates for biotinylated ones. Restriction sites are limited to enzymes that produce 5' overhangs. Method (3) is more generalizable than (2); its principal weakness is competition with larger fragments that will want to relegate. However, this competition can be overcome by using an excess of the biotinylated linkers.

(C) The approach of direct covalent attachment of NLFs or target to a solid support faces many of the same challenges as the biotin/streptavidin approach but also includes the need to design specific, "hot" (i.e. fast and efficient) binding chemistry working with low concentrations of material.

The target or members of a set of NLFs can be covalently attached to a solid support using any of the number of methods commonly employed in the art to immobilize an oligonucleotide or polynucleotide on a solid support. The target or NLFs covalently attached to the solid support should be stable and accessible for base hybridization.

Covalent attachment of the target or NLFs to the solid support may occur by reaction between a reactive site or a binding moiety on the solid support and a reactive site or another binding moiety attached to the target or NLFs or via intervening linkers or spacer molecules, where the two binding moieties can react to form a covalent bond. Coupling of a target or NLF to a solid support may be carried out through a variety of covalent attachment functional groups. Any suitable functional group may be used to attach the target or NLF to the solid support, including disulfide, carbamate, hydrazone, ester, N-functionalized thiourea, functionalized maleimide, streptavidin or avidin/biotin, mercuric-sulfide, gold-sulfide, amide, thiolester, azo, ether and amino.

The solid support may be made from the following materials: cellulose, nitrocellulose, nylon membranes, controlled-pore glass beads, acrylamide gels, polystyrene, activated dextran, agarose, polyethylene, functionalized plastics, glass, silicon, aluminum, steel, iron, copper, nickel and gold. Some solid support materials may require functionalization prior to attachment of an oligonucleotide or capture probe. Solid supports that may require such surface modification include wafers of aluminum, steel, iron, copper, nickel, gold, and silicon. Solid support materials for use in coupling to a capture probe include functionalized supports such as the 1,1'-carbonyldiimidazole activated supports available from Pierce (Rockford, Ill.) or functionalized supports such as those commercially available from Chiron Corp. (Emeryville, Calif.). Binding of a target or NLF to a solid support can be carried out by reacting a free amino group of an amino-modified target or NLF with the reactive imidazote carbamate of the solid support. Displacement of the imidazole group results in formation of a stable N-alkyl carbamate linkage between the target or NLFs and the support.

The target or NLFs may also be bound to a solid support comprising a gold surface. The target or NLFs can be modified at their 5'-end with a linker arm terminating in a thiol group, and the modified target or NLFs can be chemisorbed with high affinity onto gold surfaces (Hegner, et al., Surface Sci. 291:39–46 (1993b)).

In all of the methods in which a solid-phase approach is used, the double-stranded nonrandom length fragments can be rigorously washed to remove deleterious contaminants. Following washing it is necessary to release these fragments from the solid support for mass spectrometric analysis. The isolation of a set of NLFs may be performed on the same plate that is used within the mass spectrometer. Both the capture probe hybridization and biotin/streptavidin approaches can use heat and/or pH denaturation to disrupt the noncovalent interactions and afford release of the set of NLFs bound to the solid support. Alternatively, a cleavable linkage can be incorporated between the first binding moiety and the NLFs. Any covalent coupling chemistry will need to be either reversible or it will be necessary to include a separate chemically cleavable linkage somewhere within the bound product. It may also be useful to use a chemically cleavable linkage approach with the biotin/streptavidin strategies so that release of the double-stranded fragments can be performed under relatively mild conditions. In all cases the cleavable linkage can be located within the linker molecule connecting the biotin and the base (e.g. a disulfide bond in the linker), within the base itself (e.g. a more labile glycosidic linkage), or within the phosphate backbone linkage (e.g. replacement of phosphate with a phosphoramidate).

One alternative to these solid-phase approaches described above is to capture the target nucleic acids prior to nonrandom fragmentation with one or more restriction endonucleases. Rigorous washes to remove polymerase, salts, primers and triphosphates required for amplification are followed by treatment with minimal amounts of restriction enzyme under very low salt conditions. This mixture is then directly analyzed in the mass spectrometer. Mass spectrometry can tolerate salts if their concentrations are low enough and a limited class of restriction enzymes can work under very low salt conditions.

The low salt approach does limit the restriction sites that can be cleaved as part of the methods of detecting mutations. Many restriction endonucleases require a significant level of salt. An attractive alternative to limiting the restriction endonuclease cleavage reactions to low levels of salt is to replace the salts normally used with volatile salts. These salts, such as ammonium bicarbonate, dimethylammonium bicarbonate or trimethylammonium bicarbonate, can be removed prior to mass spectrometric analysis through simple evaporation. Evaporation can be accelerated by placement of the sample in a vacuum, such as the mass spectrometer sample chamber, or by heating the sample.

APPROACHES TO CAPTURING SINGLE-STRANDED FRAGMENTS

As described earlier, analysis of single-stranded nonrandom length fragments is generally preferable since it provides a complete set of data with the minimal number of fragments and therefore simplifies the spectra and facilitates an increase in the total length of nucleic acid that can be analyzed in a single assay. A number of approaches, as described above, can be taken toward the production of single-stranded fragments and their purification which includes the elimination of undesired fragments.

If DNA restriction endonucleases are used to produce the nonrandom length fragments, it is necessary that the target nucleic acid have a double-stranded form prior to restriction, or more specifically, that the restriction endonuclease recognition sites be located in double-stranded DNA. The alternative to having fully double-stranded DNA prior to restriction is to hybridize restriction site probes to single-stranded DNA, wherein the restriction site probes are complementary to the restriction sites for selected restriction endonucleases.

The basic known methods for DNA isolation—precipitation, dialysis, filtration and chromatography do not isolate single-stranded from double-stranded DNA. If these purification methods are employed it is necessary to add a separate step where single-strand isolation is performed.

Isolation of a set of single-stranded NLFs can be accomplished using a set of capture probes. "Capture probes" are oligonucleotides or polynucleotides comprising a single-stranded region complementary to at least one nucleotide sequence of the single-stranded NLFs to be isolated and a first binding moiety. The first binding moiety is capable of covalent or noncovalent binding to a second binding moiety attached to a solid support. The capture probes can comprise a set of capture probes, each of which contains single-stranded regions complementary to a corresponding member of a set of NLFs. A capture probe can also comprise a full-length single-stranded target nucleic acid that is complementary to the nucleotide sequences of the members of a set of NLFs. The capture probes can be bound to a solid support using the methods described above for binding a target or set of NLFs to a solid support.

Figures 2, 13B:
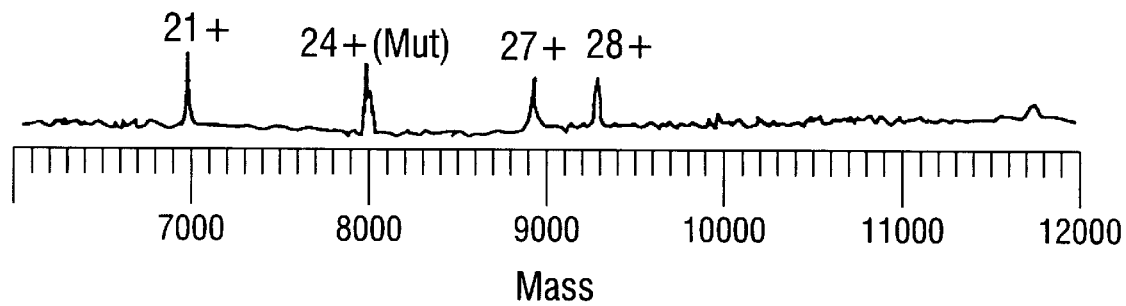

If restriction endonucleases are used to produce nonrandom length fragments from DNA, the preferred method for isolating single-strand fragments from these products is to use a select set of capture probes. In one embodiment the capture probe consists of either full length positive or full length negative strand where the strand has been modified to contain a solid-phase binding moiety. The process using full length negative strand modified to contain a biotin at the 5' end is illustrated in FIG. 13. The capture probe is made and the target nucleic acid is fragmented in two separate reactions. Following inactivation of the restriction enzymes the probe and double-stranded fragments are mixed, denatured and annealed producing a hybrid product of positive strand fragments annealed to full length negative strand capture probe. The capture probe can be bound to the solid phase via a biotin-streptavidin interaction prior to or following of the probe/fragment hybrid. Following the necessary wash steps the fragments are released and analyzed by mass spectrometry. Optionally, the fragments can be probed for a mutation-specific base-base mismatch and fragmented using one of the mismatch specific reagents described earlier. Illustrations of the different spectra produced without and with the optional second step are shown in FIG. 13. Note that after mutation-specific, mismatch-specific cleavage fragments that are distal from the solid phase binding site will be released into solution and washed away, therefore, not analyzed. Lose of these fragments can enhance the ability for mass spectrometry to quickly and easily identify the site of mutation.

An alternative approach to using restriction endonucleases is the use of fragmenting probes. These have been described in detail above, and allow the use of a target nucleic acid consisting of either DNA or RNA. The final products, using fragmenting probes and single-strand-specific nucleases, are double-stranded and thus without any additional steps do not themselves produce the set of single-stranded, nonrandom length fragments necessary for analysis. However, there are several approaches that can be used to yield single-stranded nonrandom length fragments.

The first approach for producing single-stranded nonrandom length fragments is useful when the target is RNA and the probes are DNA or visa versa. In this case, the double-stranded products are RNA/DNA hybrids and can be selectively treated with either a DNA or RNA specific nuclease to yield the opposite NLF intact. Acid or base treatments are also an option. These single-stranded products can then be isolated using a number of conventional methods described above.

A second approach to producing single-stranded products for mass spectrometry is to attach the size and sequence specific capture probes to a solid support before or after hybridization to the target nucleic acid and the single-strand-specific cleavage. Since the probes are bound to the solid phase it becomes possible to capture, wash, and then selectively release the nonrandom length target fragments as single-stranded molecules. Following any wash steps, the nonrandom length target fragments are removed from the solid support by denaturation of the double-stranded complex. Once released, the single-stranded fragments can be directly analyzed by the mass spectrometer.

One of skill in the art will know how to use capture probes to capture single-strands of a set of NLFs to a solid support in all the embodiments of this invention. For example biotinylated capture probes can be used to capture single-stranded fragments following cleavage of the target nucleic acid with restriction endonucleases (optionally after neutralizing the restriction endonucleases). The use of capture probes provides a relatively high level of flexibility to select which set of NLFs to analyze at any given time. Large capture probes, capable of hybridizing to all or several different fragments, can be used to capture the fragments correlating to one strand of a target nucleic acid, e.g. a capture probe that is full length negative strand. A short capture probe or combinations of shorter capture probes can be used to selectively choose particular fragments from either strand to analyze in a given mass spectrometric sample. For example, if several fragments share similar sizes it might be preferable to analyze them separately.

As another embodiment, a full length target nucleic acid can be captured before restriction digestion using a capture probe that is nuclease resistant. In this case it is necessary to modify the capture probe, typically by changing the backbone composition from phosphate to a phosphorothioate, methyl phosphonate or borano-phosphate. [Uhlmann and Peyman, "Antisense Oligonucleotides: A New Therapeutic Principle," Chemical Reviews 90(4):543–584 (1990) (incorporated by reference herein)] These forms of modification limit cutting on the probe strand, resulting only in the nicking of the target molecule to create sequence-specific, nonrandom length fragments without creating any double stranded breaks. By leaving the modified probe strand intact, it is possible to quickly capture the nonrandom length fragments to the solid phase and purify for mass spectrometric analysis.

All of these isolation or purification methods can be utilized in cases where a mutation-specific cleavage event is utilized. In order to present a base mismatch mutation for cleavage, a heterozygous, double-stranded molecule must be present. Typically this means that the fragmenting probe is composed of the wild type sequence and is hybridized to the target nucleic acid fragments containing the potentially mutated target nucleic acid.

VOLATILE SALTS

The methods of this invention include the use of volatile salts, which is an innovative alternative to NaCl, $MgCl_2$, or other commonly used salts. Volatile salts are any salts that completely evaporate, leaving little or no salt residue in the sample to be analyzed in the mass spectrometer, for example, the isolated set of NLFs. Volatile salts useful in the methods described herein include ammonium bicarbonate, dimethyl ammonium bicarbonate and trimethyl ammonium bicarbonate. These volatile salts are useful in many different aspects of the methods described herein, including use in hybridizing of nucleic acids, washing nucleic acids to remove impurities, and digestion of nucleic acids with endonucleases or other enzymes. Rather than performing washes at reduced levels of nonvolatile salts, which might cause the nonrandom length target fragments to denature from a solid support bound oligonucleotide probe, it is a preferred embodiment to wash supportbound nonrandom length fragments in the presence of relatively high levels of $NH_4HCO_3$, e.g. 100 mM, and then to evaporate the volatile salt prior to analysis by mass spectrometry. Volatile salts are useful for buffer exchange in all cases where nucleic acids are to be analyzed by mass spectrometry.

Solid phase purification schemes involving DNA hybridization commonly described in the literature do not focus on the removal of salts since gel electrophoresis techniques are much more tolerant of salts than mass spectrometry. [S. Wang, M. Krinks & M. Moos "DNA Sequencing from Single Phage Plaques using Solid-Phase Magnetic Capture" Biotechniques 18, 130 (1995); R. Sandaltzopoulos & P. Becker "Solid-Phase DNase I Footprinting" Boehringer Mannheim Biochemica 4, 25 (1995); both incorporated by reference herein] These methods are primarily focus on the removal of strands complementary to template prior to enzymatic reaction and/or enzymes and unincorporated labeled nucleotides or primers following reaction. In such schemes residual salt levels can be as high as 100 mM NaCl and 25 mM $MgCl_2$. Mass spectrometry is intolerant of salt concentrations of this level. [T. Shaler et al. "Effect of Impurities on the Matrix-Assisted Laser Desorption Mass Spectra of Single-Stranded Oligodeoxynucleotides" Anal. Chem. 68, 576 (1996)] The methods described herein using volatile salts provide an innovative approach to isolating and handling target nucleic acids and/or nonrandom length fragments for mass spectrometric analysis.

The volatile salts can be removed from the sample prior to mass spectrometric analysis by evaporation. Evaporation of the volatile salts can be enhanced using a variety of methods, including use of vacuum, heating, laminar flow of a dry gas over the sample, or, in the case of ammonium bicarbonate (or dimethyl- or trimethylammonium bicarbonate), reduction of the pH by addition of an acid, including 3-HPA, can speed up the decomposition of the salt into ammonia (or dimethyl- or trimethylammonia) and carbon dioxide. Volatile salts can be used in a variety of methods, beyond those described here, for preparing samples of any number of organic molecules, including proteins, polypeptides, and polynucleotides, for mass spectrometric analysis.

Each of the nonrandom fragmentation techniques described herein can be used in combination with any of the isolation methods also described herein. Moreover the nonrandom fragmentation techniques can be used in combination with each other, as one of ordinary skill in the art using the techniques described herein how to combine the different aspects of the invention. For example, the mutation-specific cleavage technique can be combined with a set of restriction endonuclease-cleaved NLFs. All of these methods and combinations thereof can optionally include use of mass-modified nucleotides, internal calibrants and volatile salts.

The kits described above for nonrandomly fragmenting target nucleic acids and detecting mutations in one or more target nucleic acids can also contain a combination of different means of nonrandomly fragmenting the target nucleic acids as well as different means of isolating the nonrandom length fragments that are to be analyzed by mass spectrometry.

The following examples are provided to illustrate embodiments of the invention, but do not limit the scope of the invention.

EXAMPLES

Example 1. PCR Amplification of Source Nucleic Acids.

PCR methods have been extensively developed during the last decade. An example protocol is as follows. A sample containing 10–10,000 copies of a source DNA molecule is mixed with two antiparallel DNA primers that surround a targeted sequence, e.g. the coding region for a gene involved in carcinogenesis. The PCR mix is composed of: 8 $\mu$l 2.5 mM deoxynucleoside triphosphates, 10 $\mu$l 10X PCR buffer, 10 $\mu$l 25 mM $MgCl_2$, 3 $\mu$l 10 $\mu$M forward primer, 3 $\mu$l 10 $\mu$M reverse primer, 0.3 $\mu$l thermostable Taq DNA polymerase, 64.7 $\mu$l $H_2O$, and 1 $\mu$l source DNA. The sample tube is sealed and placed into a thermal cycling device. A typical cycling protocol is as follows:

| Step 1 | 95° C. 2 min. |
| Step 2 | 95° C. 15 sec. |
| Step 3 | 55° C. 15 sec. |
| Step 4 | 72° C. 1 min. |
| Step 5 | repeat Steps 2–4 35 times |
| Step 6 | 72° C. 5 min. |
| Step 7 | stop |

Example 2. Production of Single-Stranded Nucleic Acids by Asymmetric PCR.

The basic PCR procedure can be modified in order to produce predominantly one of the two strands. These asymmetric procedures involve modifying the ratios of the two primers, a typical ratio is 10:1.

Example 3. Production of Single-Stranded DNA via Biotinylated PCR Products.

For the preparation of capture probes one of the two primers can be synthesized with a biotin moiety internally or at the 5' end of the oligonucleotide. Following a standard PCR, the double-stranded product can be bound to a solid-phase surface coated with streptavidin. For example, 10 pmol of double-stranded PCR product is mixed with 5 $\mu$l MPG [10 mg/ml] paramagnetic streptavidin-coated beads in a binding/washing buffer of 2.0 M NaCl, 10 mM TrisCl, 1 mM EDTA, pH 8.0. The solution is incubated for 15 min. at room temperature with mixing. Following incubation the tube is placed next to a high field, rare earth magnet and the paramagnetic beads with the bound biotinylated PCR product are precipitated to the wall of the tube. The supernatant is removed, and the particles, outside the influence of the magnetic field, are resuspended into binding/washing buffer. The beads and wash solution are mixed and then subjected once again to the magnetic field to precipitate the magnetic particles. The supernatant is once again removed and either the wash step is repeated or the alkaline denaturation step commences. In order to release the unbiotinylated strand from the double-stranded product the beads are mixed with an alkaline denaturation solution, 0.1 M NaOH. The beads are incubated at room temperature for 10 min. which denatures the PCR product and releases the unbiotinylated product into solution. The biotinylated strand, bound to the magnetic beads is precipitated from the solution under the magnetic field and unbiotinylated strand, now single-stranded, is transferred to a new tube with the supernatant. In an optional secondary step, the now single-stranded biotinylated strand can be freed from the magnetic beads by boiling the beads in water for 10 min and transferred with the new supernatant after magnetic precipitation of the magnetic beads.

Example 4. Mass Modification of Target Nucleic Acids.

Mass modification of the target nucleic acid is performed during the amplification step. One or more standard deoxynucleoside triphosphates are replaced with modified deoxynucleoside triphosphates. As an example thymidine is replaced with a 5-alkynyl-substituted-2'-deoxyuridine triphosphate. Because the modified nucleotides may not be efficient substrates for DNA polymerase it may be necessary to increase the concentration of the corresponding triphosphate by a factor of 2 to 100 over normal levels.

Example 5. Nonrandom Fragmentation of Double-Stranded Target Nucleic Acids Using Restriction Endonucleases Specifically-sized, double-strand DNA products produced, for example, by PCR are subjected to sequence-specific fragmentation using restriction endonucleases. As an example, 10 pmoles of a 500 base pair PCR product is treated with one unit each of the frequently cutting enzymes Mnl I and HinP I in the buffer recommended by the enzyme supplier. The reaction is incubated at 37° C. for 1 hour, followed by an enzyme-denaturing incubation at 65° C. for 15 min.

Example 6. Nonrandom Fragmentation of Single-Stranded Target Nucleic Acids Using Small Oligonucleotide Restriction Site Probes in Combination with Restriction Endonucleases.

Single-stranded DNA target, produced, for example, by asymmetric PCR or by the solid phase methods described in Example 3, is mixed with small oligonucleotide restriction probes complementary to selected restriction site locations. As an example, a set of 10 base long probes targeting the Hae III recognition sequence, are synthesized with the sequence (SEQ ID NO: 1) 5' NNNGGCCNNN 3', where the N's are chosen to allow the restriction site probes to fully complement the single-stranded target DNA at the sites where the Hae III recognition site (e.g. the probe (SEQ ID NO: 2) 5' GACGGCCAAA 3' to complement the target sequence (SEQ ID NO: 3) 5' . . . TTTGGCCGTC . . . 3'). The mixture of target and probes, dissolved in the restriction buffer to be used in the cleavage step, is denatured at 95° C. and then incubated at 32° C. (the average $T_m$ melting temperature for the probes) for 15 min. allowing the probes to anneal to target and producing a mixture of single-stranded and double-stranded regions within the target nucleic acid. The hybridized product is then cleaved at the double-stranded sites using one or more specific restriction endonucleases (e.g. Hae III), under conditions similar to those described in Example 3.

Example 7. Nonrandom Fragmentation of Single-Stranded Target Nucleic Acids Using Fragmentation Probes in Combination with Single-Strand-Specific Endonucleases.

Single-stranded DNA target, produced, for example, by asymmetric PCR or by the solid phase methods described in Example 3, are mixed with fragmenting probes complementary to the target DNA. As an example, a mixture of probes with sizes of 24, 26, 28, 30, 32, and 34 each with sequences complementary to different, nonoverlapping regions of the single-stranded target DNA. The mixture of target and probes, dissolved in S1 nuclease digest buffer comprised of 50 mM NaAcetate pH 4.5, 280 mM NaCl, 50 mM $MgCl_2$, and 4.5 mM $ZnSO_4$, are denatured at 95° C. and then incubated at 55° C. (the average $T_m$ for the probes) for 15 min. allowing the probes to anneal to target and producing a mixture of single-stranded and double-stranded regions within the target nucleic acid. The hybridized product is then digested in the single-stranded regions using 1 U S1 nuclease per μg target DNA, incubated at room temperature for 30 min.

Example 8. Nonrandom Fragmentation of Single-Stranded Target Nucleic Acids Using Mismatch-Specific Cleavage.

Example 8.1. Chemical Cleavage at Mismatched Cytosine

A heterozygous, mutation-containing DNA target is produced, either by PCR of a heterozygous source nucleic acid or by hybridization of wild-type probes to a mutation-containing single-stranded target DNA. For solid phase capture and purification protocols the DNA probes are synthesized either chemically or enzymatically in such a way as to contain biotin moieties. By either route, when a mutation is present a mismatch forms between the target and wild type. A cleavage solution of hydroxylamine is prepared by dissolving 1.39 g of hydroxylamine hydrochloride in 1.6 mL of warm $H_2O$ followed by the dropwise addition of 1.75 mL of diethylamine to yield a solution of pH 6. A 6 mL sample of double-stranded DNA containing a mismatch site is mixed with a 20 mL of hydroxylamine solution and the resulting solution is incubated at 37° C. for 30 minutes. The reaction is stopped by the addition of 374 mL of $H_2O$ and the solution is removed either by solid phase capture of the reaction products using magnetic beads with washes performed in a similar manner to that described in Example 3 or by multistep centrifugation in a Microcon-30 ultrafiltration unit (Amicon). The reaction products are redissolved in 45 mL of $H_2O$ and 5 mL of piperidine is added. The solution is incubated at 90° C. for 30 minutes and then placed on ice to cool. A 300 mL portion of $H_2O$ is added and samples are either evaporated to dryness or purified by one of the two methods described in Examples 9 and 10.

Figure 14:
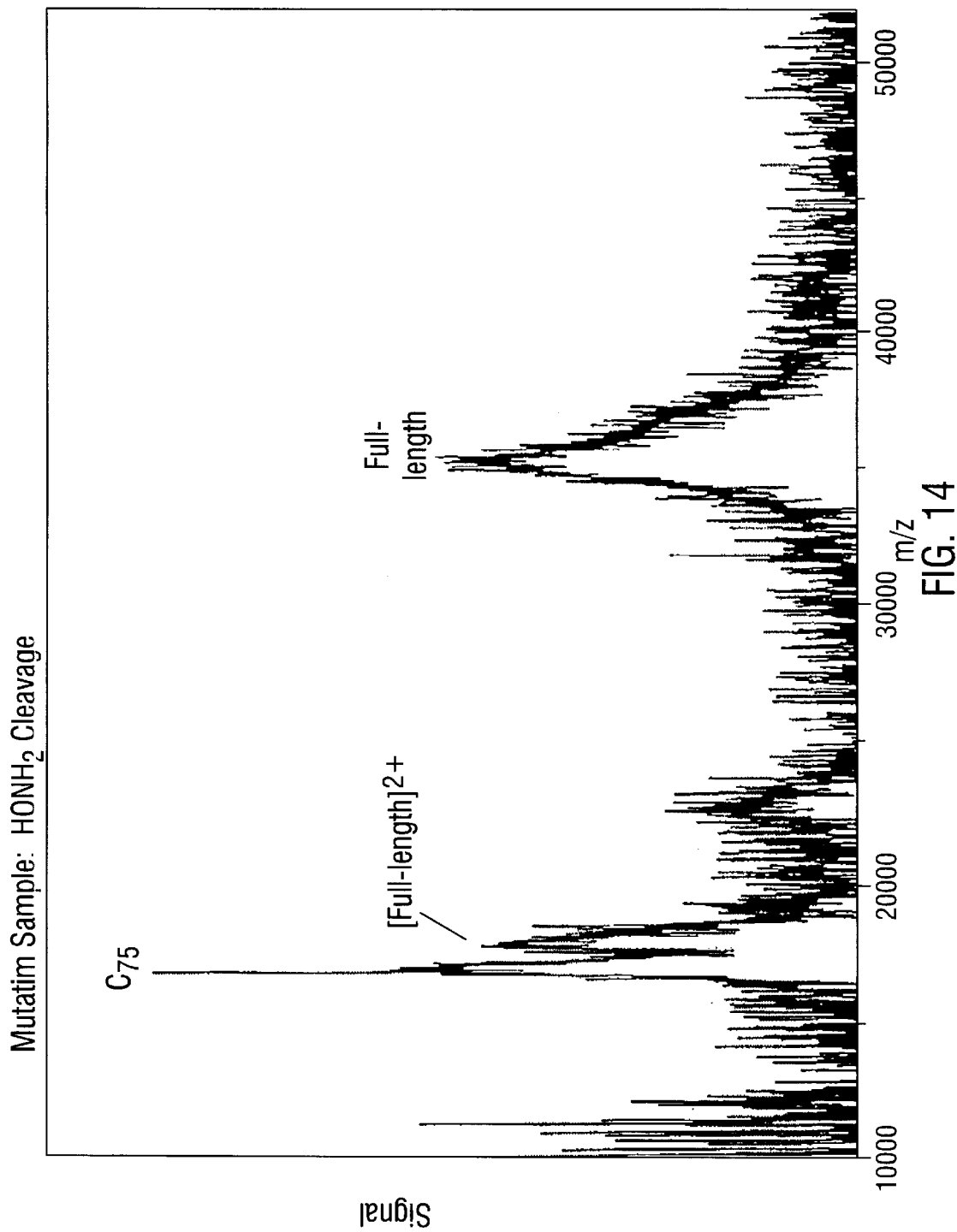
FIG. 14 is a mass spectrum of a set of nonrandom length fragments from a target nucleic acid containing a mutation, wherein the target nucleic acid is nonrandomly fragmented with hydroxylamine followed by piperidine, resulting in mutation-specific cleavage at a mismatch. This mass spectrum illustrates the presence of a nonrandom length fragment of 75 bases in size, that results from mutation-specific cleavage.
Figure 15:
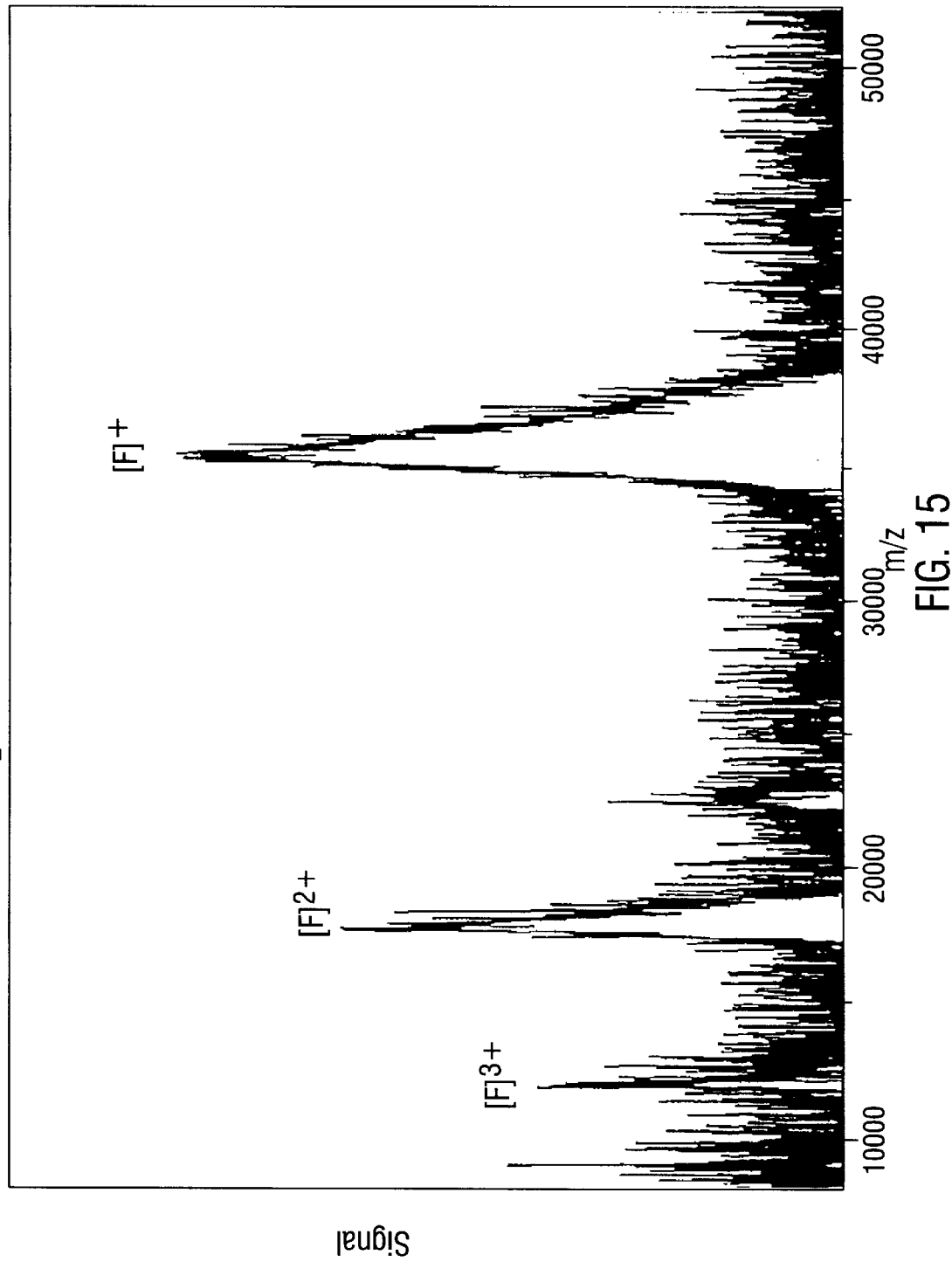
FIG. 15 is a mass spectrum illustrating hydroxylamine fragmentation of a wild type control of the mutation-containing target nucleic acid of FIG. 14. This mass spectrum lacks a fragment of 75 bases in size due to the lack of a mutation in the wild type target nucleic acid.

A typical mass spectrum obtained from the hydroxylamine fragmentation at a point mutation is shown in FIG. 14. The source DNA in this case is a section of the coding sequence for the p53 gene. A 134 base long PCR product is produced as in Example 1, amplifying p53 from codon 188 to 233 containing a heterozygous point mutation in codon 213, CGA->TGA. The forward primer containing a 5'-biotin and a chemically labile linker within the primer, the reverse primer being a standard oligonucleotide. The mismatch containing PCR product is treated with hydroxylamine as described above, cleaving the mismatch at C in codon 213. The product is purified as described in Example 10, and analyzed as described in Example 11. A strong peak appears at the mass correlating to a product 75 bases in size identifying that a C is present in a mismatch in the first position of codon 213. An analysis of mutation-free wild type, shown in FIG. 15, contains no mismatch and therefore no cleavage occurs.

Example 8.2. Chemical Cleavage at Mismatched Thymine

DNA is obtained in a similar manner to Example 8.1. The modification reagent is a 20 mM solution of $KMnO_4$ in deionized $H_2O$. To 6 mL of double-stranded DNA containing a mismatch site is added 14 mL of the modification reagent. The solution is mixed gently at room temperature over the course of two minutes during which time the solution turns slightly brown. A 20 mL portion of a solution consisting of 1.25 M sodium acetate pH 8.5 and containing 1 M 2-mercaptoethanol is added to stop the reaction, which results in the solution becoming immediately colorless. A 360 mL portion of $H_2O$ is added and the solution is either spun through a Microcon-30 ultrafiltration unit 2X, collected, and then evaporated to dryness or taken through a solid phase capture and wash protocol. The DNA is redissolved in 45 mL of $H_2O$ and 5 mL of piperidine is added. The resulting solution is heated to 90° C. for 30 minutes and then placed on ice to cool. After it cools, the solution is diluted by the addition of 300 mL of $H_2O$ and then evaporated to dryness. As an alternative the cleavage products can be purified by one of the two methods described in Examples 9 and 10.

Figure 16:
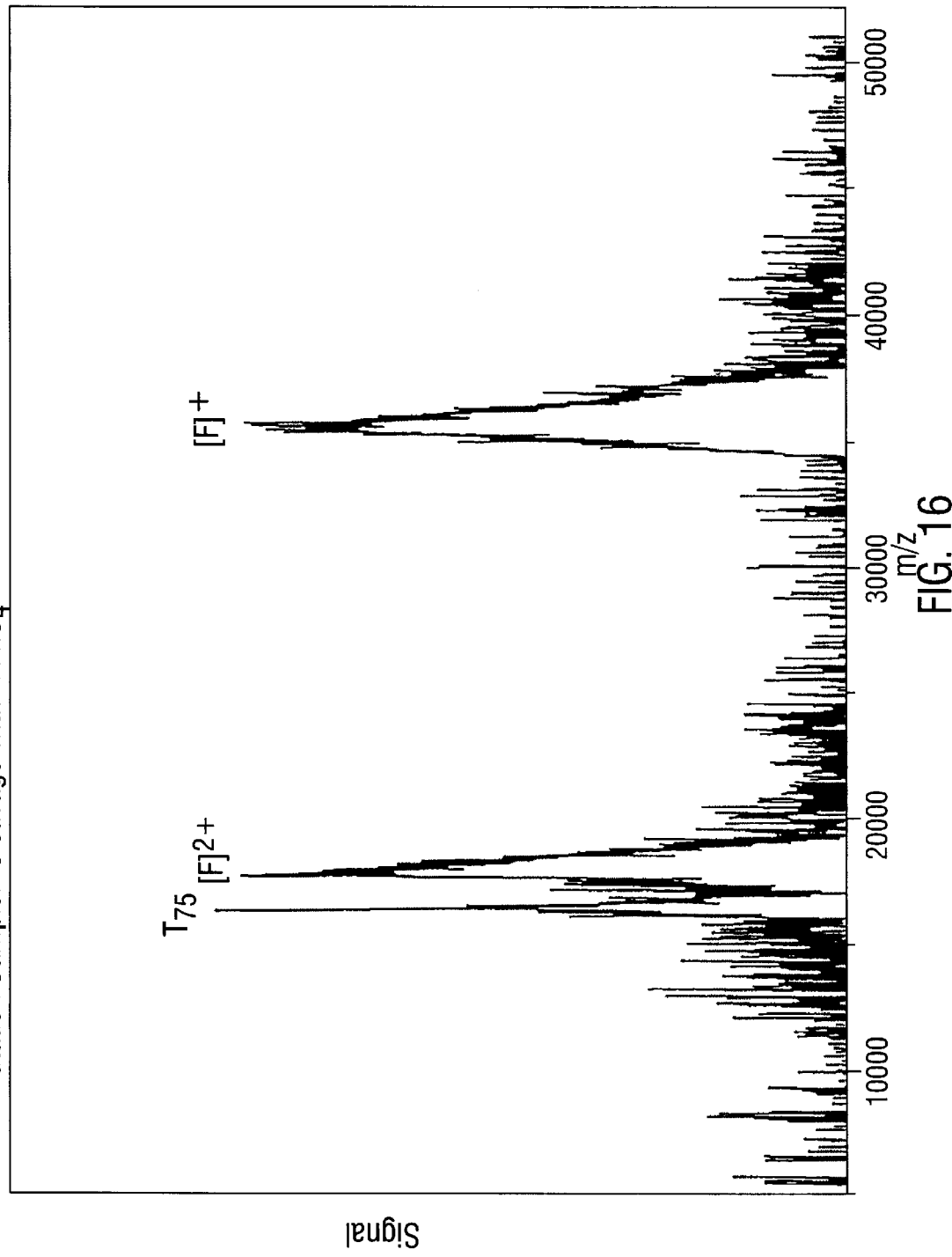
FIG. 16 is a mass spectrum of a mutation-containing target nucleic acid that is specifically cleaved with potassium permanganate at the site of a base mismatch.

A typical mass spectrum obtained from the $KMnO_4$ fragmentation at a point mutation is shown in FIG. 16. The source DNA in this case is a section of the coding sequence for the p53 gene. A 134 base long PCR product is produced as in Example 1, amplifying p53 from codon 188 to 233 containing a heterozygous point mutation in codon 213, CGA->TGA. The forward primer containing a 5'-biotin and a chemically labile linker within the primer, the reverse primer being a standard oligonucleotide. The mismatch containing PCR product is treated with $KMnO_4$ as described above, cleaving the mismatch at C in codon 213. The product is purified as described in Example 10, and analyzed as described in Example 11. A strong peak appears at the mass correlating to a product 75 bases in size identifying that a T is present in a mismatch in the first position of codon 213. Based on the data from the analysis in FIG. 14 and FIG. 16 it is possible to confirm that a C->T mutation has occurred in this p53 sample.

Example 9. Purification of Nonrandom Length Fragments Using Capture Probes

Nonrandom fragments are purified by annealing to a capture probes. The capture probe or probes consists of a sequence or sequences complementary to the selected target nonrandom length fragments. One method uses the a full length capture probe prepared as described in Example 3, another uses a number of chemically synthesized capture probes prepared with biotin covalently attached. For either method the procedure is identical. A 10 μL sample containing a single full-length biotinylated capture probe or a mixture of smaller, synthetic, biotinylated capture probes is mixed with 10 μL of nonrandom fragments in an annealing buffer consisting of 300 mM NaCl, 10 mM Tris, and 1 mM EDTA pH 7.5. The mixture is heated in a boiling-$H_2O$ bath for 10 min. and then quickly placed in an ice-$H_2O$ bath. The mixture is then transferred to a pre-heated thermal block at 42° C. (the temperature is adjusted depending on the $T_m$ of the capture probe or probes) and incubated for 1 hour. The solution is then allowed to cool and then mixed with streptavidin-coated magnetic beads. Binding to the beads takes place according to the procedure described in Example 3. After the binding step, in place of the alkaline denaturation step, the bound, hybridized nonrandom fragments are washed with a volatile buffer such as 1 M $NH_4HCO_3$. After 6 cycles of resuspension in 1 M $NH_4HCO_3$, magnetic precipitation, and removal of the supernatant, the beads are resuspended in 10 μL of deionized $H_2O$ and heated to 65° C. for 5 min. in order to release the nonrandom fragments from the bound biotinylated strand. The beads are quickly precipitated from the warm solution and the supernatant containing the nonrandom fragments is transferred to another tube. The solution of nonrandom fragments is dried to remove excess volatile buffer and then analyzed by mass spectrometry as described in Example 11.

Figure 17:
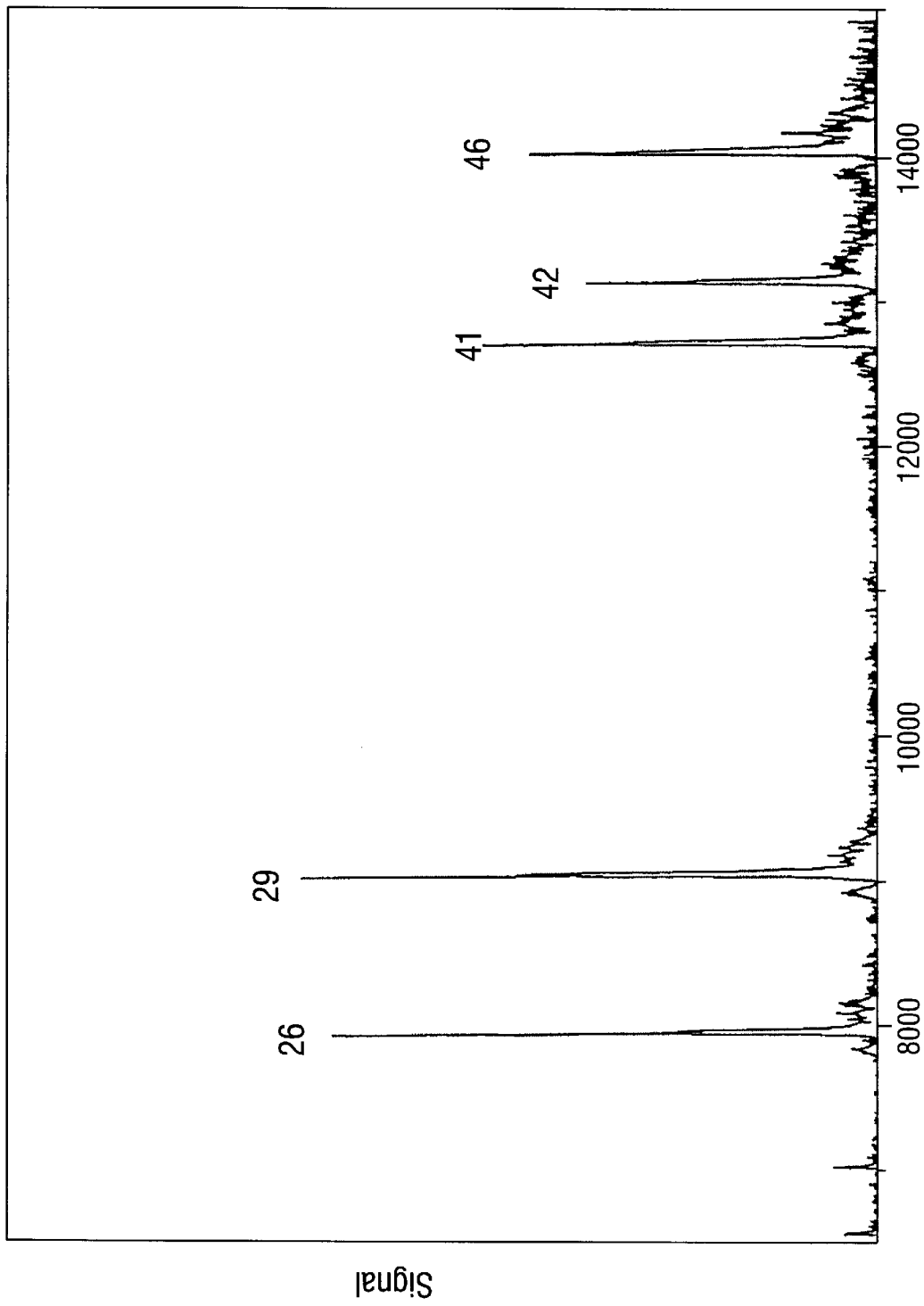
FIG. 17 is a mass spectrum of a set of 5 single-stranded nonrandom length fragments from an MNL I digest of a wild type target nucleic acid of 184 nucleotides in length.

An example of capture and analysis of nonrandom length fragments is shown in FIG. 17. The source DNA in this case is a section of the coding sequence for the p53 gene. A 184 base long PCR product is produced as in Example 1, amplifying p53 from codon 232 to 292 containing a heterozygous point mutation in codon 248, CGG->CAG. The double-stranded PCR product is digested using the restriction enzyme Mnl I under conditions described in Example 5. A full length capture probe of the negative strand is produced as in Example 3, and the nonrandom length fragments derived from the positive strand are captured and purified as described above. The purified single-stranded fragments are analyzed as described in Example 11. Shown in FIG. 16 are the 5 single-stranded positive fragments produced from an Mnl I digest of the wild type 184 base long PCR product. By performing single-stranded isolation the five similarly sized negative strand fragments are eliminated from the spectra and all of the fragments are fully resolved.

Figure 18:
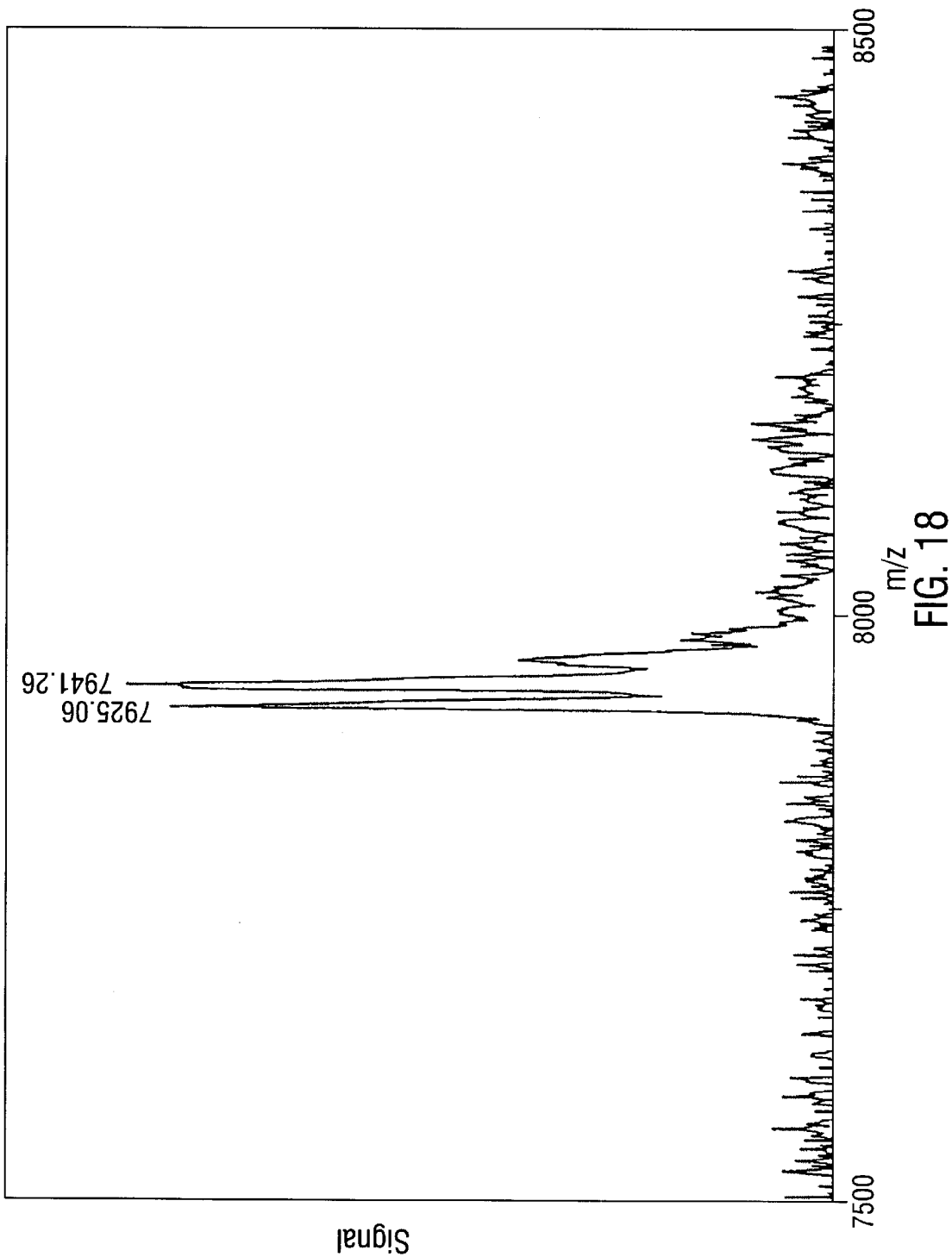
FIG. 18 is a magnified mass spectrum of two fragments, both 26 bases in length, identical in nucleotide sequence except for a single G to A point mutation, illustrating clear resolution of the two mass peaks.

Shown in FIG. 18 is a magnification of the spectra examining the 26 base long fragment that, in the heterozygous mutation case, contains the G->A mismatch. Shown are two clearly resolved peaks with a mass difference of 16 Da, exactly the difference between G and A and thus confirming the presence of a mutation. The third smaller peak correlates to a salt adduct of the high mass 26 base product and emphasizes the need for a process that stringently removes salt prior to analysis.

Example 10. Alternative Purification Method for Mismatch-Specific Nonrandom Length Fragments.

The purification of nonrandom fragments that were produced by a mutation-specific cleavage, e.g. chemical cleavage at mismatch sites, can be achieved in an alternative way. In this case the fragmentation is performed on a PCR product that has one solid-phase capturable strand, e.g. containing biotin, and that is also able to be cleaved from the solid support, e.g. a bridging phosphorothioate linkage contained in the primer region [Mag et al., Nucleic Acids Res. 19(7):1437–1441 (1991)]. As an example of this method, a PCR reaction is performed as described in Example 1, but with one of the primers containing a 5'-end biotin modification and also a bridging phosphorothioate linkage located 3–5 bases from the 3'-end, and the other primer a normal one. After amplification the PCR product is subjected to a mutation-specific fragmentation method directly since, for heterozygous mutations, mismatch-containing heteroduplexes are formed in situ during the PCR. In order to check for the possibility of a homozygous mutation, the sample is mixed with an equal amount of wild type control, annealed and then subjected to the fragmentation reaction. The material recovered from the fragmentation reactions is purified and made single-stranded by the method described in Example 3. In this case, after the denaturing step, the products are released from the magnetic beads after several $H_2O$ washes by treatment with 5 μL of 0.02 mM $AgNO_3$ and incubating at 45° C. for 15 min. The Ag+ ions are sequestered by the addition of 1 μL of 100 mM DTT. The samples are dried to remove excess DTT and then analyzed by mass spectrometry by the method described in Example 11.

Example 11. Mass Spectrometry Analysis.

The nucleic acid sample to be analyzed is typically mixed with an equal volume of matrix solution consisting of 0.5 M 3-hydroxypicolinic acid (3-HPA) and 50 mM diammonium hydrogen citrate. Typically a 1 μL portion of the sample is applied to the mass spectrometer sample stage and allowed to dry under a gentle stream of nitrogen gas at room temperature. When the sample has completely dried to form crystals (typically 5 min.) the sample is inserted into the mass spectrometer for analysis. The usual analysis conditions employ the use of a Nd:YAG laser operating at 266 nm with an average pulse energy of 50 mJ/$cm^2$. An average of 100 laser shots is typically used to obtain a spectrum.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the invention and the appended claims.

We claim:

1. A method of detecting mutations in a target nucleic acid comprising:

obtaining from said target nucleic acid, a set of nonrandom length fragments (NLFs) in single stranded form, wherein said set comprises NLFs derived from a single-stranded or double-stranded target nucleic acid, wherein said set of single stranded NLFs does not comprise the entirety of fragments generated from non-randomly fragmenting a double-stranded target nucleic acid, and determining masses of the members of said set using mass spectrometry.

2. The method of claim 1 wherein at least one member of said set of single-stranded NLFs has one or more nucleotides replaced with mass-modified nucleotides.

3. The method of claim 1 wherein said determining step further comprises utilizing internal self-calibrants.

4. The method of claim 1 wherein said target nucleic acid is single-stranded and said obtaining step further comprises:

hybridizing said single-stranded target nucleic acid to one or more sets of fragmenting probes to form hybrid target nucleic acid/fragmenting probe complexes comprising at least one double-stranded region and at least one single-stranded region, and nonrandomly fragmenting said target nucleic acid by cleaving said hybrid target nucleic acid/fragmenting probe complexes at every single-stranded region with at least one single-strand-specific cleaving reagent to form a set of NLFs.

5. The method of claim 4 wherein said set of fragmenting probes leaves single-stranded gaps between double-stranded regions formed by hybridization of said set of fragmenting probes to said target nucleic acid.

6. The method of claim 5 wherein said hybridizing step further comprises:

providing two single-stranded target nucleic acids and separately hybridizing a first set of fragmenting probes to a first single-stranded target nucleic acid and a second set of fragmenting probes to a second single-stranded target nucleic acid, wherein said members of said second set of fragmenting probes comprise at least one single-stranded nucleotide sequence complementary to regions of said first target nucleic acid that are not complementary to any nucleotide sequences in any members of said first set of fragmenting probes.

7. The method of claim 6 wherein said members of said first set of fragmenting probes comprise nucleotide sequences that overlap with nucleotide sequences of said members of said second set of fragmenting probes.

8. The method of claim 4 wherein at least one single-strand-specific cleaving reagent is a single-strand-specific endonuclease.

9. The method of claim 4 wherein at least one single-strand-specific cleaving reagent is a single-strand specific chemical cleaving reagent.

10. The method of claim 9 wherein said single-strand specific chemical cleaving reagent is selected from the group consisting of hydroxylamine, hydrogen peroxide, osmium tetroxide, and potassium permanganate.

11. The method claim 4 further comprising after said nonrandomly fragmenting step;

hybridizing one or more of said NLFs to one or more capture probes, wherein said capture probes comprise a single-stranded region complementary to at least one of said NLFs and a first binding moiety, binding said first binding moiety to a second binding moiety attached to a solid support, wherein said binding occurs either before or after said hybridizing of said NLFs to one or more capture probes, and isolating a set of single-stranded NLFs.

12. The method of claim 4 wherein said fragmenting probes comprise a single-stranded nucleotide sequence and a first binding moiety, further comprising:

after said nonrandomly fragmenting step, binding said first binding moiety to a second binding moiety attached to a solid support, and isolating said set of single-stranded NLFs.

13. The method of claim 1 wherein said obtaining step further comprises:

nonrandomly fragmenting said target nucleic acid with one or more restriction endonucleases to form a set of NLFs, hybridizing one or more of said set of NLFs or a subset thereof to one or more oligonucleotide probes, wherein each of said oligonucleotide probes comprises a nucleic acid comprising a single-stranded region and a first binding moiety, binding said first binding moiety to a second binding moiety attached to a solid support either before or after said hybridizing step, and isolating said set or subset of single-stranded NLFs.

14. The method of claim 13 wherein all of said oligonucleotide probes consist of one of either full-length positive or full-length negative single strands of said target nucleic acid and a first binding moiety.

15. The method of claim 13 wherein said binding between said first binding moiety and said second binding moiety is a covalent attachment.

16. The method of claim 13 wherein one binding moiety is a member selected from the group consisting of an antibody, a hormone, an inhibitor, a co-factor portion, a binding ligand, and a polynucleotide sequence, and the other binding moiety is a corresponding member selected from the group consisting of an antigen capable of recognizing said antibody, a receptor capable of recognizing said hormone, an enzyme capable of recognizing said inhibitor, a cofactor enzyme binding site capable of recognizing said co-factor portion, a substrate capable of recognizing said binding ligand, and a complementary polynucleotide sequence.

17. The method of claim 13 wherein said isolating further comprises:

washing said set of NLFs bound to said solid support with a solution comprising volatile salts selected from the group consisting of ammonium bicarbonate, dimethyl ammonium bicarbonate, and trimethyl ammonium bicarbonate.

18. The method of claim 1 wherein said target nucleic acid is single-stranded and wherein said obtaining step further comprises:

hybridizing said single-stranded target nucleic acid to one or more restriction site probes to form hybridized target nucleic acids having double-stranded regions, where said restriction site probes have hybridized to said single-stranded target nucleic acids, and at least one single-stranded region, and nonrandomly fragmenting said hybridized target nucleic acids using one or more restriction endonucleases that cleave at restriction sites within said double-stranded regions.

19. The method of claim 18 further comprising after said nonrandomly fragmenting step, hybridizing said NLFs to one or more capture probes, wherein said capture probes comprise a single-stranded region complementary to at least one of said NLFs and a first binding moiety, binding said first binding moiety to a second binding moiety attached to a solid support, wherein said binding occurs either before or after said hybridizing of said NLFs to one or more capture probes, and isolating a set of single-stranded NLFs.

20. The method of claim 19 wherein said cleaved restriction site probes comprise a single-stranded region complementary to half of a restriction endonuclease site and a first binding moiety, and further comprising after said nonrandomly fragmenting step, binding said first binding moiety to a second binding moiety attached to a solid support, and isolating a set of single-stranded NLFs.

21. The method of claim 1 wherein said target nucleic acid is single-stranded and said obtaining step further comprises:

providing conditions permitting folding of said single-stranded target nucleic acid to form a three-dimensional structure having intramolecular secondary and tertiary interactions, nonrandomly fragmenting said folded target nucleic acid with at least one structure-specific endonuclease to form a set of single-stranded NLFs, modifying either said target nucleic acid or said set of single-stranded NLFs such that members of said set of single-stranded NLFs comprise a single-stranded nucleotide sequence and at least one first binding moiety, binding said first binding moiety to a second binding moiety attached to a solid support, and isolating said set of single-stranded NLFs.

22. The method of claim 1 wherein said target nucleic acid is single-stranded and said obtaining step further comprises:

providing conditions permitting folding of said single-stranded target nucleic acid to form a three-dimensional structure having intramolecular secondary and tertiary interactions, nonrandomly fragmenting said folded target nucleic acid with at least one structure-specific endonuclease to form a set of single-stranded NLFs, hybridizing one or more of said set of NLFs to one or more capture probes, wherein said capture probes comprise a single-stranded nucleotide sequence and a first binding moiety, binding said first binding moiety to a second binding moiety attached to a solid support either before or after said hybridizing step, and isolating a set of single-stranded NLFs.

23. The method of claim 21 wherein said isolated set of single-stranded NLFs comprise any NLFs having a 5' end of said target nucleic acid.

24. The method of claim 22 wherein said isolated set of single-stranded NLFs comprise any NLFs having a 5' end of said target nucleic acid.

25. The method of claim 21 wherein said structure-specific endonuclease is selected from the group consisting of:

T4 endonuclease VII, RuvC, MutY, and the endonucleolytic activity from the 5'–3' exonuclease subunit of thermo-stable polymerases.

26. The method of claim 1 wherein said target nucleic acid is single-stranded and wherein said obtaining step further comprises:

hybridizing said single-stranded target nucleic acid to one or more wild type probes, and nonrandomly fragmenting said target nucleic acid with one or more mutation-specific cleaving reagents that specifically cleave at any regions of nucleotide mismatch that form between said target nucleic acid and any of said wild type probes.

27. The method of claim 26 wherein said nonrandomly fragmenting step further comprises:

digesting said first set of nonrandom length fragments with one or more restriction endonucleases.

28. The method of claim 26 wherein members of said set of single-stranded NLFs comprise a single-stranded region and at least one first binding moiety, further comprising after said nonrandomly fragmenting step, binding said first binding moiety to a second binding moiety attached to a solid support, and isolating a set of single-stranded NLFs.

29. The method of claim 26 wherein said obtaining step further comprises:

hybridizing members of said set of NLFs to one or more capture probes, wherein said capture probes comprise a single-stranded nucleotide sequence and at least one first binding moiety, binding said first binding moiety to a second binding moiety attached to a solid support, and isolating a set of single-stranded NLFs.

30. The method of claim 26 wherein said obtaining step further comprises:

isolating a set of single-stranded NLFs comprising any NLFs having a 5' end of said target nucleic acid.

31. The method of claim 26 wherein said nonrandomly fragmenting step further comprises:

cleaving said first set of nonrandom length fragments with one or more single-strand-specific cleaving reagents.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ix) FEATURE:
      (A) NAME/KEY: modified_base
      (B) LOCATION: 1..10
      (D) OTHER INFORMATION: /note= "N = A or C or G or T/U"

(xi) SEQUENCE DESCRIPTION: SEQ ID NO:1:

NNNGGCCNNN                                      10

(2) INFORMATION FOR SEQ ID NO:2:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (xi) SEQUENCE DESCRIPTION: SEQ ID NO:2:

GACGGCCAAA                                      10

(2) INFORMATION FOR SEQ ID NO:3:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (xi) SEQUENCE DESCRIPTION: SEQ ID NO:3:

TTTGGCCGTC                                      10